United States Patent
Schwab et al.

(10) Patent No.: US 11,111,511 B2
(45) Date of Patent: *Sep. 7, 2021

(54) METHOD FOR PRODUCING PHYTOSPHINGOSINE OR SPHINGANINE

(71) Applicants: AJINOMOTO CO., INC., Tokyo (JP); EVOLVA SA, Reinach (CH)

(72) Inventors: Markus Schwab, Loerrach (DE); Maud Babau, Copenhagen (DK); David Fischer, Arlesheim (CH); Anaelle Hatsch, Hesingue (FR); Sabina de Andrade Pereira Tavares, Basel (CH); Curt Aime Friis Nielsen, Reinach (CH); Jens Klein, Oberwil (CH); Corina Daniela Wirdnam, Reinach (CH)

(73) Assignees: AJINOMOTO CO, INC., Tokyo (JP); EVOLVA SA, Reinach (CH)

( * ) Notice: Subject to any disclaimer, the term of this patent is extended or adjusted under 35 U.S.C. 154(b) by 156 days.

This patent is subject to a terminal disclaimer.

(21) Appl. No.: 15/898,369

(22) Filed: Feb. 16, 2018

(65) Prior Publication Data

US 2018/0179562 A1   Jun. 28, 2018

Related U.S. Application Data

(63) Continuation of application No. PCT/JP2016/003866, filed on Aug. 24, 2016.
(Continued)

(30) Foreign Application Priority Data

Aug. 24, 2015   (JP) ............... JP2015164693

(51) Int. Cl.
*C12P 13/00*   (2006.01)
*C12N 9/12*   (2006.01)
(Continued)

(52) U.S. Cl.
CPC .............. *C12P 13/001* (2013.01); *C12N 1/16* (2013.01); *C12N 9/12* (2013.01); *C12N 9/1205* (2013.01);
(Continued)

(58) Field of Classification Search
None
See application file for complete search history.

(56) References Cited

U.S. PATENT DOCUMENTS

2008/0299625 A1* 12/2008 Van Den Berg ...... C12P 13/001
435/128
2010/0304467 A1* 12/2010 Kodama .................. C12N 1/18
435/254.2
(Continued)

FOREIGN PATENT DOCUMENTS

EP   2157186 A1   2/2010
JP   2014-529400 A   11/2014
(Continued)

OTHER PUBLICATIONS

Karmelic et al., "Influence of growth phase and zeolite clinoptilolite on the concentration of sphingoid bases in *Saccharomyces uvarum* brewer's yeast", World Journal of Microbiology and Biotechnology, vol. 27, pp. 2969-2979, 2011 (Year: 2011).*
(Continued)

*Primary Examiner* — Richard C Ekstrom
(74) *Attorney, Agent, or Firm* — Cermak Nakajima & McGowan LLP; Shelly Guest Cermak

(57) ABSTRACT

A method for producing an objective substance such as phytosphingosine and sphinganine using yeast is provided. An objective substance is produced by cultivating yeast having an ability to produce the objective substance and modified so that the expression and/or activities of proteins encoded by LCB4 and CKA2 genes are reduced in a culture
(Continued)

medium, and collecting the objective substance from cells of the yeast and/or the culture medium.

15 Claims, 1 Drawing Sheet

Specification includes a Sequence Listing.

Related U.S. Application Data

(60) Provisional application No. 62/208,934, filed on Aug. 24, 2015.

(51) Int. Cl.
    *C12N 1/16*     (2006.01)
    *C12P 1/02*     (2006.01)
    *C12P 7/64*     (2006.01)
    *C07C 215/10*     (2006.01)
    *C07F 9/09*     (2006.01)

(52) U.S. Cl.
    CPC ............... *C12P 1/02* (2013.01); *C12P 7/6481* (2013.01); *C12Y 207/01091* (2013.01); *C12Y 207/11001* (2013.01); *C07C 215/10* (2013.01); *C07F 9/09* (2013.01)

(56) References Cited

U.S. PATENT DOCUMENTS

| | | |
|---|---|---|
| 2014/0199736 A1 | 7/2014 | Kohler et al. |
| 2016/0304916 A1 | 10/2016 | Kohler et al. |
| 2018/0179562 A1* | 6/2018 | Schwab ............... C12N 9/12 |
| 2018/0179563 A1* | 6/2018 | Schwab ......... C12Y 305/01023 |

FOREIGN PATENT DOCUMENTS

| | | | |
|---|---|---|---|
| WO | WO-2006048458 A2 * | 5/2006 | ............ C12P 13/001 |
| WO | WO2013/023878 A1 | 2/2013 | |

OTHER PUBLICATIONS

UniProt Accession No. LCB4_YEAST, published Nov. 1, 1996 (Year: 1996).*
UniProt Accession No. CSK22_YEAST, published Feb. 1, 1991 (Year: 1991).*
Breslow et al., "Orm family proteins mediate sphingolipid homeostasis", Nature, vol. 463, pp. 1048-1053, 2010 (Year: 2010).*
Funato, K., et al., "Lcb4p Is a Key Regulator of Ceramide Synthesis from Exogenous Long Chain Sphingoid Base in *Saccharomyces cerevisiae*," J. Biol. Chem. 2003;278(9):7325-7334.
Cowart, L. A., et al., "Yeast sphingolipids: Recent developments in understanding biosynthesis, regulation, and function," Biochimica et Biophysica Acta 2007;1771:421-431.
Funato, K., et al., "Lcb4p Is a Key Regulator of Ceramide Synthesis from Exogenous Long Chaim Sphingoid Base in *Saccharomyces cerevisiae*," J. Biol. Chem. 2003;278(9):7325-7334.
Kobayashi, S. D., et al., "Ceramide/Long-Chain Base Phosphate Rheostat in *Saccharomyces cerevisiae*: Regulation of Ceramide Synthesis by Elo3p and Cka2p," Eukaryotic Cell 2003;2(2):284-294.
Schorsch, C., et al., "High-level production of tetraacetyl phytosphingosine (TAPS) by combined genetic engineering of sphingoid base biosynthesis and L-serine availability in the non-conventional yeast *Pichia ciferrii*," Metabolic Eng. 2012;14:172-184.
International Search Report for PCT Patent App. No. PCT/JP2016/003866 (dated Oct. 25, 2016).
Written Opinion for PCT Patent App. No. PCT/JP2016/003866 (dated Oct. 25, 2016).

* cited by examiner

METHOD FOR PRODUCING PHYTOSPHINGOSINE OR SPHINGANINE

This application is a Continuation of, and claims priority under 35 U.S.C. § 120 to, International Application No. PCT/JP2016/003866, filed Aug. 24, 2016, and claims priority therethrough under 35 U.S.C. § 119 to Japanese Patent Application No. 2015-164693, filed Aug. 24, 2015 and U.S. Provisional Application 62/208,934, filed Aug. 24, 2015, the entireties of which are incorporated by reference herein. Also, the Sequence Listing filed electronically herewith is hereby incorporated by reference (File name: 2018-02-16T_US-541_Seq_List; File size: 154 KB; Date recorded: Feb. 16, 2018).

BACKGROUND OF THE INVENTION

Field of the Invention

The present invention relates to a method for producing an objective substance such as phytosphingosine (PHS) and sphinganine (DHS) using yeast. PHS and DHS are industrially useful as ingredients for pharmaceuticals, cosmetics, and so forth.

Brief Description of the Related Art

There has been attempted to produce sphingoid bases and sphingolipids with bioengineering techniques. As methods for producing sphingoid bases and sphingolipids with bioengineering techniques, there have been reported methods of using yeast (W2014-529400).

LCB4 gene encodes a major sphingoid base kinase. LCB4 gene is reported to be a key regulator for the synthesis of ceramides from sphingoid bases (J Biol Chem. 2003 Feb. 28; 278(9):7325-34.). CKA2 gene encodes an alpha' subunit of casein kinase 2. CKA2 gene is reported to be required for full activation of ceramide synthase (Eukaryot Cell. 2003 April; 2(2):284-94.).

SUMMARY OF THE INVENTION

An object of the present invention is to develop a novel technique for improving production of an objective substance such as phytosphingosine (PHS) and sphinganine (DHS) by yeast, and thereby to provide a method for efficiently producing the objective substance.

The inventor of the present invention conducted research in order to achieve the aforementioned object. As a result, the inventor found that an ability of yeast to produce an objective substance such as phytosphingosine (PHS) and sphinganine (DHS) could be improved by modifying the yeast so that the expression and/or activities of proteins encoded by LCB4 and CKA2 genes are reduced, and accomplished the present invention.

That is, the present invention can be embodied, for example, as follows.

A method for producing an objective substance, the method comprising:
cultivating yeast having an ability to produce the objective substance in a culture medium; and
collecting the objective substance from cells of the yeast and/or the culture medium,
wherein the yeast has been modified so that the expression and/or activities of proteins encoded by LCB4 and CKA2 genes are reduced, and
wherein the objective substance is selected from the group consisting of phytosphingosine (PHS) and sphinganine (DHS).

The aforementioned method, wherein the activities of the proteins are reduced by attenuating the expression of the LCB4 and/or CKA2 gene, or by disrupting the LCB4 and/or CKA2 gene.

The aforementioned method, wherein the activities of the proteins are reduced by deletion of the LCB4 and CKA2 genes.

The aforementioned method, wherein the protein encoded by the LCB4 gene is a protein defined in (A), (B), or (C) mentioned below:
a protein comprising the amino acid sequence of SEQ ID NO: 10;
a protein comprising the amino acid sequence of SEQ ID NO: 10 but including substitution, deletion, insertion, and/or addition of 1 to 10 amino acid residues, and having sphingoid base kinase activity;
a protein comprising an amino acid sequence showing an identity of 90% or higher to the amino acid sequence of SEQ ID NO: 10, and having sphingoid base kinase activity.

The aforementioned method, wherein the protein encoded by the CKA2 gene is a protein defined in (A), (B), or (C) mentioned below:
a protein comprising the amino acid sequence of SEQ ID NO: 16;
a protein comprising the amino acid sequence of SEQ ID NO: 16 but including substitution, deletion, insertion, and/or addition of 1 to 10 amino acid residues, and having casein kinase 2 activity;
a protein comprising an amino acid sequence showing an identity of 90% or higher to the amino acid sequence of SEQ ID NO: 16, and having casein kinase 2 activity.

The aforementioned method, wherein the yeast has further been modified so that the expression and/or activity or activities of one or more proteins selected from proteins encoded by LCB5, ELO3, ORM2, and CHA1 genes are reduced.

The aforementioned method, wherein the activity or activities of the one or more proteins are reduced by attenuating the expression of the respective genes encoding the one or more proteins, or by disrupting the respective genes encoding the one or more proteins.

The aforementioned method, wherein the activity or activities of the one or more proteins are reduced by deletion of the respective genes encoding the one or more proteins.

The aforementioned method, wherein the yeast has further been modified so that the expression and/or activity or activities of one or more proteins selected from proteins encoded by LCB1, LCB2, TSC10, and SUR2 genes are increased.

The aforementioned method, wherein the activity or activities of the one or more proteins are increased by increasing the expression of the respective genes encoding the one or more proteins.

The aforementioned method, wherein the expression of the gene(s) is increased by modifying increasing the copy number of the gene(s), and/or by modifying an expression control sequence of the gene(s).

The aforementioned method, wherein the phytosphingosine is selected from the group consisting of C16 PHS, C18 PHS, C20 PHS, C18:1 PHS, C20:1 PHS, 4-(hydroxymethyl)-2-methyl-6-tetradecanyl-1,3-oxazinan-5-ol, and 4-(hydroxymethyl)-2-methyl-6-hexadecanyl-1,3-oxazinan-5-ol.

The aforementioned method, wherein the culture medium contains an additive that is able to associate with, bind to, solubilize, and/or capture the objective substance.

The aforementioned method, wherein the additive is selected from the group consisting of cyclodextrin and zeolite.

The aforementioned method, wherein the yeast belongs to the genus *Saccharomyces*.

The aforementioned method, wherein the yeast is *Saccharomyces cerevisiae*.

The aforementioned method, wherein the yeast is able to produce and accumulate the objective substance in a culture medium or cells of the yeast in an amount larger than that obtainable with a non-modified strain.

DETAILED DESCRIPTION OF THE PREFERRED EMBODIMENTS

Figure 1:
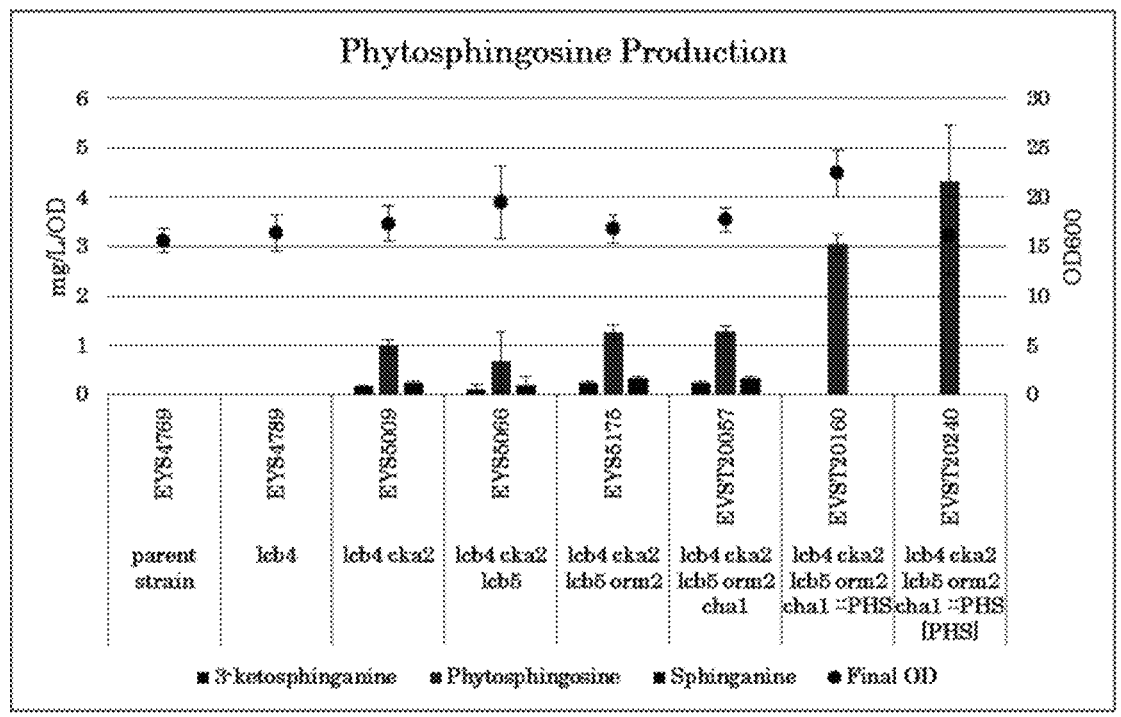
FIG. 1: The Figure shows data regarding PHS production in small scale cultures. PHS: sphingolipid pathway genes LCB1, LCB2, TSC10, and SUR2

Hereafter, the present invention will be explained in detail.

The method of the present invention is a method for producing an objective substance comprising cultivating yeast having an ability to produce the objective substance in a culture medium, and collecting the objective substance from cells of the yeast and/or the culture medium, wherein the yeast has been modified so that the expression and/or activities of proteins encoded by LCB4 and CKA2 genes are reduced. The yeast used for method of the present invention is also referred to as "the yeast of the present invention".

<1> Yeast of the Present Invention

The yeast of the present invention is yeast having an ability to produce an objective substance, which has been modified so that the activities of proteins encoded by LCB4 and CKA2 genes are reduced. The "ability to produce an objective substance" may also be referred to as "objective substance-producing ability".

<1-1> Yeast Having Objective Substance-Producing Ability

In the present invention, the term "yeast having an objective substance-producing ability" refers to yeast that is able to produce and accumulate an objective substance in a culture medium or cells of the yeast in such a degree that the objective substance can be collected, when the yeast is cultivated in the culture medium. The culture medium may be a medium that can be used in the method of the present invention, and may specifically be a medium containing an additive that is able to associate with, bind to, solubilize, and/or capture the objective substance. The yeast having an objective substance-producing ability may also be yeast that is able to produce and accumulate an objective substance in a culture medium or cells of the yeast in an amount larger than that obtainable with a non-modified strain. The term "non-modified strain" may refer to a reference strain that has not been modified so that an objective substance-producing ability is imparted or enhanced, and may specifically refer to a reference strain that has not been modified so that the expression and/or activities of proteins encoded by LCB4 and CKA2 genes are reduced. Examples of the non-modified strain include a wild-type strain and parent strain, such as *Saccharomyces cerevisiae* strains BY4742 (ATCC 201389; EUROSCARF Y10000), S288C (ATCC 26108), and NCYC 3608. The yeast having an objective substance-producing ability may also be yeast that is able to produce and accumulate an objective substance in a culture medium in an amount of preferably 5 mg/L or more, more preferably 10 mg/L or more.

In the present invention, the objective substance is selected from the group consisting of phytosphingosine (PHS) and sphinganine (DHS).

Phytosphingosine (PHS) and sphinganine (DHS) each comprise a long alkyl chain having an amino group at C2 and hydroxyl groups. The length and the unsaturation degree of the alkyl chain constituting the objective substance may vary. The alkyl chain may have a length of, for example, C16, C18, or C20. The alkyl chain may have one or more unsaturated double bonds. That is, examples of objective substance also include such variant species of phytosphingosine (PHS) and sphinganine (DHS), which variant species have different lengths and/or different unsaturation degrees. The term "phytosphingosine (PHS)" may refer to C18 PHS, which is a typical species of PHS, or may collectively refer to such variant species of PHS, such as C16 PHS, which has a saturated C16 alkyl chain; C18 PHS, which has a saturated C18 alkyl chain; C20 PHS, which has a saturated C20 alkyl chain; C18:1 PHS, which has a C18 alkyl chain having one unsaturated double bond; and C20:1 PHS, which has a C20 alkyl chain having one unsaturated double bond. The term "phytosphingosine (PHS)" may also include adducts of PHS, such as 4-(hydroxymethyl)-2-methyl-6-tetradecanyl-1,3-oxazinan-5-ol and 4-(hydroxymethyl)-2-methyl-6-hexadecanyl-1,3-oxazinan-5-ol, which may be generated via reaction of C18 PHS and C20 PHS with acetaldehyde, respectively. Similarly, the term "sphinganine (DHS)" may refer to C18 DHS, which is a typical species of DHS and has a saturated C18 alkyl chain, or may collectively refer to such variant species of DHS.

The objective substance to be produced may be a free compound, a salt thereof, or a mixture thereof. That is, in the present invention, the term "objective substance" may refer to an objective substance in a free form, a salt thereof, or a mixture thereof. Examples of the salt include, for example, inorganic acid salts such as sulfate salt, hydrochloride salt, and carbonate salt, and organic acid salts such as lactic acid salt and glycolic acid salt (Acta Derm Venereol. 2002; 82(3):170-3.). As the salt of the objective substance, one kind of salt may be employed, or two or more kinds of salts may be employed.

The yeast is not particularly limited so long as it can be used for the method of the present invention. The yeast may be budding yeast, or may be fission yeast. The yeast may be haploid yeast, or may be diploid or more polyploid yeast.

Examples of the yeast include yeast belonging to the genus *Saccharomyces* such as *Saccharomyces cerevisiae*, the genus *Pichia* (also referred to as the genus *Wickerhamomyces*) such as *Pichia ciferrii*, *Pichia sydowiorum*, and *Pichia pastoris*, the genus *Candida* such as *Candida utilis*, the genus *Hansenula* such as *Hansenula polymorpha*, the genus *Schizosaccharomyces* such as *Schizosaccharomyces pombe*. Some species of the genus *Pichia* has been reclassified into the genus *Wickerhamomyces* (Int J Syst Evol Microbiol. 2014 March; 64(Pt 3):1057-61). Therefore, for example, *Pichia ciferrii* and *Pichia sydowiorum* are also called *Wickerhamomyces ciferrii* and *Wickerhamomyces sydowiorum*, respectively. In the present invention, the term "*Pichia*" should include such species that had been classified into the genus *Pichia* but have been reclassified into another genus such as *Wickerhamomyces*.

Specific examples of *Saccharomyces cerevisiae* include strains BY4742 (ATCC 201389; EUROSCARF Y10000), S288C (ATCC 26108), Y006 (FERM BP-11299), NCYC 3608, and derivative strains thereof. Specific examples of *Pichia ciferrii* (*Wickerhamomyces ciferrii*) include strain NRRL Y-1031 (ATCC 14091), strain CS.PCΔPro2 (Schorsch et al., 2009, Curr Genet. 55, 381-9.), strains disclosed in WO 95/12683, and derivative strains thereof. Specific examples of *Pichia* sydowiorum (*Wickerhamomyces sydowiorum*) include strain NRRL Y-7130 (ATCC 58369) and derivative strains thereof.

These strains are available from, for example, the American Type Culture Collection (ATCC, Address: P.O. Box 1549, Manassas, Va. 20108, United States of America), EUROpean *Saccharomyces Cerevisiae* ARchive for Functional Analysis (EUROSCARF, Address: Institute for Molecular Biosciences, Johann Wolfgang Goethe-University Frankfurt, Max-von-Laue Str. 9; Building N250, D-60438 Frankfurt, Germany), the National Collection of Yeast Cultures (NCYC, Address: Institute of Food Research, Norwich Research Park, Norwich, NR4 7UA, UK), or depositary institutions corresponding to deposited strains. That is, for example, in cases of ATCC strains, registration numbers are assigned to the respective strains, and the strains can be ordered by using these registration numbers (refer to atcc.org). The registration numbers of the strains are listed in the catalogue of the American Type Culture Collection (ATCC).

The yeast of the present invention may be yeast inherently having an objective substance-producing ability, or may be yeast modified so that it has an objective substance-producing ability. The yeast having an objective substance-producing ability can be obtained by imparting an objective substance-producing ability to yeast such as those mentioned above, or by enhancing an objective substance-producing ability of yeast such as those mentioned above.

Hereafter, methods for imparting or enhancing an objective substance-producing ability will be specifically exemplified. All the modifications for imparting or enhancing an objective substance-producing ability may be used independently or in any appropriate combination. Modifications for constructing the yeast of the present invention can be performed in an arbitrary order.

An objective substance-producing ability may be imparted or enhanced by modifying yeast so that the expression and/or activity or activities of one or more kinds of proteins involved in production of the objective substance are increased or reduced. That is, the yeast of the present invention may have been modified so that the expression and/or activity or activities of one or more kinds of proteins involved in production of the objective substance are increased or reduced. The term "protein" also includes so-called peptides such as polypeptides. Examples of the proteins involved in production of the objective substance include enzymes that catalyze the synthesis of the objective substance (also referred to as "biosynthetic enzyme of objective substance"), enzymes that catalyze a reaction branching away from the biosynthetic pathway of the objective substance to generate a compound other than the objective substance (also referred to as "biosynthetic enzyme of byproduct"), enzymes that catalyze decomposition of the objective substance (also referred to as "decomposition enzyme of objective substance"), and proteins that affect, e.g. increase or reduce, the activity of an enzyme such as those described above.

The protein of which the expression and/or activity is to be increased or reduced can be appropriately chosen depending on the type of the objective substance and on the types and activities of the proteins involved in production of the objective substance and inherently possessed by the yeast of the present invention. For example, the expression and/or activity or activities of one or more kinds of proteins selected from biosynthetic enzymes of the objective substance may preferably be increased. Also, for example, the expression and/or activity or activities of one or more kinds of proteins selected from biosynthetic enzymes of a byproduct and decomposition enzymes of the objective substance may preferably be reduced.

Methods for increasing or reducing the expression and/or activity of a protein will be described in detail later. The activity of a protein can be increased by, for example, increasing the expression of a gene encoding the protein. The activity of a protein can be reduced by, for example, attenuating the expression of a gene encoding the protein or disrupting a gene encoding the protein. The expression of a gene is also referred to as "the expression of a protein (i.e. the protein encoded by the gene)". Such methods of increasing or reducing the expression and/or activity of a protein are well known in the art.

Specific examples of the proteins involved in production of the objective substance include proteins encoded by LCB1, LCB2, TSC10, SUR2, LCB4, LCB5, ELO3, CKA2, ORM2, and CHA1 genes. These genes may be collectively referred to as "target gene", and proteins encoded thereby may be collectively referred to as "target protein".

The yeast of the present invention at least has been modified so that the expression and/or activities of proteins encoded by LCB4 and CKA2 genes are reduced. The expression "the activities of proteins encoded by LCB4 and CKA2 genes are reduced" may specifically mean that the expression of LCB4 gene and/or CKA2 gene is attenuated, or LCB4 gene and/or CKA2 gene are disrupted. Reduction in the expression and/or activities of proteins encoded by LCB4 and CKA2 genes result in an increased objective substance-producing ability, and thus results in an increased production the objective substance. The yeast of the present invention can be obtained by modifying yeast having an objective substance-producing ability so that the expression and/or activities of proteins encoded by LCB4 and CKA2 genes are reduced. The yeast of the present invention can also be obtained by modifying yeast so that the expression and/or activities of proteins encoded by LCB4 and CKA2 genes are reduced, and then imparting or enhancing an objective substance-producing ability. The yeast of the present invention may also be yeast that has acquired an objective substance-producing ability by being modified so that the expression and/or activities of proteins encoded by LCB4 and CKA2 genes are reduced.

The yeast of the present invention may further have been modified so that the expression and/or activity or activities of one or more kinds of proteins selected from proteins encoded by LCB1, LCB2, TSC10, and SUR2 genes are increased, and/or that the expression and/or activity or activities of one or more kinds of proteins selected from proteins encoded by LCB5, ELO3, ORM2, and CHA1 genes are reduced. The expression "the activity or activities of one or more proteins selected from proteins encoded by LCB1, LCB2, TSC10, and SUR2 genes are increased" may specifically mean that the expression of one or more genes selected from LCB1, LCB2, TSC10, and SUR2 genes is increased. The expression "the activity or activities of one or more proteins selected from proteins encoded by LCB5, ELO3, ORM2, and CHA1 genes are reduced" may specifically mean that the expression of one or more genes selected from LCB5, ELO3, ORM2, and CHA1 genes is attenuated, or one or more genes selected from LCB5, ELO3, ORM2, and CHA1 genes are disrupted.

LCB1 and LCB2 genes encode serine palmitoyltransferase. The term "serine palmitoyltransferase" refers to a protein having an activity of catalyzing the synthesis of 3-ketosphinganine from serine and palmitoyl-CoA (EC 2.3.1.50). This activity may be referred to as "serine palmitoyltransferase activity". Proteins encoded by LCB1 and LCB2 genes may be referred to as "Lcb1p" and "Lcb2p", respectively. Examples of LCB1 and LCB2 genes include those of yeast such as S. cerevisiae and Pichia ciferrii. The nucleotide sequences of LCB1 and LCB2 genes of S. cerevisiae S288C are shown as SEQ ID NOS: 1 and 3, and the amino acid sequences of Lcb1p and Lcb2p encoded thereby are shown as SEQ ID NOS: 2 and 4. Lcb1p and Lcb2p may form a heterodimer to function as serine palmitoyltransferase (Plant Cell. 2006 December; 18(12):3576-93.). The activity or activities of either one or both of Lcb1p and Lcb2p may be increased. An increased activity or activities of either one or both of Lcb1p and Lcb2p may specifically mean an increased serine palmitoyltransferase activity. Serine palmitoyltransferase activity can be measured by, for example, a known method (J Biol Chem. 2000 Mar. 17; 275(11):7597-603.).

TSC10 gene encodes 3-dehydrosphinganine reductase. The term "3-dehydrosphinganine reductase" refers to a protein having an activity of catalyzing the conversion of 3-ketosphinganine to dihydrosphingosine (sphinganine) in the presence of an electron donor such as NADPH (EC 1.1.1.102). This activity may be referred to as "3-dehydrosphinganine reductase activity". A protein encoded by TSC10 gene may be referred to as "Tsc10p". Examples of TSC10 gene include those of yeast such as S. cerevisiae and Pichia ciferrii. The nucleotide sequence of TSC10 gene of S. cerevisiae S288C is shown as SEQ ID NO: 5, and the amino acid sequence of Tsc10p encoded thereby is shown as SEQ ID NO: 6. The activity of Tsc10p may be increased. An increased activity of Tsc10p may specifically mean an increased 3-dehydrosphinganine reductase activity. 3-dehydrosphinganine reductase activity can be measured by, for example, a known method (Biochim Biophys Acta. 2006 January; 1761(1):52-63.).

SUR2 (SYR2) gene encodes sphingosine hydroxylase. The term "sphingosine hydroxylase" refers to a protein having an activity of catalyzing the hydroxylation of a sphingoid base or the hydroxylation of sphingoid base moiety of a ceramide (EC 1.-.-.-). This activity may be referred to as "sphingosine hydroxylase activity". Sphingosine hydroxylase may catalyze, for example, the hydroxylation of dihydrosphingosine (DHS; sphinganine) to form phytosphingosine (PHS), or the hydroxylation of a ceramide containing DHS (dihydroceramide) to form a ceramide containing PHS (phytoceramide). A protein encoded by SUR2 gene may be referred to as "Sur2p". Examples of SUR2 gene include those of yeast such as S. cerevisiae and Pichia ciferrii. The nucleotide sequence of SUR2 gene of S. cerevisiae S288C is shown as SEQ ID NO: 7, and the amino acid sequence of Sur2p encoded thereby is shown as SEQ ID NO: 8. The nucleotide sequence of SUR2 gene of Pichia ciferrii is shown as SEQ ID NO: 21, and the amino acid sequence of Sur2p encoded thereby is shown as SEQ ID NO: 22. The activity of Sur2p may be increased, for example, in cases of producing PHS. An increased activity of Sur2p may specifically mean an increased sphingosine hydroxylase activity. Sphingosine hydroxylase activity can be measured by, for example, incubating the enzyme with DHS or a dihydroceramide and determining an enzyme-dependent production of PHS or a phytoceramide.

LCB4 and LCB5 genes encode sphingoid base kinases. The term "sphingoid base kinase" refers to a protein having an activity of catalyzing the phosphorylation a sphingoid base to form a sphingoid base phosphate (EC 2.7.1.91). This activity may be referred to as "sphingoid base kinase activity". Proteins encoded by LCB4 and LCB5 genes may be referred to as "Lcb4p" and "Lcb5p", respectively. The nucleotide sequences of LCB4 and LCB5 genes of S. cerevisiae S288C are shown as SEQ ID NOS: 9 and 11, and the amino acid sequences of Lcb4p and Lcb5p encoded thereby are shown as SEQ ID NOS: 10 and 12. Of these, Lcb4p is the major sphingoid base kinase in S. cerevisiae (J Biol Chem. 2003 Feb. 28; 278(9):7325-34.). At least the activity of Lcb4p is reduced. The activity of Lcb5p may also be reduced. A reduced activity or activities of either one or both of Lcb4p and Lcb5p may specifically mean a reduced sphingoid base kinase activity. Sphingoid base kinase activity can be measured by, for example, a known method (Plant Physiol. 2005 February; 137(2):724-37.).

ELO3 gene encodes fatty acid elongase III. The term "fatty acid elongase III" refers to a protein having an activity of catalyzing the elongation of C18-CoA to form C20-C26-CoA (EC 2.3.1.199). This activity may be referred to as "fatty acid elongase III activity". C26-CoA may preferably be used for the synthesis of ceramides catalyzed by ceramide synthase. A protein encoded by ELO3 gene may be referred to as "Elo3p". The nucleotide sequence of ELO3 gene of S. cerevisiae S288C is shown as SEQ ID NO: 13, and the amino acid sequence of Elo3p encoded thereby is shown as SEQ ID NO: 14. The activity of Elo3p may be reduced. A reduced activity of Elo3p may specifically mean a reduced fatty acid elongase III activity. Fatty acid elongase III activity can be measured by, for example, a known method (J Biol Chem. 1997 Jul. 11; 272(28):17376-84.).

CKA2 gene encodes an alpha' subunit of casein kinase 2. The term "casein kinase 2" refers to a protein having an activity of catalyzing the serine/threonine-selective phosphorylation of proteins (EC 2.7.11.1). This activity may be referred to as "casein kinase 2 activity". A protein encoded by CKA2 gene may be referred to as "Cka2p". The nucleotide sequence of CKA2 gene of S. cerevisiae S288C is shown as SEQ ID NO: 15, and the amino acid sequence of Cka2p encoded thereby is shown as SEQ ID NO: 16. Cka2p may form a heterotetramer in combination with CKA1, CKB1, and CKB2 gene products, i.e. Cka1p, Ckb1p, and Ckb2p, to function as casein kinase 2. Cka2p may be required for full activation of ceramide synthase (Eukaryot Cell. 2003 April; 2(2):284-94.). The activity of Cka2p may be reduced. A reduced activity of Cka2p may specifically mean a reduced casein kinase 2 activity. Also, a reduced activity of Cka2p may specifically mean a reduced ceramide synthase activity. Casein kinase 2 activity can be measured by, for example, a known method (Gene. 1997 Jun. 19; 192(2):245-50.).

ORM2 gene encodes a membrane protein that regulates serine palmitoyltransferase activity. A protein encoded by ORM2 gene may be referred to as "Orm2p". The nucleotide sequence of ORM2 gene of S. cerevisiae S288C is shown as SEQ ID NO: 17, and the amino acid sequence of Orm2p encoded thereby is shown as SEQ ID NO: 18. The activity of Orm2p may be reduced. A reduced activity of Orm2p may specifically mean an increased serine palmitoyltransferase activity.

CHA1 gene encodes L-serine/L-threonine ammonia-lyase. The term "L-serine/L-threonine ammonia-lyase" refers to a protein having an activity of catalyzing the reaction of degrading of L-serine and L-threonine (EC 4.3.1.17 and EC 4.3.1.19). This activity may be referred to as "L-serine/L-threonine ammonia-lyase activity". A protein encoded by CHA1 gene may be referred to as "Cha1p". The nucleotide sequence of CHA1 gene of *S. cerevisiae* S288C is shown as SEQ ID NO: 19, and the amino acid sequence of Cha1p encoded thereby is shown as SEQ ID NO: 20. The activity of Cha1p may be reduced. A reduced activity of Cha1p may specifically mean a reduced L-serine/L-threonine ammonia-lyase activity. L-serine/L-threonine ammonia-lyase activity can be measured by, for example, a known method (Eur J Biochem. 1982 April; 123(3):571-6.).

The target genes and proteins, i.e. LCB1, LCB2, TSC10, SUR2, LCB4, LCB5, ELO3, CKA2, ORM2, and CHA1 genes, and proteins encoded thereby, may have the aforementioned nucleotide and amino acid sequences. The expression "a gene or protein has a nucleotide or amino acid sequence" encompasses cases where a gene or protein comprises the nucleotide or amino acid sequence and cases where a gene or protein consists of the nucleotide or amino acid sequence.

The target genes may be variants of the respective genes exemplified above, so long as the original function thereof is maintained. Similarly, the target proteins may be variants of the respective proteins exemplified above, so long as the original function thereof is maintained. Such variants that maintain the original function thereof may also be referred to as "conservative variant". The term "LCB1", "LCB2", "TSC10", "SUR2", "LCB4", "LCB5", "ELO3", "CKA2", "ORM2", and "CHA1" genes include, in addition to the respective genes exemplified above, conservative variants thereof. Similarly, the term "Lcb1p", "Lcb2p", "Tsc10p", "Sur2p", "Lcb4p", "Lcb5p", "Elo3p", "Cka2p", "Orm2p", and "Cha1p" include, in addition to the respective proteins exemplified above, conservative variants thereof. That is, for example, the term "LCB1 gene" includes the LCB1 gene exemplified above, e.g. LCB1 gene of *S. cerevisiae*, and further includes variants thereof. Similarly, for example, the term "Lcb1 protein" includes the Lcb1 protein exemplified above, e.g. the protein encoded by LCB1 gene of *S. cerevisiae*, and further includes variants thereof. Examples of the conservative variants include, for example, homologues and artificially modified versions of the target genes and proteins exemplified above. Methods of generating variants of a gene or a protein are well known in the art.

The expression "the original function is maintained" means that a variant of a gene or protein has a function (such as activity and property) corresponding to the function (such as activity and property) of the original gene or protein. The expression "the original function is maintained" regarding a gene means that a variant of the gene encodes a protein of which the original function is maintained. The expression "the original function is maintained" regarding a protein means that a variant of the protein has the corresponding function such as activity and property exemplified above. That is, the expression "the original function is maintained" regarding the target proteins may mean that a variant protein has serine palmitoyltransferase activity as for Lcb1p and Lcb2p; 3-dehydrosphinganine reductase activity as for Tsc10p; sphingosine hydroxylase activity as for Sur2p; sphingoid base kinase activity as for Lcb4p and Lcb5p; fatty acid elongase III activity as for Elo3p; casein kinase 2 activity as for Cka2p; property of regulating serine palmitoyltransferase activity as for Orm2p; and L-serine/L-threonine ammonia-lyase activity as for Cha1p. In addition, the expression "the original function is maintained" regarding Cka2p may also mean that a variant of the protein has a property that a reduced activity thereof results in a reduced ceramide synthase activity. In addition, the expression "the original function is maintained" regarding Orm2p may also mean that a variant of the protein has a property that a reduced activity thereof results in an increased serine palmitoyltransferase activity. In cases where a target protein functions as a complex consisting of a plurality of subunits, the expression "the original function is maintained" regarding the target protein may also mean that a variant of the protein exhibits the corresponding function such as activity and property exemplified above in combination with other appropriate subunit(s). That is, for example, the expression "the original function is maintained" regarding Lcb1p may also mean that a variant protein has serine palmitoyltransferase activity in combination with an appropriate Lcb2p, and the expression "the original function is maintained" regarding Lcb2p may also mean that a variant protein has serine palmitoyltransferase activity in combination with an appropriate Lcb1p.

Hereafter, conservative variants will be exemplified.

Homologues of the genes exemplified above or homologues of the proteins exemplified above can easily be obtained from a public database by, for example, BLAST search or FASTA search using the nucleotide sequence of any of the genes exemplified above or the amino acid sequence of any of the proteins exemplified above as a query sequence. Furthermore, homologues of the genes exemplified above can be obtained by, for example, PCR using the chromosome of an organism such as yeast as the template, and oligonucleotides prepared on the basis of the nucleotide sequence of any of the genes exemplified above as primers.

The target genes each may be a gene encoding a protein having any of the aforementioned amino acid sequences but including substitution, deletion, insertion, and/or addition of one or several amino acid residues at one or several positions, so long as the original function is maintained. For example, the encoded protein may have an extended or deleted N-terminus and/or C-terminus. Although the number meant by the term "one or several" used above may differ depending on the positions of amino acid residues in the three-dimensional structure of the protein or the types of amino acid residues, specifically, it is, for example, 1 to 50, 1 to 40, or 1 to 30, preferably 1 to 20, more preferably 1 to 10, still more preferably 1 to 5, particularly preferably 1 to 3.

The aforementioned substitution, deletion, insertion, and/or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation due to an individual difference, or a difference of species of the organism from which the gene is derived (mutant or variant).

Furthermore, the target genes each may be a gene encoding a protein showing a homology of 80% or more, preferably 90% or more, more preferably 95% or more, still more preferably 97% or more, particularly preferably 99% or more, to any of the total amino acid sequence mentioned above, so long as the original function is maintained. In addition, in this specification, "homology" means "identity".

Furthermore, the target genes each may be a DNA that is able to hybridize under stringent conditions with a probe that can be prepared from any of the aforementioned nucleotide sequences, such as a sequence complementary to the whole sequence or a partial sequence of any of the aforementioned nucleotide sequences, so long as the original function is maintained. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing the nucleotide sequence as a template. As the probe, for example, a DNA fragment having a length of about 300 bp can be used. When a DNA fragment having a length of about 300 bp is used as the probe, in particular, the washing conditions of the hybridization may be, for example, 50° C., 2×SSC and 0.1% SDS.

Further, the target genes each may be a gene having any of the aforementioned nucleotide sequences in which an arbitrary codon is replaced with an equivalent codon. For example, the target genes each may be a gene modified so that it has optimal codons according to codon frequencies in a host to be used.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

<1-2> Methods for Increasing Activity of Protein

Hereafter, methods for increasing the activity of a protein will be explained.

The expression "the activity of a protein is increased" means that the activity of the protein per cell is increased as compared with that of a non-modified strain. The term "non-modified strain" may refer to a reference strain that has not been modified so that the activity of an objective protein is increased. Examples of the non-modified strain include a wild-type strain and parent strain. The state that "the activity of a protein is increased" may also be expressed as "the activity of a protein is enhanced". Specifically, the expression "the activity of a protein is increased" means that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) coding for the protein, or the translation amount of the protein (i.e. the amount of the protein). Although the degree of the increase in the activity of a protein is not particularly limited so long as the activity of the protein is increased as compared with that of a non-modified strain, the activity of the protein may be increased 1.5 times or more, 2 times or more, or 3 times or more, as compared with that of a non-modified strain. Further, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Further, so long as the activity of the protein is eventually increased, the activity of an objective protein inherently contained in a host may be attenuated and/or eliminated, and then an appropriate type of the objective protein may be introduced thereto.

The modification for increasing the activity of a protein is attained by, for example, increasing the expression of a gene coding for the protein. The expression "the expression of a gene is increased" means that the expression amount of the gene per cell is increased as compared with that of a non-modified strain such as a wild-type strain and parent strain. The expression "the expression of a gene is increased" may specifically mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The expression of a gene may be increased 1.5 times or more, 2 times or more, or 3 times or more, as compared with that observed in a non-modified strain. Further, the state that "the expression of a gene is increased" includes not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include autonomously replicating sequences (ARS) consisting of a specific short repeated sequence, and rDNA sequences present in about 150 copies on the chromosome. WO95/32289 discloses an example where gene recombination was performed in yeast by using homologous recombination. In addition, a gene can also be introduced into a chromosome by, for example, integrating the gene into a transposon and transferring the transposon to the chromosome.

Introduction of an objective gene into a chromosome can be confirmed by Southern hybridization using a probe having a sequence complementary to the whole or a part of the gene, PCR using primers prepared on the basis of the sequence of the gene, or the like.

Further, the copy number of an objective gene can also be increased by introducing a vector including the gene into a host. For example, the copy number of an objective gene can be increased by ligating a DNA fragment including the objective gene with a vector that functions in a host to construct an expression vector of the gene, and by transforming the host with the expression vector. The DNA fragment including the objective gene can be obtained by, for example, PCR using the genomic DNA of a microorganism having the objective gene as the template. As the vector, a vector autonomously replicable in the cell of the host can be used. The vector may be a single copy vector or may be a multi-copy vector. Further, the vector preferably includes a marker for selection of transformant. Examples of the marker include antibiotic resistance genes such as KanMX, NatMX (nat1), and HygMX (hph) genes, and genes complimenting auxotrophy such as LEU2, HIS3, and URA3 genes. Examples of vector autonomously replicable in yeast include plasmids having a CEN4 replication origin and plasmids having a 2 μm DNA replication origin. Specific examples of vector autonomously replicable in yeast include pAUR123 (TAKARA BIO) and pYES2 (Invitrogen).

When a gene is introduced, it is sufficient that the gene is expressibly harbored by the yeast of the present invention. Specifically, it is sufficient that the gene is introduced so that it is expressed under the control of a promoter sequence that functions in the yeast of the present invention. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator can be located downstream the gene. The terminator is not particularly limited as long as a terminator that functions in the yeast of the present invention is chosen. The terminator may be a terminator derived from the host, or a heterogenous terminator. The terminator may be the native terminator of the gene to be introduced, or a terminator of another gene. Examples of the terminator that functions in the yeast of the present invention include CYC1, ADH1, ADH2, ENO2, PG/1, and TDH1 terminators.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Further, when two or more kinds of genes are introduced, it is sufficient that the genes each are expressibly harbored by the yeast of the present invention. For example, all the genes may be carried by a single expression vector or a chromosome. Alternatively, the genes may be separately carried by two or more expression vectors, or separately carried by a single or two or more expression vectors and a chromosome. An operon constituted by two or more genes may also be introduced.

The gene to be introduced is not particularly limited so long as it codes for a protein that functions in the host. The gene to be introduced may be a gene derived from the host, or may be a heterogenous gene. The gene to be introduced can be obtained by, for example, PCR using primers designed on the basis of the nucleotide sequence of the gene and the genomic DNA of an organism having the gene or a plasmid carrying the gene as a template. The gene to be introduced may also be totally synthesized, for example, on the basis of the nucleotide sequence of the gene (Gene, 60(1), 115-127 (1987)). The obtained gene can be used as it is, or after being modified as required.

Further, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene, such as a promoter. Expression control sequences can be identified by using a promoter search vector or gene analysis software such as GENETYX.

The transcription efficiency of a gene can be improved by, for example, replacing the promoter of the gene on a chromosome with a stronger promoter. The "stronger promoter" means a promoter providing an improved transcription of a gene as compared with an inherently existing wild-type promoter of the gene. Examples of stronger promoters usable in yeast include PGK1, PGK2, PDC1, TDH3, TEF1, TEF2, TPI1, HXT7, ADH1, GPD1, and KEX2 promoters. Further, as the stronger promoter, a highly-active type of an existing promoter may also be obtained by using various reporter genes.

The translation efficiency of a gene can also be improved by, for example, modifying codons. For example, in the case of heterogenous expression of a gene or the like, the translation efficiency of the gene can be improved by replacing a rare codon present in the gene with a more frequently used synonymous codon. That is, a gene to be introduced may have been modified, for example, so that it has optimal codons according to codon frequencies observed in the host to be used. Codons can be replaced by, for example, the site-specific mutation method for introducing an objective mutation into an objective site of DNA. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Further, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Further, the modification that increases the activity of an enzyme can also be attained by, for example, enhancing the specific activity of the enzyme. An enzyme showing an enhanced specific activity can be obtained by, for example, searching various organisms. Further, a highly-active type of an existing enzyme may also be obtained by introducing a mutation into the existing enzyme. Enhancement of the specific activity may be independently used, or may be used in an arbitrary combination with such methods for enhancing the gene expression as mentioned above.

The method for transformation is not particularly limited, and methods conventionally used for transformation of yeast can be used. Examples of such methods include protoplast method, KU method (H.Ito et al., J. Bateriol., 153-163 (1983)), KUR method (Fermentation and industry, vol. 43, p.630-637 (1985)), electroporation method (Luis et al., FEMS Micro biology Letters 165 (1998) 335-340), and a method using a carrier DNA (Gietz R. D. and Schiestl R. H., Methods Mol. Cell. Biol. 5:255-269 (1995)). Methods for manipulating yeast such as methods for spore-forming and methods for isolating haploid yeast are disclosed in Chemistry and Biology, Experimental Line 31, Experimental Techniques for Yeast, 1st Edition, Hirokawa-Shoten; Bio-Manual Series 10, Genetic Experimental Methods for Yeast, 1st Edition, Yodosha; and so forth.

An increase in the activity of a protein can be confirmed by measuring the activity of the protein.

An increase in the activity of a protein can also be confirmed by confirming an increase in the expression of a gene coding for the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that observed in a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

<1-3> Method for Reducing Activity of Protein

Hereafter, methods for reducing the activity of a protein will be explained.

The expression "the activity of a protein is reduced" means that the activity of the protein per cell is reduced as compared with that of a non-modified strain. The term "non-modified strain" may refer to a reference strain that has not been modified so that the activity of an objective protein is reduced. Examples of the non-modified strain include a wild-type strain or parent strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) coding for the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule completely disappears. Although the degree of the reduction in the activity of a protein is not particularly limited so long as the activity is reduced as compared with that of a non-modified strain, it may be reduced to, for example, 50% or less, 20% or less, 10% or less, 5% or less, or 0% of that of a non-modified strain.

The modification for reducing the activity of a protein can be attained by, for example, reducing the expression of a gene coding for the protein. The expression "the expression of a gene is reduced" means that the expression of the gene per cell is reduced as compared with that of a non-modified strain such as a wild-type strain and parent strain. The expression "the expression of a gene is reduced" may specifically mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter. When an expression control sequence is modified, preferably one or more nucleotides, more preferably two or more nucleotides, particularly preferably three or more nucleotides, of the expression control sequence are modified. Further, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Further, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Further, for example, the gene expression may be reduced due to disruption of a gene as described later.

The modification for reducing the activity of a protein can also be attained by, for example, disrupting a gene coding for the protein. The expression "a gene is disrupted" means that a gene is modified so that a protein that can normally function is not produced. The expression "a protein that can normally function is not produced" encompasses cases where no protein is expressed from the gene at all and cases where a protein of which the function (such as activity and property) has been reduced or completely eliminated is expressed from the gene.

Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Further, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, using a recombinant DNA. The structure of the recombinant DNA to be used for homologous recombination is not particularly limited as long as it causes homologous recombination in a desired manner. For example, a host can be transformed with a linear DNA comprising an arbitrary sequence such as a deficient type gene or any appropriate insertion sequence, which arbitrary sequence is flanked with upstream and downstream sequences of the homologous recombination target region on the chromosome, so that homologous recombination can occur at upstream and downstream sides of the target region, to thereby replace the target region with the arbitrary sequence. Specifically, such modification of a gene on a chromosome as described above can be attained by, for example, preparing a deficient type gene modified so that it cannot produce a protein that can normally function, and transforming a host with a recombinant DNA including the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easy. Examples of the deficient type gene include a gene in which a part or whole of the gene is deleted, a gene introduced with missense mutation, a gene introduced with an insertion sequence such as a transposon and a marker gene, a gene introduced with nonsense mutation, and a gene introduced with frameshift mutation. The protein encoded by the deficient type gene has a conformation different from that of the wild-type protein, even if it is produced, and thus the function thereof is reduced or eliminated.

The modification for reducing the activity of a protein can also be attained by, for example, a mutagenesis treatment. Examples of the mutagenesis treatment include usual mutation treatments such as irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

A reduction in the activity of a protein can be confirmed by measuring the activity of the protein.

A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA include Northern hybridization, RT-PCR, and so forth (Molecular Cloning, Cold spring Harbor Laboratory Press, Cold Spring Harbor (USA), 2001). The amount of mRNA is preferably reduced to, for example, 50% or less, 20% or less, 10% or less, 5% or less, or 0%, of that observed in a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably reduced to, for example, 50% or less, 20% or less, 10% or less, 5% or less, or 0%, of that observed in a non-modified strain.

Disruption of a gene can be confirmed by determining nucleotide sequence of a part or the whole of the gene, restriction enzyme map, full length, or the like of the gene depending on the means used for the disruption.

<2> Method for Producing Objective Substance of the Present Invention

The method of the present invention is a method for producing an objective substance comprising cultivating the yeast of the present invention in a culture medium, and collecting the objective substance from cells of the yeast and/or the culture medium. In the method of the present invention, a single kind of objective substance may be produced, or two or more kinds of objective substances may be produced.

The medium to be used is not particularly limited, so long as the yeast of the present invention can proliferate in it, and an objective substance can be produced. As the medium, for example, a usual medium used for cultivating yeast can be used. Examples of such a medium include SD medium, SG medium, SDTE medium, and YPD medium. The medium may contain carbon source, nitrogen source, phosphorus source, and sulfur source, as well as components selected from other various organic components and inorganic components as required. The types and concentrations of the medium components can be appropriately determined according to various conditions such as the type of the yeast to be used and the type of the objective substance to be produced.

The culture medium may contain an additive that is able to associate with, bind to, solubilize, and/or capture the objective substance. Use of the additive may result in an increased production of the objective substance. That is, the amount produced of the objective substance by the yeast of the present invention may be increased in the presence of the additive as compared with in the absence of the additive. Use of the additive may specifically result in an increased production of the objective substance in the culture medium. The production of the objective substance in the culture medium may also be referred to as "excretion of the objective substance". The expression "associating with, binding to, solubilizing, and/or capturing an objective substance" may specifically mean increasing the solubility of the objective substance into the culture medium. Examples of the additive include cyclodextrins and zeolites. The number of glucose residues constituting cyclodextrins is not particularly limited, and it may be, for example, 5, 6, 7, or 8. That is, examples of cyclodextrins include cyclodextrin consisting of 5 glucose residues, alpha-cyclodextrin, beta-cyclodextrin, gamma-cyclodextrin, and derivatives thereof. Examples of cyclodextrin derivatives include cyclodextrins into which one or more functional groups have been introduced. The type, number, and amount of the functional group, and the position to which the functional group is introduced are not particularly limited as long as the derivative is able to associate with, bind to, solubilize, and/or capture the objective substance. The functional group may be introduced to, for example, hydroxyl group of C2, C3, C6, or a combination thereof, which may result in an increased solubility of cyclodextrin itself. Examples of the functional group include alkyl groups and hydroxyalkyl groups. The alkyl groups and hydroxyalkyl groups each may have a linear alkyl chain or may have a branched alkyl chain. The alkyl groups and hydroxyalkyl groups each may have a carbon number of, for example, 1, 2, 3, 4, or 5. Specific examples of the alkyl groups include methyl, ethyl, propyl, butyl, pentyl, isopropyl, and isobutyl groups. Specific examples of the hydroxyalkyl groups include hydroxymethyl, hydroxyethyl, hydroxypropyl, hydroxybutyl, hydroxypentyl, hydroxyisopropyl, and hydroxyisobutyl groups. Specific examples of cyclodextrin derivatives include methyl-alpha-cyclodextrin, methyl-beta-cyclodextrin, hydroxypropyl-alpha-cyclodextrin such as 2-hydroxypropyl-alpha-cyclodextrin, and hydroxypropyl-beta-cyclodextrin such as 2-hydroxypropyl-beta-cyclodextrin. The types of zeolites are not particularly limited. As the additive, a single kind of additive may be used, or two or more kinds of additives may be used in combination.

The additive may be contained in the medium during the whole period of the culture, or may be contained in the medium during only a part of the culture period. For example, the additive may be or may not be contained in the medium from the start of the culture. When the additive is not contained in the medium at the time of the start of the culture, the additive is supplied to the medium after the start of the culture. Timing of the supply can be appropriately determined according to various conditions such as the length of culture period. For example, the additive may be supplied to the medium after the yeast of the present invention fully grows. Further, in any case, the additive may be additionally supplied to the medium as required. Means for supplying the additive to the medium is not particularly limited. For example, the additive can be supplied to the medium by feeding a feed medium containing the additive to the medium. The concentration of the additive in the medium is not particularly limited so long as the objective substance can be produced. For example, the concentration of the additive in the medium may be 0.1 g/L or higher, 1 g/L or higher, 2 g/L or higher, 5 g/L or higher, or 10 g/L or higher, may be 200 g/L or lower, 100 g/L or lower, 50 g/L or lower, or 20 g/L or lower, or may be within a range defined with a combination thereof. The concentration of the additive in the medium may be, for example, 0.1 g/L to 200 g/L, 1 g/L to 100 g/L, or 5 g/L to 50 g/L. The additive may be or may not be contained in the medium at a concentration within the range exemplified above during the whole period of the culture. For example, the additive may be contained in the medium at a concentration within the range exemplified above at the start of the culture, or it may be supplied to the medium so that a concentration within the range exemplified above is attained after the start of the culture.

Specific examples of the carbon source include, for example, saccharides such as glucose, fructose, sucrose, lactose, galactose, xylose, arabinose, blackstrap molasses, starch hydrolysates, and hydrolysates of biomass, organic acids such as acetic acid, fumaric acid, citric acid, and succinic acid, alcohols such as glycerol, crude glycerol, and ethanol, and aliphatic acids. As the carbon source, a single kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Further, when an auxotrophic mutant that requires an amino acid, a nucleic acid, or the like for growth thereof is used, it is preferable to supplement a required nutrient to the medium.

The culture conditions are not particularly limited so long as the yeast of the present invention can proliferate, and the objective substance can be produced. The culture can be performed, for example, under usual conditions used for cultivating yeast. The culture conditions can be appropriately determined according to various conditions such as the type of yeast to be used and the type of objective substance to be produced.

The culture can be performed by using a liquid medium under an aerobic condition, a microaerobic condition, or an anaerobic condition. The culture can preferably be performed under an aerobic condition. The term "aerobic condition" may refer to a condition where the dissolved oxygen concentration in the liquid medium is 0.33 ppm or higher, or preferably 1.5 ppm or higher. In cases of the aerobic condition, the oxygen concentration can be controlled to be, for example, 5 to 50%, preferably about 10 to 20%, of the saturated oxygen concentration. Specifically, the aerobic culture can be performed with aeration or shaking. The term "microaerobic condition" may refer to a condition where oxygen is supplied to the culture system but the dissolved oxygen concentration in the liquid medium is lower than 0.33 ppm. The term "anaerobic condition" may refer to a condition where oxygen is not supplied to the culture system. The culture temperature may be, for example, 25 to 35° C., preferably 27 to 33° C., more preferably 28 to 32° C. pH of the medium may be, for example, 3 to 10, or 4 to 8. pH of the medium may be adjusted as required during the culture. For adjusting pH, inorganic or organic acidic or alkaline substances, such as ammonia gas and so forth, can be used. The culture period may be, for example, 10 to 200 hours, or 15 to 120 hours. The culture condition may be constant during the whole period of the culture, or may be changed during the culture. The culture can be performed as batch culture, fed-batch culture, continuous culture, or a combination of these. Further, the culture may be performed as two steps of a seed culture and a main culture. In such a case, the culture conditions of the seed culture and the main culture may or may not be the same. For example, both the seed culture and the main culture may be performed as batch culture. Alternatively, for example, the seed culture may be performed as batch culture, and the main culture may be performed as fed-batch culture or continuous culture.

By culturing the yeast of the present invention under such conditions, the objective substance is accumulated in the medium and/or cells of the yeast.

Production of the objective substance can be confirmed by known methods used for detection or identification of compounds. Examples of such methods include, for example, HPLC, UPLC, LC/MS, GC/MS, and NMR. These methods may be used independently or in any appropriate combination.

The produced objective substance can be collected by known methods used for separation and purification of compounds. Examples of such methods include, for example, ion-exchange resin method, membrane treatment, precipitation, and crystallization. These methods may be used independently or in any appropriate combination. When the objective substance accumulates in cells, the cells can be disrupted with, for example, ultrasonic waves or the like, and then the objective substance can be collected from the supernatant obtained by removing the cells from the cell-disrupted suspension by centrifugation. The objective substance to be collected may be a free compound, a salt thereof, or a mixture thereof.

Further, when the objective substance deposits in the medium, it can be collected by centrifugation, filtration, or the like. The objective substance deposited in the medium may also be isolated together with the objective substance dissolved in the medium after the objective substance dissolved in the medium is crystallized.

The objective substance collected may contain yeast cells, medium components, moisture, and by-product metabolites of the yeast, in addition to the objective substance. The purity of the objective substance collected may be, for example, 50% (w/w) or higher, preferably 85% (w/w) or higher, particularly preferably 95% (w/w) or higher.

The objective substance such as phytosphingosine (PHS) and sphinganine (DHS) may be converted to a corresponding sphingolipid such as phytoceramides (PHC) and dihydroceramides (DHC) by chemical reaction of mixture of sphingoid base (PHS/DHS) and a fatty acid (J. Biol. Chem. July 2002 277 (29): 25847-5).

EXAMPLES

The present invention will be more specifically explained with reference to the following examples. However, these examples should not be construed to limit the present invention in any meanings.

Example 1: Construction of Strains

*S. cerevisiae* strain EVST20240, the most developed PHS producer strain, was derived from strain NCYC 3608 of the National Collection of Yeast Cultures. Strain NCYC 3608 (genotype MATalpha gal2 ho::HygMX ura3::KanMX) is a Mat a derivative of S288C. Strain EVST20240 contains following modifications, namely the deletions of his3Δ0 leu2Δ0 ura3Δ0 Δcha1::LoxP Δcka2::LoxP Δlcb4::LoxP Δlcb5::LoxP Δorm2::LoxP CAT5-91Met gal2 ho YNRCΔ9:: ScLCB1/ScSUR2 YPRCΔ15::ScLCB2/ScTSC10 [ARS/CEN/URA/ScTSC10/ScSUR2] [ARS/CEN/HIS/ScLCB1/ScLCB2] [ARS/CEN/LEU]. Strain EVST20240 can be manipulated using standard genetic methods and can be used as a regular diploid or haploid yeast strain. The construction of strain EVST20240 is described below in detail.

S. cerevisiae strain EYS4769 was generated from strain NCYC 3608. The first step consisted of removing the HygMX selection marker left from the deletion of the HO gene. For this, a plasmid pEVE3195 was constructed containing a module consisting of a region homologous to the HygMX promoter immediately upstream of the HygMX start codon, followed by Kluyveromyces lactis URA3 gene flanked by loxP sites, and a region homologous to the HygMX terminator immediately downstream of the stop codon. This module was flanked by two AscI restriction sites and was released by AscI digestion, then the released fragment was used to transform strain S288C. Consequently, the HygMX marker was replaced by this module including the K. lactis URA3 selection marker. Last, the URA3 marker was removed via spontaneous recombination of the loxP sequences. Clones without URA3 were selected first in SC liquid medium and then on plates containing 1 g/L 5'-fluoroorotic acid (5-FOA) medium (1.926 g/L SC mixture (SC-mix) without uracil, 30 mg/L uracil, 6.7 g/L yeast nitrogen base, 20 g/L glucose, pH 5.8) (for complete SC mixture, see Table 15), which is converted into a toxic compound by yeasts with an active URA3 gene.

Removal of the KanMX selection marker, of the loxP scar left by the HygMX marker removal, and deletion of the LEU2 and HIS3 genes was achieved using a PCR-mediated seamless gene deletion strategy, as follows.

For deletion of the KanMX selection marker a plasmid pEVE3622 was constructed containing a module consisting of a region homologous to the KanMX promoter immediately upstream of the KanMX start codon, and a region homologous to the KanMX terminator immediately downstream of the stop codon, followed by a Kluyveromyces lactis URA3 gene. In the first step, a plasmid pEVE3191 was generated by introducing a DNA fragment A into vector pEVE1915 via the restriction site AscI. The DNA fragment A was prepared by overlap PCR. That is, two DNA fragments were amplified by PCR using genomic DNA of strain NCYC 3608 as the template and primer pairs EV3964/EV3965 and EV3966/EV3967. These two DNA fragments were then joined by PCR using primer pair EV3964/EV3967 to obtain the DNA fragment A. In the next step, the Kluyveromyces lactis URA3 gene was PCR amplified from pEVE3195 with primer pair EVPR11045/EVPR11046 and cloned into the EcoRV linearized plasmid pEVE3191 by In-Fusion cloning, generating plasmid pEVE3622. A NdeI restriction site in the downstream homologous region was used for restriction digestion of the plasmid, followed by genomic integration and selection in SC medium without uracil (1.926 g/L SC-mix without uracil, 6.7 g/L yeast nitrogen base, 20 g/L glucose, pH 5.8) (for complete SC mixture, see Table 15). Next, clones without URA3 marker were selected on plates containing 1 g/L 5-fluoroorotic acid (5-FOA) agar plates. A mixed population of clones with the wild-type genotype and the desired deletions was obtained, and identification of the deletion mutants was done by PCR.

For the removal of the loxP scar, and the deletion of the LEU2 and HIS3 genes, the same method was used. Primer pairs EV3970/EV3971, EV3972/EV3973, and EV3970/EV3973 were used to generate the targeting fragment for deletion of the open reading frame of the HIS3 gene. Primer pairs EV3976/EV3977, EV3978/EV3979, and EV3976/EV3979 were used to generate the targeting fragment for deletion of the open reading frame of the LEU2 gene. The plasmid to target the loxP scar (pEVE3621) was linearized with Pm/I in the downstream integration tag; the plasmid to target the LEU2 marker (pEVE3624) was linearized with BseRI in the downstream integration tag; for the plasmid to target the HIS3 marker (pEVE3623), a unique restriction site HindIII was introduced by site-directed mutagenesis in the upstream integration tag generating pEVE3763, and digested with HindIII. Following the genomic integration and selection in SC medium without uracil, clones without URA3 marker were selected on agar plates containing 1 g/L 5-FOA. A mixed population of clones with the wild-type genotype and the desired deletions was obtained, and identification of the deletion mutants was done by PCR.

S. cerevisiae strain EYS4789 was generated from the previously described strain EYS4769 by deletion of the LCB4 gene. This was done by a PCR-based gene deletion strategy generating a start-to-stop-codon deletion of the open reading frame. LCB4 gene was replaced by a deletion construct comprised of the nourseothricin resistance gene NatMX (nat1) flanked by loxP sites, and sequences homologous to the native promoter and terminator of the LCB4 gene that were added by PCR using primers EV4024 and EV4025 (Table 9). Transformants were selected on SC-agar plates containing 100 mg/L nourseothricin. Clones were verified by PCR testing for proper insertion of the deletion construct.

S. cerevisiae strains EYS4839, EYS4840, and EYS4845 were generated from the previously described strain EYS4789 by first removing the previously inserted NatMX selection marker as follows: strain EYS4789 was transformed with the URA3 selectable plasmid pEVE0078 containing an expression cassette for the Cre recombinase enzyme. Cre recombinase catalyzes site specific recombination between the two loxP sites flanking the NatMX marker with concomitant removal of the same. Clones expressing the Cre recombinase were selected on SC-agar plates without uracil. A few clones were picked and tested for the loss of the selection marker by plating on the respective selective plates. The Cre recombinase bearing plasmid was removed by growing strains in the presence of 1 g/L 5'-fluoroorotic acid which is converted into a toxic compound by the activity of the URA3 gene encoded enzyme. Only clones that had lost the plasmid were able to grow on 5-FOA-containing medium. One positive clone resulted in strain EYS4964.

S. cerevisiae strain EYS4964 was used for deletion of the ORM2, LCB5, and ELO3 genes to construct strains EYS4839, EYS4840, and EYS4845. Strain EYS4839 lacks the ORM2 gene, strain EYS4840 lacks the LCB5 gene, and strain EYS4845 lacks the ELO3 gene. This was done by a PCR-based gene deletion strategy generating a start-to-stop-codon deletion of the open reading frame. ORM2, LCB5, and ELO3 genes were replaced by respective deletion constructs comprised of the nourseothricin resistance gene NatMX (nat1) flanked by loxP sites, and sequences homologous to the native promoter and terminator of the ORM2, LCB5, and ELO3 genes that were added by PCR using primer pairs EV4215/EV4216, EV4030/EV4031, and EV5103/EV5104, respectively. Transformants were selected on SC-agar plates containing 100 mg/L nourseothricin. Clones were verified by PCR testing for proper insertion of the deletion construct.

S. cerevisiae strain EYS5009 was derived from the previously described strain EYS4789 by deletion of the CKA2 gene. This was done by a PCR-based gene deletion strategy generating a start-to-stop-codon deletion of the open reading frame. The CKA2 gene was replaced by a deletion construct comprised of the hygromycin resistance gene HygMX (hph) flanked by loxP sites, and sequences homologous to the native promoter and terminator of the CKA2 gene that were added by PCR using primers EV4740 and EV4741 (Table 9). Transformants were selected on SC-agar plates containing 300 mg/L hygromycin. Clones were verified by PCR testing for proper insertion of the deletion construct. In a second step, the previously inserted selection markers were removed by transformation with pEVE0078, a URA3 selectable plasmid containing an expression cassette for the Cre recombinase enzyme. Cre recombinase catalyzes site specific recombination between two loxP sites flanking the HygMX (hph) marker with concomitant removal of the same. Clones expressing the Cre recombinase were selected on SC-agar plates without uracil. A few clones were picked and tested for the loss of the selection marker by plating on the respective selective plates. The Cre recombinase bearing plasmid pEVE0078 was removed by growing strains in the presence of 1 g/L 5'-fluoroorotic acid which is converted into a toxic compound by the activity of the URA3 gene encoded enzyme. Only clones that have lost the plasmid were able to grow on SC medium containing 5-FOA.

S. cerevisiae strain EYS5066 derived from the previously described strain EYS5009 by deletion of the LCB5 gene. This was done by a PCR-based gene deletion strategy generating a start-to-stop-codon deletion of the open reading frame. The LCB5 gene was replaced by a deletion construct comprised of the nourseothricin resistance gene NatMX (nat1) flanked by loxP sites, and sequences homologous to the native promoter and terminator of the LCB5 gene that were added by PCR using primers EV4030 and EV4031 (Table 9). Transformants were selected on SC-agar plates containing 100 mg/ml nourseothricin. Clones were verified by PCR testing for proper insertion of the deletion construct.

S. cerevisiae strain EYS5175 derived from the previously described strain EYS5066 by deletion of the ORM2 gene. This was done by a PCR-based gene deletion strategy generating a start-to-stop-codon deletion of the open reading frame. The ORM2 gene was replaced by a deletion construct comprised of the hygromycin resistance gene HygMX (hph) flanked by loxP sites, and sequences homologous to the native promoter and terminator of the ORM2 gene that were added by PCR using primers EV4215 and EV4216 (Table 9). Transformants were selected on SC-agar plates containing 100 mg/L hygromycin. Clones were verified by PCR testing for proper insertion of the deletion construct.

S. cerevisiae strain EVST20057 was generated from the previously described strain EYS5175 by deletion of the CHA1 gene by a PCR-based gene deletion strategy generating a start-to-stop-codon deletion of the open reading frame. The CHA1 gene was replaced by a deletion construct comprised of the KanMX gene that confers resistance to the aminoglycoside antibiotic G418 flanked by loxP sites, and sequences homologous to the native promoter and terminator of the CHA1 gene that were added by PCR using primers EV3782 and EV3783 (Table 9). Transformants were selected on SC-agar plates containing 100 mg/L G418. Clones were verified by PCR testing for proper insertion of the deletion construct. Additionally, the resistance markers NatMX, HygMX (Hph), and KanMX previously used to delete the LCB5, ORM2, and CHA1 genes, respectively, were removed from EYS5175 by transformation with pEVE0078, a URA3 selectable plasmid containing an expression cassette for the Cre recombinase. Cre recombinase catalyzes site specific recombination between two loxP sites flanking the above mentioned markers with concomitant removal of the same. Clones expressing the Cre recombinase were selected on SC-agar plates without uracil. A few clones were picked and tested for the loss of the selection markers by plating on the respective selective plates. The plasmid pEVE0078 bearing the Cre recombinase was removed by growing strains in the presence of 1 g/L 5'-fluoroorotic acid which is converted into a toxic compound by the activity of the URA3 gene encoded enzyme. Only clones that had lost the plasmid were able to grow on medium containing uracil.

S. cerevisiae strain EVST20160 was generated from the previously described strain EVST20057 by integration into the genomic Ty1 long terminal repeat YNRCΔ9 (Chromosome XIV 727363-727661) an expression module consisting of two native S. cerevisiae LCB1 and SUR2 genes and the selectable marker NatMX. LCB1 and SUR2 genes were expressed from native S. cerevisiae GPD1 and TEF2 promoters (Table 13), respectively, followed by native S. cerevisiae CYC1 and PGI1 terminators (Table 14). In addition, a second integration module expressing two native S. cerevisiae LCB2 and TSC10 genes and the selectable marker HygMX (Hph) was integrated into the genomic Ty1 long-terminal repeat YPRCΔ15(Chromosome XVI 776667 . . . 776796. LCB2 and TSC10 genes were expressed from native S. cerevisiae PGK1 and TPI1 promoters (Table 13), respectively, followed by native S. cerevisiae ADH2 and TDH1 terminators (Table 14).

S. cerevisiae strain EVST20240 was generated from the previously described strain EVST20160 by transformation with three plasmids. Plasmid 1 (pEVE4932) contained a double expression cassette with the open reading frame of the S. cerevisiae LCB1 gene flanked by a native S. cerevisiae TEF1 promoter and a native S. cerevisiae ADH1 terminator, and the open reading frame of the S. cerevisiae LCB2 gene flanked by a native S. cerevisiae PGK1 promoter and a native S. cerevisiae CYC1 terminator. Plasmid 2 (pEV22325) contained a double expression cassette with the open reading frame of the S. cerevisiae TSC10 gene flanked by a native S. cerevisiae TEF1 promoter (Table 13) and a native S. cerevisiae ADH1 terminator (Table 14), and the open reading frame of the S. cerevisiae SUR2 gene flanked by a native S. cerevisiae PGK1 promoter and a native S. cerevisiae CYC1 terminator. Plasmid 3 (pEVE2159) contained an empty expression cassette with only a native S. cerevisiae PGK2 promoter and a native S. cerevisiae ADH2 terminator without open reading frame. This plasmid was solely used to render the strain prototrophic for leucine. Transformants harboring all three plasmids were selected on agarose plates without the amino acids histidine and leucine and the pyrimidine base uracil via the selection markers HIS3, URA3, and LEU2 that were present on plasmids 1, 2 or 3, respectively.

Example 2: Cultivation of Strains in Small Scale Batch Culture and Analysis for PHS Production Yeast strains (FIG. 1) were streaked as patches on selective SC-agar plates lacking leucine, histidine, and uracil. After overnight growth, 1 ml pre-cultures in 14 ml round bottom tubes were set up by inoculation of SC-medium lacking leucine, histidine, and uracil (1.546 g/L SC-mix without leucine, histidine, uracil, 6.7 g/L yeast nitrogen base, 20 g/L glucose, pH 5.8) (for complete SC mixture, see Table 15). The pre-cultures were cultivated at 30° C. with shaking for 24h and were then used for inoculation of main cultures in 96-well deep well plates at an $OD_{600}$ of 0.1 in SC-medium lacking leucine, histidine, and uracil and containing 20 g/L glucose and 10 g/L alpha-cyclodextrin. After 48h of incubation at 30° C. with shaking, the cultures were harvested by centrifugation (5 min, 4000 rpm) and an aliquot of the supernatant was taken for sphingolipid analysis. The samples were diluted in methanol so that the concentration of analytes was within the calibration range. The stock solutions were prepared as outlined in Table 1.

TABLE 1

Stock solutions of standards

| Compound | Supplier | Product N. | Solvent | Concentration |
|---|---|---|---|---|
| 3-ketosphinganine | Larodan Fine Chemicals AB | 56-1312-5 | DMSO | 1 g/L |
| C18-Phytosphingosine | Santa Cruz Biotechnology | Sc-201385 | DMSO | 1 g/L |
| Sphinganine | AVANTI Polar Lipids Inc | 860498P | DMSO | 1 g/L |

A series of calibration solutions at 4 mg/L, 2 mg/L, 1 mg/L, 0.5 mg/L, 0.25 mg/L, 0.125 mg/L, 62.5 µg/L and 31.25 µg/L in methanol was prepared from the stock solutions and injected into the UPLC-TOF. The LC-MS/MS method was as follows: Mobile Phase A: 2 mM ammonium formate in water+0.2% formic acid; Mobile Phase B: 1 mM ammonium formate in acetonitrile/methanol 1:1+0.2% formic acid; Column: Acquity BEH UPLC C8, 2.1×100 mm, 1.7 µm. The elution gradient is shown in Table 2 and the LC-MS/MS conditions are given in Table 3. Table 4 shows the mass spectrometer source and detector parameters. Masses and retention times of standard compounds can be found in Table 5. Concentrations of 3-ketosphinganine, C18-phytosphingosine, and sphinganine were calculated according to their respective calibration curve, whereas concentrations of C20-phytosphingosine, C18:1-phytosphingosine, and C20:1-phytosphingosine were estimated using C18-phytosphingosine calibration curve and C18-phytosphingosine-adduct and C20-phytosphingosine-adduct were calculated according to C18-phytosphingosine and applying a correlation factor of 0.59.

TABLE 2

Gradient for separation of sphingolipids

| Time | % B |
|---|---|
| 0 | 50 |
| 1 | 85 |
| 4 | 100 |
| 4.7 | 100 |
| 4.8 | 50 |
| 5.5 | 50 |

TABLE 3

LC-MS/MS conditions

| | |
|---|---|
| Injection volume | 5 µl |
| Column Temperature | 50° C. ± 5° C. |
| Injection method | Partial loop |
| Auto sampler temperature | 30° C. ± 5° C. |
| Weak wash | 800 µl 1 mM ammonium formate in water/methanol 1:1 |
| Strong wash | 300 µl 2-propanol |
| Seal wash | 5 min with water/acetonitrile 9:1 |

TABLE 4

Mass spectrometer source and detector parameters

| Source Parameter | Value |
|---|---|
| Ion Source | Electrospray Positive Mode (ESI+) |
| Capillary Voltage | 4.5 kV |
| End Plate Offset | −500 V |
| Nebulizer Pressure | 1.6 Bar |
| Dry Gas N2 | 8.0 l/min |
| Dry Temperature | 180° C. |
| Hexapole Parameters | See below |
| Funnel 1 RF | 200 Vpp |
| Funnel 2 RF | 200 Vpp |
| ISCID Energy | 0 eV |
| Hexapole RF | 80 Vpp |
| Quadrupole Parameters | See below |
| Ion Energy | 4 eV |
| Low Mass | 100 m/z |
| Collision Cell Parameters | See below |
| Collision energy | 10 eV |
| Transfer Time | 70 us |
| Collision RF | 140 Vpp |
| Pre Puls Storage | 5 us |
| Acquisition Parameter | Value |
| Ion Polarity | positive |
| Mass Range | From 100 to 1400 m/z |
| Absolute Processing Threshold | 50 |
| Peak Summation Width | 5 pts |
| Calibration | Sodium Formate (ESI+) |

TABLE 5

Masses and retention times of standard compounds

| Compound | m/z | Ion | Retention time (min) |
|---|---|---|---|
| 3-ketosphinganine | 300.29 | [M − H]+ | 1.80 |
| Sphinganine | 302.31 | [M − H]+ | 1.79 |
| C18-Phytosphingosine | 318.30 | [M − H]+ | 1.71 |
| C20-Phytosphingosine | 346.30 | [M − H]+ | 2.04 |
| C18-Phytosphingosine-adduct | 344.30 | [M − H]+ | 2.03 |
| C20-Phytosphingosine-adduct | 372.30 | [M − H]+ | 2.28 |

Phytosphingosine and sphinganine production for double deletion strains EYS4839, EYS4840, EYS4845, and EYS5009 were measured in the supernatant of small scale yeast cultures. As shown in Table 6, Phytosphingosine and Sphinganine production increased in strains in all double deletion strains and were remarkably higher in the strains with LCB4/ELO3 or LCB4/CKA2 gene deletions.

TABLE 6

Phytosphingosine and Sphinganine titers in small scale cultures.

| Strain # | Gene Deletions | Phytosphingosine mg/L | Sphinganine mg/L |
|---|---|---|---|
| EYS4964 | none | 1.08 | 0.37 |
| EYS4839 | LCB4 ORM2 | 2.57 | 0.64 |
| EYS4840 | LCB4 LCB5 | 1.71 | 0.55 |
| EYS4845 | LCB4 ELO3 | 13.03 | 3.11 |
| EYS5009 | LCB4 CKA2 | 12.91 | 2.14 |

Further improvement of phytosphingosine production was observed upon further genetic modifications (FIG. 1). A 20-30% increase was seen with deletion of the combination of LCB5 and ORM2 genes or the combination of LCB5, ORM2, and CHA1 genes in the LCB4/CKA2 double deletion background. By overexpression of the sphingolipid pathway genes LCB1, LCB2, TSC10, and SUR2 by integration into the yeast genome (Strain EVST20160), phytosphingosine production was about 2.5-fold improved versus the progenitor strain EVST20057. Production of phytosphingosine was further increased by over 30% by overexpression of an additional copy of the sphingolipid pathway genes from plasmids (Strain EVST20240)

Example 3: Cultivation of Strain EVST20240 in a Bioreactor

A fed-batch fermentation was performed with the following parameters: temperature 30° C., pH controlled at 5.85 (regulated with HCl 0.5 M and NH$_4$OH 5 M), and pO$_2$ maintained superior at 20% of the maximum oxygen dissolution by a cascade on stirrer and aeration. The media used were selective SC media for the batch phase and 30-fold concentrated selective SC media (46.38 g/L SC-mix without leucine, histidine, uracil, 201 g/L yeast nitrogen base, 600 g/L glucose, pH 5.8) (for complete SC mixture, see Table 15) for the fed-batch phase, respectively. Both media were supplemented with 50 g/L methyl alpha cyclodextrin. The batch phase was run 11 hours, after which feeding started with an exponential feeding profile (Table 7). Over a period of about 100 h, samples were taken and analysed for both biomass and phytosphingosine production. Phytosphingosine was quantified by LC-MS.

TABLE 7

Feeding profile during bioreactor fermentation

| Time t (h) | F(t) real mL/h |
|---|---|
| 11 | 0.32 |
| 12 | 0.329745 |
| 13 | 0.339788 |
| 14 | 0.350136 |
| 15 | 0.360799 |
| 16 | 0.371787 |
| 17 | 0.38311 |
| 18 | 0.394777 |
| 19 | 0.4068 |
| 20 | 0.419189 |
| 21 | 0.431955 |
| 22 | 0.44511 |
| 23 | 0.458665 |
| 24 | 0.472634 |
| 25 | 0.487028 |
| 26 | 0.50186 |
| 27 | 0.517144 |
| 28 | 0.532893 |
| 29 | 0.549122 |
| 30 | 0.565845 |
| 31 | 0.583078 |
| 32 | 0.600835 |
| 33 | 0.619134 |
| 34 | 0.637989 |
| 35 | 0.657419 |
| 36 | 0.67744 |
| 37 | 0.698071 |
| 38 | 0.719331 |
| 39 | 0.741237 |
| 40 | 0.763811 |
| 41 | 0.787073 |
| 42 | 0.811043 |
| 43 | 0.835743 |
| 44 | 0.861195 |
| 45 | 0.887422 |
| 46 | 0.914448 |
| 47 | 0.942297 |
| 48 | 0.970995 |
| 49 | 1.000566 |
| 50 | 1.031038 |
| 51 | 1.062437 |
| 52 | 1.094793 |
| 53 | 1.128135 |
| 54 | 1.162492 |
| 55 | 1.197895 |
| 56 | 1.234376 |
| 57 | 1.271969 |
| 58 | 1.310706 |
| 59 | 1.350623 |
| 60 | 1.391755 |
| 61 | 1.434141 |
| 62 | 1.477817 |
| 63 | 1.522823 |
| 64 | 1.5692 |
| 65 | 1.616989 |
| 66 | 1.666234 |
| 67 | 1.716978 |
| 68 | 1.769268 |
| 69 | 1.82315 |
| 70 | 1.409005 |
| 71 | 1.451915 |
| 72 | 1.496133 |
| 73 | 1.541697 |
| 74 | 1.588648 |
| 75 | 1.63703 |
| 76 | 1.686885 |
| 77 | 1.738258 |
| 78 | 1.791196 |
| 79 | 1.845746 |
| 80 | 1.901958 |
| 81 | 1.959881 |
| 82 | 2.019568 |
| 83 | 2.081073 |
| 84 | 2.144451 |
| 85 | 2.209759 |
| 86 | 2.277057 |
| 87 | 2.346403 |
| 88 | 2.417862 |
| 89 | 2.491497 |
| 90 | 2.567374 |
| 91 | 2.645562 |
| 92 | 2.726132 |
| 93 | 2.809155 |
| 94 | 2.894706 |
| 95 | 2.982863 |
| 96 | 3.073705 |
| 97 | 3.167313 |
| 98 | 3.263772 |
| 99 | 3.363169 |
| 100 | 3.465593 |
| 101 | 3.571136 |
| 102 | 3.679893 |
| 103 | 3.791962 |
| 104 | 3.907445 |
| 105 | 4.026444 |
| 106 | 4.149068 |
| 107 | 4.275426 |
| 108 | 4.405632 |
| 109 | 4.539803 |
| 110 | 4.678061 |
| 111 | 4.820529 |
| 112 | 4.967336 |
| 113 | 5.118614 |
| 114 | 5.274499 |
| 115 | 5.435131 |
| 116 | 5.600655 |
| 117 | 5.771221 |
| 118 | 5.946981 |
| 119 | 6.128093 |
| 120 | 6.314721 |
| 121 | 6.507033 |
| 122 | 6.705202 |
| 123 | 6.909406 |
| 124 | 7.119829 |
| 125 | 7.33666 |
| 126 | 7.560094 |
| 127 | 7.790333 |

TABLE 7-continued

Feeding profile during bioreactor fermentation

| Time t (h) | F(t) real mL/h |
|---|---|
| 128 | 8.027584 |
| 129 | 8.272061 |
| 130 | 8.523982 |
| 131 | 8.783576 |
| 132 | 9.051076 |
| 133 | 9.326722 |
| 134 | 9.610763 |
| 135 | 9.903455 |
| 136 | 10.20506 |
| 137 | 10.51585 |
| 138 | 10.83611 |
| 139 | 11.16611 |
| 140 | 11.50617 |
| 141 | 11.85659 |
| 142 | 12.21767 |

Figure 2:
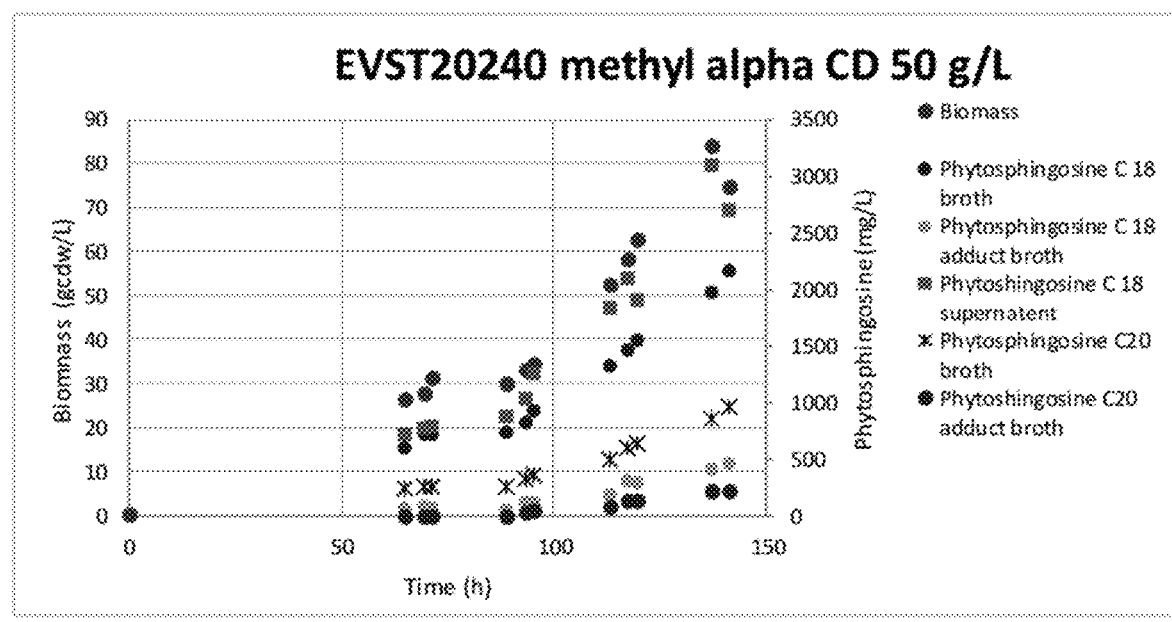
FIG. 2: The Figure shows data regarding Bioreactor fermentation with strain EVST20240.

Results are shown in FIG. 2 and Table 8. In addition to phytosphingosine, several phytosphingosine derivatives were identified in fermentation broth (FIG. 2, Table 8). Phytosphingosine with a carbon chain length of 18 (PHS18) was the major species followed by phytosphingosine with a carbon chain length of 20 (PHS20) and a carbon chain length of 16 (PHS16). In addition PHS18 and PHS20 with one desaturation also were present in significant amounts. Surprisingly, two more phytosphingosine derivatives were present which corresponded to 4-(hydroxymethyl)-2-methyl-6-tetradecanyl-1,3-oxazinan-5-ol and 4-(hydroxymethyl)-2-methyl-6-hexadecanyl-1,3-oxazinan-5-ol. Most likely, both species are reaction products of PHS18 or PHS20 with acetaldehyde. The structure of 4-(hydroxymethyl)-2-methyl-6-tetradecanyl-1,3-oxazinan-5-ol shown as Structure 1 was confirmed by NMR analysis.

TABLE 8

Titers of various phytosphingosine species in a bioreactor

| Product | Titer (mg/L) |
|---|---|
| PHS16 | 295 |
| PHS18 | 2164 |
| PHS18:1 | 327 |
| PHS18 adduct | 452 |
| PHS20 | 962 |
| PHS20:1 | 81 |
| PHS20 adduct | 217 |
| Total PHS | 4498 |

Structure 1

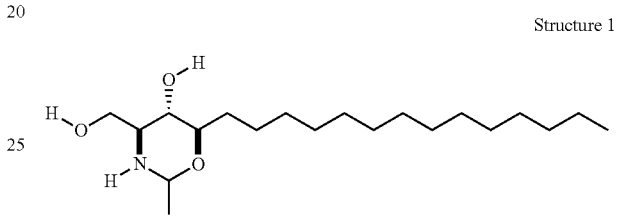

Structure of 4-(hydroxymethyl)-2-methyl-6-tetradecanyl-1,3-oxazinan-5-ol

Materials

Materials used in the Examples are shown in Tables 9-15.

TABLE 9

Primer pairs for gene deletions

| Target Gene | Forward primer # | Forward Primer Sequence | SEQ ID | Reverse Primer # | Reverse primer Sequence | SEQ ID |
|---|---|---|---|---|---|---|
| CHA1 | EV3782 | TAAGTGCTGGATAGACAAGAGACAGGAAAATTAACCAGCGAGATGCCAGCTGAAGCTTCGTACGC | 23 | EV3783 | TCAAGGGCAAATTGATGCTTCAACGAAAAAGTTATTGGATTTTCAGCATAGGCCACTAGTGGATCTG | 24 |
| ORM2 | EV4215 | AAGACTATACCATTATAAAAACGCATAAGAAACAGTTTCATCATGCCAGCTGAAGCTTCGTACGC | 25 | EV4216 | ATATATATATATATATACATATATGCGTATAGGCAGAGCCAACTAGCATAGGCCACTAGTGGATCTG | 26 |
| CKA2 | EV4740 | AAATAGAAGGAACAATAAACCTAAAAGAATAGAAGAAACAGAATGCCAGCTGAAGCTTCGTACGCTGC | 27 | EV4741 | TGGTGGAAAAAGAATTGCCTTGCTAAGAGTATTGTTGTCCAATTACCGCATAGGCCACTAGTGGATCTG | 28 |
| LCB4 | EV4024 | AAGTCTAGCAGCGAAAAGTACGCGAAGAATCTACTATAGATAATGCCAGCTGAAGCTTCGTACGC | 29 | EV4025 | TTTTACAAAAAAATCATTTTTGAAGGAAAATATAACGTTAATCTAGCATAGGCCACTAGTGGATCTG | 30 |
| LCB5 | EV4030 | AAACCACAAATAGTGTAAGATTTAAACAGTAAGCCAAAAGAGATGCCAGCTGAAGCTTCGTACGC | 31 | EV4031 | TTGATTAATTGTTCAGTACGAAGGAAAGATTAAGTAAGTGTCAGCATAGGCCACTAGTGGATCTG | 32 |
| ELO3 | EV5103 | TTATTCGGCTTTTTTCCGTTTGTTTACGAAACATAAACAGTCATGCCAGCTGAAGCTTCGTACGCT | 33 | EV5104 | TTTTTTCTTTTTCATTCGCTGTCAAAAATTCTCGCTTCCTATTTAGCATAGGCCACTAGTGGATCTG | 34 |

TABLE 10

Additional primer sequences

| Primers | Sequence | SEQ ID |
|---|---|---|
| EV3964 | GATGGCGCGCCAACAAACCGAAGTTATCTGATGTAG | 35 |
| EV3965 | GAAGCTTCAGCTGGCGGCCGCCATGATTTATCTTCGTTTCCTGCAG | 36 |
| EV3966 | CTAGTGGCCTATGCGGCCGCTAAAAAACTGTATTATAAGTAAATGCATG | 37 |
| EV3967 | GATGGCGCGCCCCCAAGCCTTGTCCCAAGGCA | 38 |
| EV3970 | GATGGCGCGCCCCACGACGCTTTGTCTTCATTC | 39 |
| EV3971 | TCACTAGCGGCCGCCATCTTTGCCTTCGTTTATCTTGC | 40 |
| EV3972 | AAGATGGCGGCCGCTAGTGACACCGATTATTTAAAGCTG | 41 |
| EV3973 | AAGATGGCGGCCGCTAGTGACACCGATTATTTAAAGCTG | 42 |
| EV3976 | GATGGCGCGCCCTCAGGTATCGTAAGATGCAAGAG | 43 |
| EV3977 | TTTTTAGCGGCCGCCATTAGAATGGTATATCCTTGAAA | 44 |
| EV3978 | CTAATGGCGGCCGCTAAAAAGATTCTCTTTTTTATGATATTTG | 45 |
| EV3979 | GATGGCGCGCCCTACGTCGTTAAGGCCGTTTCTG | 46 |
| EVPR11045 | AGATCTTAAGGGGATATCTTAATGGGGAGCGCTGATTCTCTTTTGGT | 47 |
| EVPR11046 | GGGAACCTCGAGGATATCATGTCCACAAAATCATATACCAGTAGAGCTG | 48 |

TABLE 11

Plasmid sequences

| Plasmid | SEQ ID |
|---|---|
| pEVE1915 | 49 |
| pEVE3191 | 50 |
| pEVE3195 | 51 |
| pEVE4932 | 52 |
| pEV22325 | 53 |
| pEVE2159 | 54 |
| pEVE0078 | 55 |
| pEVE3621 | 62 |
| pEVE3623 | 63 |
| pEVE3624 | 64 |

TABLE 12

Deletion constructs

| Deletion construct | SEQ ID |
|---|---|
| CHA1 | 56 |
| LCB4 | 57 |
| LCB5 | 58 |
| ORM2 | 59 |
| CKA2 | 60 |
| ELO3 | 61 |

TABLE 13

Promoter sequences

| Promoter | SEQ ID |
|---|---|
| GPD1 | 65 |
| TEF2 | 66 |
| PGK1 | 67 |
| TPI1 | 68 |
| TEF1 | 69 |

TABLE 14

Terminator sequences

| Terminator | SEQ ID |
|---|---|
| CYC1 | 70 |
| PGI1 | 71 |
| ADH2 | 72 |
| TDH1 | 73 |
| ADH1 | 74 |

TABLE 15

Complete SC mixture

| Component | Concentration mg/l |
|---|---|
| Adenine | 18 |
| L-Alanine | 76 |
| L-Arginine HCl | 76 |
| L-Asparagine | 76 |
| Aspartic Acid | 76 |
| L-Cysteine | 76 |
| L-Glutamine | 76 |
| L-Glutamic Acid | 76 |
| Glycine | 76 |
| L-Histidine | 76 |

TABLE 15-continued

Complete SC mixture

| Component | Concentration mg/l |
|---|---|
| myo-Inositol | 76 |
| L-Isoleucine | 76 |
| L-Leucine | 380 |
| L-Lysine | 76 |
| L-Methionine | 76 |
| para-Aminobenzoic Acid | 8 |
| L-Phenylalanine | 76 |
| L-Proline | 76 |
| L-Serine | 76 |
| L-Threonine | 76 |
| L-Tryptophan | 76 |
| L-Tyrosine | 76 |
| Uracil | 76 |
| L-Valine | 76 |

INDUSTRIAL APPLICABILITY

According to the present invention, an ability of yeast to produce an objective substance such as phytosphingosine (PHS) and sphinganine (DHS) can be improved, and an objective substance can be efficiently produced.

EXPLANATION OF SEQUENCE LISTING

SEQ ID NO: 1, Nucleotide sequence of LCB1 gene of *Saccharomyces cerevisiae*
SEQ ID NO: 2, Amino acid sequence of Lcb1 protein of *Saccharomyces cerevisiae*
SEQ ID NO: 3, Nucleotide sequence of LCB2 gene of *Saccharomyces cerevisiae*
SEQ ID NO: 4, Amino acid sequence of Lcb2 protein of *Saccharomyces cerevisiae*
SEQ ID NO: 5, Nucleotide sequence of TSC10 gene of *Saccharomyces cerevisiae*
SEQ ID NO: 6, Amino acid sequence of Tsc10 protein of *Saccharomyces cerevisiae*
SEQ ID NO: 7, Nucleotide sequence of SUR2 gene of *Saccharomyces cerevisiae*
SEQ ID NO: 8, Amino acid sequence of Sur2 protein of *Saccharomyces cerevisiae*
SEQ ID NO: 9, Nucleotide sequence of LCB4 gene of *Saccharomyces cerevisiae*
SEQ ID NO: 10, Amino acid sequence of Lcb4 protein of *Saccharomyces cerevisiae*
SEQ ID NO: 11, Nucleotide sequence of LCB5 gene of *Saccharomyces cerevisiae*
SEQ ID NO: 12, Amino acid sequence of Lcb5 protein of *Saccharomyces cerevisiae*
SEQ ID NO: 13, Nucleotide sequence of ELO3 gene of *Saccharomyces cerevisiae*
SEQ ID NO: 14, Amino acid sequence of Elo3 protein of *Saccharomyces cerevisiae*
SEQ ID NO: 15, Nucleotide sequence of CKA2 gene of *Saccharomyces cerevisiae*
SEQ ID NO: 16, Amino acid sequence of Cka2 protein of *Saccharomyces cerevisiae*
SEQ ID NO: 17, Nucleotide sequence of ORM2 gene of *Saccharomyces cerevisiae*
SEQ ID NO: 18, Amino acid sequence of Orm2 protein of *Saccharomyces cerevisiae*
SEQ ID NO: 19, Nucleotide sequence of CHA1 gene of *Saccharomyces cerevisiae*
SEQ ID NO: 20, Amino acid sequence of Cha1 protein of *Saccharomyces cerevisiae*
SEQ ID NO: 21, Nucleotide sequence of SUR2 gene of *Pichia ciferrii*
SEQ ID NO: 22, Amino acid sequence of Sur2 protein of *Pichia ciferrii*
SEQ ID NOS: 23-48, Primers
SEQ ID NOS: 49-55, Plasmids
SEQ ID NOS: 56-61, Gene deletion constructs
SEQ ID NOS: 62-64, Plasmids
SEQ ID NOS: 65-69, Promoters
SEQ ID NOS: 70-74, Terminators

We claim:

1. A method for producing an objective substance, the method comprising:
   cultivating yeast having an ability to produce the objective substance in a culture medium; and
   collecting the objective substance from cells of the yeast and/or the culture medium,
   wherein the yeast has been modified so that the expression and/or activities of proteins encoded by LCB4, CKA2, and ORM2 genes are reduced, and
   wherein the objective substance is selected from the group consisting of phytosphingosine (PHS) and sphinganine (DHS), and
   wherein the culture medium contains cyclodextrin.

2. The method according to claim 1, wherein the activities of the proteins are reduced by attenuating the expression of the LCB4, CKA2, and ORM2 gene, or by disrupting the LCB4, CKA2, and ORM2 gene.

3. The method according to claim 1, wherein the activities of the proteins are reduced by deletion of the LCB4, CKA2, and ORM2 genes.

4. The method according to claim 1, wherein the protein encoded by the LCB4 gene is a protein defined in (A), (B), or (C) mentioned below:
   (A) a protein comprising the amino acid sequence of SEQ ID NO: 10;
   (B) a protein comprising the amino acid sequence of SEQ ID NO: 10 but including substitution, deletion, insertion, and/or addition of 1 to 10 amino acid residues, and having sphingoid base kinase activity;
   (C) a protein comprising an amino acid sequence showing an identity of 90% or higher to the amino acid sequence of SEQ ID NO: 10, and having sphingoid base kinase activity.

5. The method according to claim 1, wherein the protein encoded by the CKA2 gene is a protein defined in (A), (B), or (C) mentioned below:
   (A) a protein comprising the amino acid sequence of SEQ ID NO: 16;
   (B) a protein comprising the amino acid sequence of SEQ ID NO: 16 but including substitution, deletion, insertion, and/or addition of 1 to 10 amino acid residues, and having casein kinase 2 activity;

(C) a protein comprising an amino acid sequence showing an identity of 90% or higher to the amino acid sequence of SEQ ID NO: 16, and having casein kinase 2 activity.

6. The method according to claim 1, wherein the yeast has further been modified so that the expression and/or activity or activities of one or more proteins selected from proteins encoded by LCB5, ELO3, and CHA1 genes are reduced.

7. The method according to claim 6, wherein the activity or activities of the one or more proteins are reduced by attenuating the expression of the respective genes encoding the one or more proteins, or by disrupting the respective genes encoding the one or more proteins.

8. The method according to claim 6, wherein the activity or activities of the one or more proteins are reduced by deletion of the respective genes encoding the one or more proteins.

9. The method according to claim 1, wherein the yeast has further been modified so that the expression and/or activity or activities of one or more proteins selected from proteins encoded by LCB1, LCB2, TSC10, and SUR2 genes are increased.

10. The method according to claim 9, wherein the activity or activities of the one or more proteins are increased by increasing the expression of the respective genes encoding the one or more proteins.

11. The method according to claim 9, wherein the expression of the gene(s) is increased by increasing the copy number of the gene(s), and/or by modifying an expression control sequence of the gene(s).

12. The method according to claim 1, wherein the phytosphingosine is selected from the group consisting of C16 PHS, C18 PHS, C20 PHS, C18:1 PHS, C20:1 PHS, 4-(hydroxymethyl)-2-methyl-6-tetradecanyl-1,3-oxazinan-5-ol, and 4-(hydroxymethyl)-2-methyl-6-hexadecanyl-1,3-oxazinan-5-ol.

13. The method according to claim 1, wherein the yeast belongs to the genus *Saccharomyces*.

14. The method according to claim 1, wherein the yeast is *Saccharomyces cerevisiae*.

15. The method according to claim 1, wherein the yeast is able to produce and accumulate the objective substance in a culture medium or cells of the yeast in an amount larger than that obtainable with a non-modified strain.

\* \* \* \* \*

SEQUENCE LISTING

```
<160> NUMBER OF SEQ ID NOS: 74

<210> SEQ ID NO 1
<211> LENGTH: 1677
<212> TYPE: DNA
<213> ORGANISM: Saccharomyces cerevisiae

<400> SEQUENCE: 1
atggcacaca tcccagaggt tttacccaaa tcaataccga ttccggcatt tattgttacc      60
acctcatcgt acctatggta ctacttcaat ctggtgttga ctcaaatccc gggaggccaa     120
ttcatcgttt cgtacatcaa gaaatcgcat catgacgatc catacaggac cacgttgag      180 ataggctta ttttatacgg gatcatctat tacttgtcca agccacaaca gaaaaagagt     240
cttcaagcac agaagcccaa cctatcgccc caggagattg acgcgctaat tgaggactgg     300
gagcccgagc ctctagtcga cccttctgcc accgatgagc aatcgtggag ggtggccaaa    360
acacccgtca ccatggaaat gcccattcag aaccatatta ctatcaccag aaacaacctg    420
caggagaagt ataccaatgt tttcaatttg gcctcgaaca acttttttgca attgtccgct   480 acggagcccg tgaaagaagt ggtcaagacc actatcaaga attacggtgt gggcgcctgt    540 ggtccccgccg ggttctacgg taaccaggac gttcattaca cgttggaata tgatttagca   600
```

```
cagttctttg gcacccaagg ttccgttctg tacgggcaag acttttgtgc cgcaccctct    660
gttctgcctg ctttcacaaa gcgtggtgat gttatcgtgg cagacgacca ggtgtcatta    720
ccagtgcaaa atgctctgca actaagcaga tccacagtct actacttcaa ccacaacgat    780
atgaattcgc tagaatgttt attaaacgag ttgaccgaac aggagaaact tgagaaactg    840
cccgccattc aagaaaatt tatcgtcact gagggtattt tccacaactc gggcgattta    900
gctccgttgc ctgagttgac taagctgaag aacaagtaca agttcagact atttgttgac    960
gaaaccttct ccattggtgt tcttggcgct acgggccgtg ggttgtcaga gcacttcaac   1020
atggatcgcg caactgccat tgacattacc gttgggtcca tggccaccgc gttggggtcc   1080
accggtggtt ttgtcctggg tgacagtgtt atgtgtttgc caccagcgtat tggttccaat   1140
gcatattgtt tttctgcctg tttgccggct acaccgtca catccgtctc caaagtcttg   1200
aaattgatgg actccaacaa cgacgccgtc cagacgctgc aaaaactatc caaatctttg   1260
catgattcct ttgcatctga cgactccttg cgttcatacg taatcgtcac gtcctctcca   1320
gtgtctgctg tcctacatct gcaactgact cccgcatata ggtctcgcaa gttcggatac   1380
acctgcgaac agctattcga aaccatgtca gctttgcaaa agaagtccca gacaaacaaa   1440
ttcattgagc catacgaaga ggaggaaaaa tttctgcagt ccatagtaga tcatgctctt   1500
attaactaca acgttctcat cacaagaaac actattgttt taaaacagga gacgctacca   1560
attgtcccta gcttgaaaat ctgctgtaac gccgccatgt ccccagagga actcaaaaat   1620
gcttgcgaaa gtgtcaagca gtccatcctt gcctgttgcc aagaatctaa taaataa     1677

<210> SEQ ID NO 2
<211> LENGTH: 558
<212> TYPE: PRT
<213> ORGANISM: Saccharomyces cerevisiae

<400> SEQUENCE: 2

Met Ala His Ile Pro Glu Val Leu Pro Lys Ser Ile Pro Ile Pro Ala
1               5                   10                  15

Phe Ile Val Thr Thr Ser Ser Tyr Leu Trp Tyr Tyr Phe Asn Leu Val
                20                  25                  30

Leu Thr Gln Ile Pro Gly Gly Gln Phe Ile Val Ser Tyr Ile Lys Lys
            35                  40                  45

Ser His His Asp Asp Pro Tyr Arg Thr Val Glu Ile Gly Leu Ile
        50                  55                  60

Leu Tyr Gly Ile Ile Tyr Tyr Leu Ser Lys Pro Gln Gln Lys Lys Ser
65                  70                  75                  80

Leu Gln Ala Gln Lys Pro Asn Leu Ser Pro Gln Glu Ile Asp Ala Leu
                85                  90                  95

Ile Glu Asp Trp Glu Pro Glu Pro Leu Val Asp Pro Ser Ala Thr Asp
            100                 105                 110

Glu Gln Ser Trp Arg Val Ala Lys Thr Pro Val Thr Met Glu Met Pro
        115                 120                 125

Ile Gln Asn His Ile Thr Ile Thr Arg Asn Asn Leu Gln Glu Lys Tyr
    130                 135                 140

Thr Asn Val Phe Asn Leu Ala Ser Asn Phe Leu Gln Leu Ser Ala
145                 150                 155                 160

Thr Glu Pro Val Lys Glu Val Lys Thr Thr Ile Lys Asn Tyr Gly
                165                 170                 175

Val Gly Ala Cys Gly Pro Ala Gly Phe Tyr Gly Asn Gln Asp Val His
            180                 185                 190
```

Tyr Thr Leu Glu Tyr Asp Leu Ala Gln Phe Phe Gly Thr Gln Gly Ser
        195                 200                 205

Val Leu Tyr Gly Gln Asp Phe Cys Ala Ala Pro Ser Val Leu Pro Ala
        210                 215                 220

Phe Thr Lys Arg Gly Asp Val Ile Val Ala Asp Gln Val Ser Leu
225                 230                 235                 240

Pro Val Gln Asn Ala Leu Gln Leu Ser Arg Ser Thr Val Tyr Tyr Phe
                245                 250                 255

Asn His Asn Asp Met Asn Ser Leu Glu Cys Leu Leu Asn Glu Leu Thr
                260                 265                 270

Glu Gln Glu Lys Leu Glu Lys Leu Pro Ala Ile Pro Arg Lys Phe Ile
            275                 280                 285

Val Thr Glu Gly Ile Phe His Asn Ser Gly Asp Leu Ala Pro Leu Pro
        290                 295                 300

Glu Leu Thr Lys Leu Lys Asn Lys Tyr Lys Phe Arg Leu Phe Val Asp
305                 310                 315                 320

Glu Thr Phe Ser Ile Gly Val Leu Gly Ala Thr Gly Arg Gly Leu Ser
                325                 330                 335

Glu His Phe Asn Met Asp Arg Ala Thr Ala Ile Asp Ile Thr Val Gly
            340                 345                 350

Ser Met Ala Thr Ala Leu Gly Ser Thr Gly Gly Phe Val Leu Gly Asp
        355                 360                 365

Ser Val Met Cys Leu His Gln Arg Ile Gly Ser Asn Ala Tyr Cys Phe
        370                 375                 380

Ser Ala Cys Leu Pro Ala Tyr Thr Val Thr Ser Val Ser Lys Val Leu
385                 390                 395                 400

Lys Leu Met Asp Ser Asn Asn Asp Ala Val Gln Thr Leu Gln Lys Leu
                405                 410                 415

Ser Lys Ser Leu His Asp Ser Phe Ala Ser Asp Ser Leu Arg Ser
            420                 425                 430

Tyr Val Ile Val Thr Ser Ser Pro Val Ser Ala Val Leu His Leu Gln
        435                 440                 445

Leu Thr Pro Ala Tyr Arg Ser Arg Lys Phe Gly Tyr Thr Cys Glu Gln
        450                 455                 460

Leu Phe Glu Thr Met Ser Ala Leu Gln Lys Ser Gln Thr Asn Lys
465                 470                 475                 480

Phe Ile Glu Pro Tyr Glu Glu Glu Lys Phe Leu Gln Ser Ile Val
                485                 490                 495

Asp His Ala Leu Ile Asn Tyr Asn Val Leu Ile Thr Arg Asn Thr Ile
                500                 505                 510

Val Leu Lys Gln Glu Thr Leu Pro Ile Val Pro Ser Leu Lys Ile Cys
            515                 520                 525

Cys Asn Ala Ala Met Ser Pro Glu Glu Leu Lys Asn Ala Cys Glu Ser
        530                 535                 540

Val Lys Gln Ser Ile Leu Ala Cys Cys Gln Glu Ser Asn Lys
545                 550                 555

<210> SEQ ID NO 3
<211> LENGTH: 1686
<212> TYPE: DNA
<213> ORGANISM: Saccharomyces cerevisiae

<400> SEQUENCE: 3
atgagtactc ctgcaaacta tacccgtgtg cccctgtgcg aaccagagga gctgccagac        60

```
gacatacaaa aagaaaatga atatggtaca ctagattctc cggggcattt gtatcaagtc    120
aagtcacgtc atgggaagcc actacctgag cccgttgtcg acacccctcc ttattacatt    180
tctttgttaa catatctaaa ttatttgatt ctgattatat taggtcatgt tcacgacttc    240
ttaggtatga ccttccaaaa aaacaaacat ctggatcttt tagagcatga tgggttagca    300
ccttggtttt caaatttcga gagttttttat gtcaggagaa ttaaaatgag aattgatgat    360
tgcttttcta gaccaactac tggtgttcct ggtagattta ttcgttgtat tgatagaatt    420
tctcataata taaatgagta ttttaccctac tcaggcgcag tgtatccatg catgaactta    480
tcatcatata actatttagg cttcgcacaa agtaagggtc aatgtaccga tgccgccttg    540
gaatctgtcg ataaatattc tattcaatct ggtggtccaa gagctcaaat cggtaccaca    600
gatttgcaca ttaaagcaga gaaattagtt gctagattta tcggtaagga ggatgccctc    660
gttttttcga tgggttatgg tacaaatgca aacttgttca acgctttcct cgataaaaag    720
tgtttagtta tctctgacga attgaaccac acctctatta gaacaggtgt taggctttct    780
ggtgctgctg tgcgaacttt caagcatggt gatatggtgg gtttagaaaa gcttatcaga    840
gaacagatag tacttggtca accaaaaaca aatcgtccat ggaagaaaat tttaattgc    900 gcagaagggt tgttttccat ggaaggtact ttgtgtaact tgccaaaatt ggttgaattg    960
aagaagaaat ataaatgtta cttgtttatc gatgaagccc attctatagg cgctatgggc   1020
ccaactggtc gcggtgtttg tgaaatattt ggcgttgatc ccaaggacgt cgacattcta   1080
atgggtactt tcactaagtc gtttggtgct gctggtggtt acattgctgc tgatcaatgg   1140
attatcgata gactgaggtt ggatttaacc actgtgagtt atagtgagtc aatgccggct   1200
cctgttttag ctcaaactat ttcctcatta caaaccatta gtggtgaaat atgtcccgga   1260
caaggtactg aaagattgca acgtatagcc tttaattccc gttatctacg tttagctttg   1320
caaaggttag gatttattgt ctacggtgtg gctgactcac cagttattcc cttactactg   1380
tattgtccct caaagatgcc cgcatttttcg agaatgatgt tacaaagacg gattgctgtt   1440
gttgttgttg cttatcctgc tactccgctg atcgaatcaa gagtaagatt ctgtatgtct   1500
gcatctttaa caaaggaaga tatcgattat ttactgcgtc atgttagtga agttggtgac   1560
aaattgaatt tgaaatcaaa ttccggcaaa tccagttacg acggtaaacg tcaaagatgg   1620
gacatcgagg aagttatcag gagaacacct gaagattgta aggacgacaa gtattttgtt   1680
aattga                                                              1686
```

<210> SEQ ID NO 4
<211> LENGTH: 561
<212> TYPE: PRT
<213> ORGANISM: Saccharomyces cerevisiae

<400> SEQUENCE: 4

```
Met Ser Thr Pro Ala Asn Tyr Thr Arg Val Pro Leu Cys Glu Pro Glu
1               5                   10                  15

Glu Leu Pro Asp Asp Ile Gln Lys Glu Asn Glu Tyr Gly Thr Leu Asp
            20                  25                  30

Ser Pro Gly His Leu Tyr Gln Val Lys Ser Arg His Gly Lys Pro Leu
        35                  40                  45

Pro Glu Pro Val Val Asp Thr Pro Pro Tyr Tyr Ile Ser Leu Leu Thr
    50                  55                  60

Tyr Leu Asn Tyr Leu Ile Leu Ile Ile Leu Gly His Val His Asp Phe
65                  70                  75                  80
```

```
Leu Gly Met Thr Phe Gln Lys Asn Lys His Leu Asp Leu Leu Glu His
                85                  90                  95

Asp Gly Leu Ala Pro Trp Phe Ser Asn Phe Glu Ser Phe Tyr Val Arg
            100                 105                 110

Arg Ile Lys Met Arg Ile Asp Asp Cys Phe Ser Arg Pro Thr Thr Gly
        115                 120                 125

Val Pro Gly Arg Phe Ile Arg Cys Ile Asp Arg Ile Ser His Asn Ile
    130                 135                 140

Asn Glu Tyr Phe Thr Tyr Ser Gly Ala Val Tyr Pro Cys Met Asn Leu
145                 150                 155                 160

Ser Ser Tyr Asn Tyr Leu Gly Phe Ala Gln Ser Lys Gly Gln Cys Thr
                165                 170                 175

Asp Ala Ala Leu Glu Ser Val Asp Lys Tyr Ser Ile Gln Ser Gly Gly
            180                 185                 190

Pro Arg Ala Gln Ile Gly Thr Thr Asp Leu His Ile Lys Ala Glu Lys
        195                 200                 205

Leu Val Ala Arg Phe Ile Gly Lys Glu Asp Ala Leu Val Phe Ser Met
    210                 215                 220

Gly Tyr Gly Thr Asn Ala Asn Leu Phe Asn Ala Phe Leu Asp Lys Lys
225                 230                 235                 240

Cys Leu Val Ile Ser Asp Glu Leu Asn His Thr Ser Ile Arg Thr Gly
                245                 250                 255

Val Arg Leu Ser Gly Ala Ala Val Arg Thr Phe Lys His Gly Asp Met
            260                 265                 270

Val Gly Leu Glu Lys Leu Ile Arg Glu Gln Ile Val Leu Gly Gln Pro
        275                 280                 285

Lys Thr Asn Arg Pro Trp Lys Lys Ile Leu Ile Cys Ala Glu Gly Leu
    290                 295                 300

Phe Ser Met Glu Gly Thr Leu Cys Asn Leu Pro Lys Leu Val Glu Leu
305                 310                 315                 320

Lys Lys Lys Tyr Lys Cys Tyr Leu Phe Ile Asp Glu Ala His Ser Ile
                325                 330                 335

Gly Ala Met Gly Pro Thr Gly Arg Gly Val Cys Glu Ile Phe Gly Val
            340                 345                 350

Asp Pro Lys Asp Val Asp Ile Leu Met Gly Thr Phe Thr Lys Ser Phe
        355                 360                 365

Gly Ala Ala Gly Gly Tyr Ile Ala Ala Asp Gln Trp Ile Ile Asp Arg
    370                 375                 380

Leu Arg Leu Asp Leu Thr Thr Val Ser Tyr Ser Glu Ser Met Pro Ala
385                 390                 395                 400

Pro Val Leu Ala Gln Thr Ile Ser Ser Leu Gln Thr Ile Ser Gly Glu
                405                 410                 415

Ile Cys Pro Gly Gln Gly Thr Glu Arg Leu Gln Arg Ile Ala Phe Asn
            420                 425                 430

Ser Arg Tyr Leu Arg Leu Ala Leu Gln Arg Leu Gly Phe Ile Val Tyr
        435                 440                 445

Gly Val Ala Asp Ser Pro Val Ile Pro Leu Leu Leu Tyr Cys Pro Ser
    450                 455                 460

Lys Met Pro Ala Phe Ser Arg Met Met Leu Gln Arg Arg Ile Ala Val
465                 470                 475                 480

Val Val Val Ala Tyr Pro Ala Thr Pro Leu Ile Glu Ser Arg Val Arg
                485                 490                 495
```

```
Phe Cys Met Ser Ala Ser Leu Thr Lys Glu Asp Ile Asp Tyr Leu Leu
                500                 505                 510

Arg His Val Ser Glu Val Gly Asp Lys Leu Asn Leu Lys Ser Asn Ser
        515                 520                 525

Gly Lys Ser Ser Tyr Asp Gly Lys Arg Gln Arg Trp Asp Ile Glu Glu
    530                 535                 540

Val Ile Arg Arg Thr Pro Glu Asp Cys Lys Asp Lys Tyr Phe Val
545                 550                 555                 560

Asn

<210> SEQ ID NO 5
<211> LENGTH: 963
<212> TYPE: DNA
<213> ORGANISM: Saccharomyces cerevisiae

<400> SEQUENCE: 5
atgaagttta cgttagaaga ccaagttgtg ttgatcactg gtggttcaca aggtcttgga    60
aaggaattcg ccaaaaaata ttataatgag gctgaaaaca caaagattat tatcgtcagt   120
aggtcagagg ctagactgct ggacacatgc aacgaaatta ggattgaagc tcacctgaga   180
agggaaacca ctgacgaggg ccaagtgcaa cataagttgg ctgcgccctt ggaccttgag   240
caacggttat tttactaccc atgcgacttg tcctgctacg aatccgtgga atgtttgttc   300
aatgccctga gagacttgga tttactccct acacaaacgt tatgctgtgc aggggggggct  360 gttcctaagt tatttcgtgg gctaagcgga catgagttga acttgggtat ggacatcaac   420
tataaaacaa ctttgaacgt ggcacatcag attgcccttg cagagcaaac caaggaacac   480
cacctcatca tcttttctag tgccaccgcg ctttacccat tgtgggcta ttcccagtat    540 gcgcctgcaa aagctgcaat caaatcactg gtagcaatct taagacaaga actgacgaac   600
ttccgtatca gttgtgttta tcctggtaat tttgaaagcg aaggtttcac tgtagagcag   660
ctaacgaaac ccgaaattac aaagttgatc gaaggcccct cagacgctat cccatgcaaa   720
caagcatgtg atatcattgc caagtcgctg ccagaggtg atgatgacgt ttttacagat    780
tttgtcggat ggatgataat ggggatggac cttgggctca ccgcaaagaa aagccgcttt   840
gttccgttgc aatggatttt tggtgtccta tcaaacattc tggtcgtgcc attctacatg   900
gttggctgtt cctggtatat caggaaatgg tttcgtgaaa atgacggcaa gaaggccaac   960
tga                                                                963

<210> SEQ ID NO 6
<211> LENGTH: 320
<212> TYPE: PRT
<213> ORGANISM: Saccharomyces cerevisiae

<400> SEQUENCE: 6

Met Lys Phe Thr Leu Glu Asp Gln Val Val Leu Ile Thr Gly Gly Ser
1               5                   10                  15

Gln Gly Leu Gly Lys Glu Phe Ala Lys Lys Tyr Tyr Asn Glu Ala Glu
            20                  25                  30

Asn Thr Lys Ile Ile Ile Val Ser Arg Ser Glu Ala Arg Leu Leu Asp
        35                  40                  45

Thr Cys Asn Glu Ile Arg Ile Glu Ala His Leu Arg Arg Glu Thr Thr
    50                  55                  60

Asp Glu Gly Gln Val Gln His Lys Leu Ala Ala Pro Leu Asp Leu Glu
65                  70                  75                  80
```

```
Gln Arg Leu Phe Tyr Tyr Pro Cys Asp Leu Ser Cys Tyr Glu Ser Val
                85                  90                  95

Glu Cys Leu Phe Asn Ala Leu Arg Asp Leu Asp Leu Leu Pro Thr Gln
            100                 105                 110

Thr Leu Cys Cys Ala Gly Gly Ala Val Pro Lys Leu Phe Arg Gly Leu
        115                 120                 125

Ser Gly His Glu Leu Asn Leu Gly Met Asp Ile Asn Tyr Lys Thr Thr
    130                 135                 140

Leu Asn Val Ala His Gln Ile Ala Leu Ala Glu Gln Thr Lys Glu His
145                 150                 155                 160

His Leu Ile Ile Phe Ser Ser Ala Thr Ala Leu Tyr Pro Phe Val Gly
                165                 170                 175

Tyr Ser Gln Tyr Ala Pro Ala Lys Ala Ala Ile Lys Ser Leu Val Ala
            180                 185                 190

Ile Leu Arg Gln Glu Leu Thr Asn Phe Arg Ile Ser Cys Val Tyr Pro
        195                 200                 205

Gly Asn Phe Glu Ser Gly Phe Thr Val Glu Gln Leu Thr Lys Pro
    210                 215                 220

Glu Ile Thr Lys Leu Ile Glu Gly Pro Ser Asp Ala Ile Pro Cys Lys
225                 230                 235                 240

Gln Ala Cys Asp Ile Ile Ala Lys Ser Leu Ala Arg Gly Asp Asp Asp
                245                 250                 255

Val Phe Thr Asp Phe Val Gly Trp Ile Met Gly Met Asp Leu Gly
            260                 265                 270

Leu Thr Ala Lys Lys Ser Arg Phe Val Pro Leu Gln Trp Ile Phe Gly
        275                 280                 285

Val Leu Ser Asn Ile Leu Val Val Pro Phe Tyr Met Val Gly Cys Ser
    290                 295                 300

Trp Tyr Ile Arg Lys Trp Phe Arg Glu Asn Asp Gly Lys Lys Ala Asn
305                 310                 315                 320

<210> SEQ ID NO 7
<211> LENGTH: 1050
<212> TYPE: DNA
<213> ORGANISM: Saccharomyces cerevisiae

<400> SEQUENCE: 7
atgaacgtaa catcgaatgc aactgcagcc ggttcctttc cactagcatt tggtctcaag      60
acctcatttg ggtttatgca ctatgccaag gcccctgcca ttaatttacg ccccaaggaa     120
tccttgctgc cggaaatgag tgatggtgtg ctggccttgg ttgcgccggt tgttgcctac     180
tgggcgttgt ctggtatatt ccatgtaata gacactttcc atctggctga aagtacaga     240 attcatccga gcgaagaggt tgccaagagg aacaaggcgt cgagaatgca tgttttcctt     300
gaagtgattc tacaacatat catacagacc attgttggcc ttatctttat gcacttcgag     360
ccgatctaca tgactgggtt tgaagaaaat gccatgtgga agcttcgtgc agaccttcct     420
cggattattc cagatgccgc tatttattac ggctatatgt acggaatgtc cgctttgaag     480
atctttgcag ctttttatt cgttgataca tggcaatact ttttgcatag attgatgcat     540
atgaataaga cctatacaa atggttccac tctgttcatc atgaactata cgtgccatat     600
gcttacggtg ctcttttcaa caatcctgtt gagggcttct tgttagatac tttgggaacc     660
ggtattgcca tgcgttaac tcatttgact cacagagagc aaatcattct ttttacctt      720 gccaccatga agactgtcga tgaccactgt gggtatgctt tgccacttga cccattccaa     780
```

```
tggcttttcc ctaataacgc tgtctatcac gatatccacc accagcaatt tggtatcaag    840
acgaactttg ctcaaccatt tttcactttc tgggacaatt tgttccaaac taactttaaa    900
gggtttgaag aatatcaaaa gaagcaaaga cgtgtcacca tcgacaagta caaagagttt    960
ttgcaagaga gagaattgga aaagaaggag aaactcaaaa acttcaaagc tatgaatgct   1020
gctgaaaatg aagtaaagaa agagaaataa                                    1050
```

<210> SEQ ID NO 8
<211> LENGTH: 349
<212> TYPE: PRT
<213> ORGANISM: Saccharomyces cerevisiae

<400> SEQUENCE: 8

```
Met Asn Val Thr Ser Asn Ala Thr Ala Ala Gly Ser Phe Pro Leu Ala
1               5                  10                  15

Phe Gly Leu Lys Thr Ser Phe Gly Phe Met His Tyr Ala Lys Ala Pro
            20                  25                  30

Ala Ile Asn Leu Arg Pro Lys Glu Ser Leu Leu Pro Glu Met Ser Asp
        35                  40                  45

Gly Val Leu Ala Leu Val Ala Pro Val Val Ala Tyr Trp Ala Leu Ser
    50                  55                  60

Gly Ile Phe His Val Ile Asp Thr Phe His Leu Ala Glu Lys Tyr Arg
65                  70                  75                  80

Ile His Pro Ser Glu Glu Val Ala Lys Arg Asn Lys Ala Ser Arg Met
                85                  90                  95

His Val Phe Leu Glu Val Ile Leu Gln His Ile Ile Gln Thr Ile Val
            100                 105                 110

Gly Leu Ile Phe Met His Phe Glu Pro Ile Tyr Met Thr Gly Phe Glu
        115                 120                 125

Glu Asn Ala Met Trp Lys Leu Arg Ala Asp Leu Pro Arg Ile Ile Pro
    130                 135                 140

Asp Ala Ala Ile Tyr Tyr Gly Tyr Met Tyr Gly Met Ser Ala Leu Lys
145                 150                 155                 160

Ile Phe Ala Gly Phe Leu Phe Val Asp Thr Trp Gln Tyr Phe Leu His
                165                 170                 175

Arg Leu Met His Met Asn Lys Thr Leu Tyr Lys Trp Phe His Ser Val
            180                 185                 190

His His Glu Leu Tyr Val Pro Tyr Ala Tyr Gly Ala Leu Phe Asn Asn
        195                 200                 205

Pro Val Glu Gly Phe Leu Leu Asp Thr Leu Gly Thr Gly Ile Ala Met
    210                 215                 220

Thr Leu Thr His Leu Thr His Arg Glu Gln Ile Ile Leu Phe Thr Phe
225                 230                 235                 240

Ala Thr Met Lys Thr Val Asp Asp His Cys Gly Tyr Ala Leu Pro Leu
                245                 250                 255

Asp Pro Phe Gln Trp Leu Phe Pro Asn Asn Ala Val Tyr His Asp Ile
            260                 265                 270

His His Gln Gln Phe Gly Ile Lys Thr Asn Phe Ala Gln Pro Phe Phe
        275                 280                 285

Thr Phe Trp Asp Asn Leu Phe Gln Thr Asn Phe Lys Gly Phe Glu Glu
    290                 295                 300

Tyr Gln Lys Lys Gln Arg Arg Val Thr Ile Asp Lys Tyr Lys Glu Phe
305                 310                 315                 320

Leu Gln Glu Arg Glu Leu Glu Lys Lys Glu Lys Leu Lys Asn Phe Lys
```

325                 330                 335
Ala Met Asn Ala Ala Glu Asn Glu Val Lys Lys Glu Lys
            340                 345

<210> SEQ ID NO 9
<211> LENGTH: 1875
<212> TYPE: DNA
<213> ORGANISM: Saccharomyces cerevisiae

<400> SEQUENCE: 9

| | | | | | |
|---|---|---|---|---|---|
| atggtggtgc | agaaaaaact | tagggctatc | ttgaccgatg | aaggtgtatt | gatcaaatcg | 60 |
| caatcacacc | atatgttcaa | taagcatggt | caactcagaa | gcggagattc | tttatccttg | 120 |
| ttgagctgct | tgtcctgtct | ggatgatgga | actttgagct | ctgatggagg | ttcttttgat | 180 |
| gaggatgatt | ccctggaact | gttgcctctt | aatactacca | ttccgttcaa | cagaattttg | 240 |
| aacgcaaaat | atgtgaatgt | cggtcagaaa | ggcttcaata | tggcaaaat | ttcttcgaat | 300 |
| ccttttcaaa | cggaaaatct | gagttcttcg | tctgaaaatg | acgacgttga | gaatcatagt | 360 |
| ttgagcaatg | ataaggctcc | tgtaagcgaa | tcacagtcat | ttcccaaaaa | agacaagtgg | 420 |
| gatacaaaaa | cgaacactgt | gaaggtgtct | cccgatgatt | cacaggataa | ctcaccatct | 480 |
| ttagggataa | aagataatca | acagttaatt | gagttaactt | ttgctgtacc | caagggccat | 540 |
| gatgttatac | cacaaaaatt | aaccttgtta | atagatcacg | tttctaggaa | atcgagagca | 600 |
| aataccggag | aggagaacat | ttcttctggt | actgtggaag | aaatcctgga | aaaaagttat | 660 |
| gaaaattcca | agagaaacag | atcgatatta | gtcattatta | atccccacgg | tggtaaaggt | 720 |
| actgctaaaa | atttattcct | gacaaaagca | aggccaatac | tagtggaaag | tggctgcaaa | 780 |
| atagaaattg | catacacaaa | atatgcccgt | cacgccatcg | atattgccaa | agatttagat | 840 |
| atcagcaaat | acgataccat | tgcatgtgcc | tcgggtgatg | gtattccata | cgaagtaatt | 900 |
| aatgggcttt | atagaagacc | cgacagagtg | gatgcgttca | ataaactagc | cgtaactcag | 960 |
| ctaccttgcg | gttcaggaaa | tgctatgagc | atttcatgtc | attggacaaa | taccccatcg | 1020 |
| tacgccgctc | tgtgccttgt | caaatccatt | gaaacaagaa | tagacttaat | gtgttgttcc | 1080 |
| caaccttctt | atatgaacga | atggccaaga | ttatcctttt | tgagtcagac | gtacggcgtt | 1140 |
| attgcagaat | ctgatattaa | cactgaattc | atcagatgga | tgggtcccgt | taggtttaat | 1200 |
| ttgggtgtag | cattcaacat | tatccaaggt | aagaaatatc | cctgcgaagt | tttcgtcaaa | 1260 |
| tatgctgcca | aatctaaaaa | ggaattaaaa | gttcatttct | tagaaaataa | agataaaaac | 1320 |
| aaaggatgtt | taaccttcga | accaaatcct | agcccaaact | cttcgccgga | tttactatct | 1380 |
| aaaaacaata | tcaacaacag | tacaaaagat | gaactttcac | cgaattttct | caacgaggac | 1440 |
| aactttaaat | taaagtatcc | gatgacgaa | ccagtaccta | gagactggga | gaaaatggat | 1500 |
| tcagagctaa | ctgataactt | aacaatcttt | tacacaggga | aaatgccgta | tattgctaag | 1560 |
| gacaccaaat | tttttcccgc | tgctttacca | gcggatggta | ccattgattt | agtcataacg | 1620 |
| gatgcaagaa | tcccagtgac | aagaatgaca | ccaatttat | tatccttgga | taaaggttct | 1680 |
| catgtattag | agccagaagt | tattcactca | aaaatattgg | cttataagat | tataccaaaa | 1740 |
| gtggagtcag | gtttattttc | agtggatggt | gaaaagtttc | ctttggaacc | cttgcaagtg | 1800 |
| gaaataatgc | ccatgttatg | caagacgttg | ctaaggaatg | gtagatatat | cgatacagag | 1860 |
| tttgaatcca | tgtag | | | | | 1875 |

<210> SEQ ID NO 10

-continued

```
<211> LENGTH: 624
<212> TYPE: PRT
<213> ORGANISM: Saccharomyces cerevisiae

<400> SEQUENCE: 10

Met Val Val Gln Lys Lys Leu Arg Ala Ile Leu Thr Asp Glu Gly Val
1               5                   10                  15

Leu Ile Lys Ser Gln Ser His Met Phe Asn Lys His Gly Gln Leu
                20                  25                  30

Arg Ser Gly Asp Ser Leu Ser Leu Ser Cys Leu Ser Cys Leu Asp
            35                  40                  45

Asp Gly Thr Leu Ser Ser Asp Gly Gly Ser Phe Asp Glu Asp Asp Ser
    50                  55                  60

Leu Glu Leu Leu Pro Leu Asn Thr Thr Ile Pro Phe Asn Arg Ile Leu
65              70                  75                  80

Asn Ala Lys Tyr Val Asn Val Gly Gln Lys Gly Phe Asn Asn Gly Lys
                85                  90                  95

Ile Ser Ser Asn Pro Phe Gln Thr Glu Asn Leu Ser Ser Ser Glu
            100                 105                 110

Asn Asp Asp Val Glu Asn His Ser Leu Ser Asn Asp Lys Ala Pro Val
    115                 120                 125

Ser Glu Ser Gln Ser Phe Pro Lys Lys Asp Lys Trp Asp Thr Lys Thr
130                 135                 140

Asn Thr Val Lys Val Ser Pro Asp Asp Ser Gln Asp Asn Ser Pro Ser
145                 150                 155                 160

Leu Gly Ile Lys Asp Asn Gln Gln Leu Ile Glu Leu Thr Phe Ala Val
                165                 170                 175

Pro Lys Gly His Asp Val Ile Pro Gln Lys Leu Thr Leu Leu Ile Asp
            180                 185                 190

His Val Ser Arg Lys Ser Arg Ala Asn Thr Gly Glu Glu Asn Ile Ser
    195                 200                 205

Ser Gly Thr Val Glu Glu Ile Leu Glu Lys Ser Tyr Glu Asn Ser Lys
210                 215                 220

Arg Asn Arg Ser Ile Leu Val Ile Ile Asn Pro His Gly Gly Lys Gly
225                 230                 235                 240

Thr Ala Lys Asn Leu Phe Leu Thr Lys Ala Arg Pro Ile Leu Val Glu
                245                 250                 255

Ser Gly Cys Lys Ile Glu Ile Ala Tyr Thr Lys Tyr Ala Arg His Ala
            260                 265                 270

Ile Asp Ile Ala Lys Asp Leu Asp Ile Ser Lys Tyr Asp Thr Ile Ala
    275                 280                 285

Cys Ala Ser Gly Asp Gly Ile Pro Tyr Glu Val Ile Asn Gly Leu Tyr
290                 295                 300

Arg Arg Pro Asp Arg Val Asp Ala Phe Asn Lys Leu Ala Val Thr Gln
305                 310                 315                 320

Leu Pro Cys Gly Ser Gly Asn Ala Met Ser Ile Ser Cys His Trp Thr
                325                 330                 335

Asn Asn Pro Ser Tyr Ala Ala Leu Cys Leu Val Lys Ser Ile Glu Thr
            340                 345                 350

Arg Ile Asp Leu Met Cys Cys Ser Gln Pro Ser Tyr Met Asn Glu Trp
    355                 360                 365

Pro Arg Leu Ser Phe Leu Ser Gln Thr Tyr Gly Val Ile Ala Glu Ser
370                 375                 380

Asp Ile Asn Thr Glu Phe Ile Arg Trp Met Gly Pro Val Arg Phe Asn
```

```
                385                 390                 395                 400
Leu Gly Val Ala Phe Asn Ile Ile Gln Gly Lys Lys Tyr Pro Cys Glu
                    405                 410                 415

Val Phe Val Lys Tyr Ala Ala Lys Ser Lys Lys Glu Leu Lys Val His
                420                 425                 430

Phe Leu Glu Asn Lys Asp Lys Asn Lys Gly Cys Leu Thr Phe Glu Pro
            435                 440                 445

Asn Pro Ser Pro Asn Ser Ser Pro Asp Leu Leu Ser Lys Asn Asn Ile
        450                 455                 460

Asn Asn Ser Thr Lys Asp Glu Leu Ser Pro Asn Phe Leu Asn Glu Asp
465                 470                 475                 480

Asn Phe Lys Leu Lys Tyr Pro Met Thr Glu Pro Val Pro Arg Asp Trp
                485                 490                 495

Glu Lys Met Asp Ser Glu Leu Thr Asp Asn Leu Thr Ile Phe Tyr Thr
                500                 505                 510

Gly Lys Met Pro Tyr Ile Ala Lys Asp Thr Lys Phe Phe Pro Ala Ala
            515                 520                 525

Leu Pro Ala Asp Gly Thr Ile Asp Leu Val Ile Thr Asp Ala Arg Ile
        530                 535                 540

Pro Val Thr Arg Met Thr Pro Ile Leu Leu Ser Leu Asp Lys Gly Ser
545                 550                 555                 560

His Val Leu Glu Pro Glu Val Ile His Ser Lys Ile Leu Ala Tyr Lys
                565                 570                 575

Ile Ile Pro Lys Val Glu Ser Gly Leu Phe Ser Val Asp Gly Glu Lys
                580                 585                 590

Phe Pro Leu Glu Pro Leu Gln Val Glu Ile Met Pro Met Leu Cys Lys
            595                 600                 605

Thr Leu Leu Arg Asn Gly Arg Tyr Ile Asp Thr Glu Phe Glu Ser Met
        610                 615                 620

<210> SEQ ID NO 11
<211> LENGTH: 2064
<212> TYPE: DNA
<213> ORGANISM: Saccharomyces cerevisiae

<400> SEQUENCE: 11
atgactttga aaccttcaaa gagacgtaag ggcaggtctc gccattccag gaagaagcaa      60
ataacgtcag cgatactgac tgaggaagga ataatgatca aggcaaaacc atcaagtcct     120
tacacatacg caaatagaat ggcagataaa cgaagtcgca gcagcattga caacatcagt     180
agaactagct ttcaaagcaa catcagtaga actagctttc aaagcaacag tgataacaac     240
agtatatttg aaacggcttc actaattagc tgtgttacct gtttaagcga tactgataca     300
atagacagat cggaaacatc gacaacggat acaagtaaag atgatctttc tgctaatcca     360
aaacttcatt atccttcggt gaatggtcaa ttgccagcaa acaccgttat cccctatgga     420
cgaattctgg atgccagata cattgaaaag gaacctctgc attattatga tgccaattca     480
tcacccagtt caccttttaag cagctcaatg agtaacatta gtgaaaagtg tgatcttgat     540
gaattagagt cttcccaaaa aaaagaaagg aagggcaact cgctatcgcg aggaagtaac     600
agtagtagta gcctcctgac ttccagatct ccttttacga aactagtaga ggttatattt     660
gctaggccaa gacggcatga cgttgtaccc aaaagggttt cattgtatat tgactataaa     720
ccccattcat cttctcactt aaaagaagaa gatgacttgg ttgaggagat tttaaagaga     780
agctacaaaa acactagaag gaacaaatcc atatttgtga tcattaatcc gtttggtggt     840
```

-continued

```
aaaggtaagg cgaaaaaact gtttatgaca aaggcaaagc cgttactatt agcaagtcgg    900
tgttccatag aagtggttta tacaaaatac cctggtcatg ctatagagat cgcgcgggaa    960
atggatattg acaaatatga cactattgct tgcgcttcgg gagatggcat tcctcatgag   1020
gtgatcaatg ggttatacca aaggcctgat catgtcaaag cattcaacaa tatcgccatt   1080
acagaaattc catgcggatc aggtaacgca atgagcgtat cctgccactg acaaacaat    1140 ccttcgtact caactttatg cttaattaaa tcgatagaga ctagaattga tttgatgtgt   1200
tgttcgcagc cttcttatgc aagagagcac ccaaagttat cattttttaag tcaaacatat   1260 ggtctcattg cagaaactga cataaacact gaatttatta gatggatggg acctgcaagg   1320
tttgaattgg gtgtagcctt caatatcata caaaaaaaa aatatccttg tgagatatat    1380
gtaaagtatg ctgccaaatc aaaaaacgag ttaaaaaatc attacctgga acacaaaaat   1440
aaagggtcgt tagaattcca gcatattact atgaacaaag ataacgagga ttgtgataat   1500
tacaattacg aaaatgaata cgaaaccgaa acgaagatg aagatgaaga tgcggatgcg   1560
gatgacgaag actcccactt gatatctcgt gatctggcag attctagtgc tgatcaaatt   1620
aaagaggaag atttcaaaat aaaatatcca ttagatgaag gtatccctag tgactgggaa   1680
agattggatc ctaatatttc gaacaaccta ggtatcttct atacgggtaa aatgccatat   1740
gtggctgctg acactaaatt cttttccggca gcgcttcctt cagatggtac aatggatatg   1800
gttatcaccg atgcaagaac ctcgttgacg aggatggcac caatcctgct gggactagat   1860
aagggttccc atgttttaca accggaagtc ttacactcta aaattttggc atacaagata   1920
ataccaaagc tagggaacgg cttgttctct gtcgatggcg agaaatttcc tctagagccc   1980
cttcaagtcg aaattatgcc acgcttatgc aagacgttac tgagaaatgg ccgttatgtg   2040
gacacagatt tcgattctat gtga                                          2064
```

<210> SEQ ID NO 12
<211> LENGTH: 687
<212> TYPE: PRT
<213> ORGANISM: Saccharomyces cerevisiae

<400> SEQUENCE: 12

```
Met Thr Leu Lys Pro Ser Lys Arg Arg Lys Gly Arg Ser Arg His Ser
1               5                   10                  15

Arg Lys Lys Gln Ile Thr Ser Ala Ile Leu Thr Glu Glu Gly Ile Met
                20                  25                  30

Ile Lys Ala Lys Pro Ser Ser Pro Tyr Thr Tyr Ala Asn Arg Met Ala
            35                  40                  45

Asp Lys Arg Ser Arg Ser Ser Ile Asp Asn Ile Ser Arg Thr Ser Phe
        50                  55                  60

Gln Ser Asn Ile Ser Arg Thr Ser Phe Gln Ser Asn Ser Asp Asn Asn
65                  70                  75                  80

Ser Ile Phe Glu Thr Ala Ser Leu Ile Ser Cys Val Thr Cys Leu Ser
                85                  90                  95

Asp Thr Asp Thr Ile Asp Arg Ser Glu Thr Ser Thr Thr Asp Thr Ser
            100                 105                 110

Lys Asp Asp Leu Ser Ala Asn Pro Lys Leu His Tyr Pro Ser Val Asn
        115                 120                 125

Gly Gln Leu Pro Ala Asn Thr Val Ile Pro Tyr Gly Arg Ile Leu Asp
    130                 135                 140

Ala Arg Tyr Ile Glu Lys Glu Pro Leu His Tyr Tyr Asp Ala Asn Ser
```

```
                145                 150                 155                 160
Ser Pro Ser Ser Pro Leu Ser Ser Met Ser Asn Ile Ser Glu Lys
                165                 170                 175
Cys Asp Leu Asp Glu Leu Glu Ser Ser Gln Lys Lys Glu Arg Lys Gly
                180                 185                 190
Asn Ser Leu Ser Arg Gly Ser Asn Ser Ser Ser Ser Leu Leu Thr Ser
                195                 200                 205
Arg Ser Pro Phe Thr Lys Leu Val Glu Val Ile Phe Ala Arg Pro Arg
                210                 215                 220
Arg His Asp Val Val Pro Lys Arg Val Ser Leu Tyr Ile Asp Tyr Lys
225                 230                 235                 240
Pro His Ser Ser Ser His Leu Lys Glu Glu Asp Asp Leu Val Glu Glu
                245                 250                 255
Ile Leu Lys Arg Ser Tyr Lys Asn Thr Arg Arg Asn Lys Ser Ile Phe
                260                 265                 270
Val Ile Ile Asn Pro Phe Gly Gly Lys Gly Lys Ala Lys Lys Leu Phe
                275                 280                 285
Met Thr Lys Ala Lys Pro Leu Leu Ala Ser Arg Cys Ser Ile Glu
                290                 295                 300
Val Val Tyr Thr Lys Tyr Pro Gly His Ala Ile Glu Ile Ala Arg Glu
305                 310                 315                 320
Met Asp Ile Asp Lys Tyr Asp Thr Ile Ala Cys Ala Ser Gly Asp Gly
                325                 330                 335
Ile Pro His Glu Val Ile Asn Gly Leu Tyr Gln Arg Pro Asp His Val
                340                 345                 350
Lys Ala Phe Asn Asn Ile Ala Ile Thr Glu Ile Pro Cys Gly Ser Gly
                355                 360                 365
Asn Ala Met Ser Val Ser Cys His Trp Thr Asn Asn Pro Ser Tyr Ser
                370                 375                 380
Thr Leu Cys Leu Ile Lys Ser Ile Glu Thr Arg Ile Asp Leu Met Cys
385                 390                 395                 400
Cys Ser Gln Pro Ser Tyr Ala Arg Glu His Pro Lys Leu Ser Phe Leu
                405                 410                 415
Ser Gln Thr Tyr Gly Leu Ile Ala Glu Thr Asp Ile Asn Thr Glu Phe
                420                 425                 430
Ile Arg Trp Met Gly Pro Ala Arg Phe Glu Leu Gly Val Ala Phe Asn
                435                 440                 445
Ile Ile Gln Lys Lys Lys Tyr Pro Cys Glu Ile Tyr Val Lys Tyr Ala
                450                 455                 460
Ala Lys Ser Lys Asn Glu Leu Lys Asn His Tyr Leu Glu His Lys Asn
465                 470                 475                 480
Lys Gly Ser Leu Glu Phe Gln His Ile Thr Met Asn Lys Asp Asn Glu
                485                 490                 495
Asp Cys Asp Asn Tyr Asn Tyr Glu Asn Glu Tyr Glu Thr Glu Asn Glu
                500                 505                 510
Asp Glu Asp Glu Asp Ala Asp Ala Asp Glu Asp Ser His Leu Ile
                515                 520                 525
Ser Arg Asp Leu Ala Asp Ser Ser Ala Asp Gln Ile Lys Glu Glu Asp
                530                 535                 540
Phe Lys Ile Lys Tyr Pro Leu Asp Glu Gly Ile Pro Ser Asp Trp Glu
545                 550                 555                 560
Arg Leu Asp Pro Asn Ile Ser Asn Asn Leu Gly Ile Phe Tyr Thr Gly
                565                 570                 575
```

```
Lys Met Pro Tyr Val Ala Ala Asp Thr Lys Phe Phe Pro Ala Ala Leu
            580                 585                 590

Pro Ser Asp Gly Thr Met Asp Met Val Ile Thr Asp Ala Arg Thr Ser
            595                 600                 605

Leu Thr Arg Met Ala Pro Ile Leu Leu Gly Leu Asp Lys Gly Ser His
        610                 615                 620

Val Leu Gln Pro Glu Val Leu His Ser Lys Ile Leu Ala Tyr Lys Ile
625                 630                 635                 640

Ile Pro Lys Leu Gly Asn Gly Leu Phe Ser Val Asp Gly Glu Lys Phe
                645                 650                 655

Pro Leu Glu Pro Leu Gln Val Glu Ile Met Pro Arg Leu Cys Lys Thr
            660                 665                 670

Leu Leu Arg Asn Gly Arg Tyr Val Asp Thr Asp Phe Asp Ser Met
        675                 680                 685

<210> SEQ ID NO 13
<211> LENGTH: 1038
<212> TYPE: DNA
<213> ORGANISM: Saccharomyces cerevisiae

<400> SEQUENCE: 13
atgaacacta ccacatctac tgttatagca gcagttgccg accagttcca gtctttgaac      60
tcttcttctt catgtttctt gaaggttcat gttccttcca ttgagaaccc attcggtatt     120
gaattatggc caattttctc caaagtgttt gaatacttta gtggctatcc agctgagcaa     180
ttcgagttta ttcacaataa gactttcttg gctaacgggt atcatgctgt tagtattatt     240
atcgtttatt acattattat ctttggtggc caagctatct tacgcgcctt gaacgcctct     300
ccattaaagt ttaaattgct tttcgagata cacaacttgt ttttgacttc tatttctcta     360
gttttatggt tgctgatgtt agaacagttg gttcctatgg tttatcacaa cggtctattc     420
tggtctatct gctctaagga agccttcgca ccaaaattag ttactcttta ctatttgaac     480
tatttgacca aattcgtaga attgattgac actgtgtttt tagttttgag aagaaagaag     540
ttattgtttt tgcacactta ccatcacggt gccaccgctt tgttgtgcta cactcaatta     600
attggtcgta cttctgttga atgggtagtt atcctactaa acttgggtgt tcacgttatc     660
atgtactggt actacttctt gagttcatgt ggtattagag tttggtggaa gcaatgggtc     720
actagattcc aaattattca atttttgatt gacttggtat tgtttacttt gctacctat     780
acattctatg ctcacaaata cttggacggt atttaccaa acaagggtac ttgttatggt     840
actcaggctg ctgctgctta tgggtatttg attctaacat cttatttgct tttgtttatt     900
tccttctaca tccaatctta caagaaaggt ggtaaaaaga cagtcaagaa ggaatctgaa     960
gtttccggct ccgttgcatc cggttcttct actggtgtca agacctctaa caccaaggtc    1020
tcttccagga aagcttaa                                                   1038

<210> SEQ ID NO 14
<211> LENGTH: 345
<212> TYPE: PRT
<213> ORGANISM: Saccharomyces cerevisiae

<400> SEQUENCE: 14

Met Asn Thr Thr Thr Ser Thr Val Ile Ala Ala Val Ala Asp Gln Phe
1               5                   10                  15

Gln Ser Leu Asn Ser Ser Ser Ser Cys Phe Leu Lys Val His Val Pro
            20                  25                  30
```

```
Ser Ile Glu Asn Pro Phe Gly Ile Glu Leu Trp Pro Ile Phe Ser Lys
            35                  40                  45

Val Phe Glu Tyr Phe Ser Gly Tyr Pro Ala Glu Gln Phe Glu Phe Ile
 50                  55                  60

His Asn Lys Thr Phe Leu Ala Asn Gly Tyr His Ala Val Ser Ile Ile
 65                  70                  75                  80

Ile Val Tyr Tyr Ile Ile Ile Phe Gly Gly Gln Ala Ile Leu Arg Ala
                    85                  90                  95

Leu Asn Ala Ser Pro Leu Lys Phe Lys Leu Leu Phe Glu Ile His Asn
                100                 105                 110

Leu Phe Leu Thr Ser Ile Ser Leu Val Leu Trp Leu Leu Met Leu Glu
            115                 120                 125

Gln Leu Val Pro Met Val Tyr His Asn Gly Leu Phe Trp Ser Ile Cys
130                 135                 140

Ser Lys Glu Ala Phe Ala Pro Lys Leu Val Thr Leu Tyr Tyr Leu Asn
145                 150                 155                 160

Tyr Leu Thr Lys Phe Val Glu Leu Ile Asp Thr Val Phe Leu Val Leu
                165                 170                 175

Arg Arg Lys Lys Leu Leu Phe Leu His Thr Tyr His His Gly Ala Thr
                180                 185                 190

Ala Leu Leu Cys Tyr Thr Gln Leu Ile Gly Arg Thr Ser Val Glu Trp
            195                 200                 205

Val Val Ile Leu Leu Asn Leu Gly Val His Val Ile Met Tyr Trp Tyr
210                 215                 220

Tyr Phe Leu Ser Ser Cys Gly Ile Arg Val Trp Trp Lys Gln Trp Val
225                 230                 235                 240

Thr Arg Phe Gln Ile Ile Gln Phe Leu Ile Asp Leu Val Phe Val Tyr
                245                 250                 255

Phe Ala Thr Tyr Thr Phe Tyr Ala His Lys Tyr Leu Asp Gly Ile Leu
                260                 265                 270

Pro Asn Lys Gly Thr Cys Tyr Gly Thr Gln Ala Ala Ala Ala Tyr Gly
            275                 280                 285

Tyr Leu Ile Leu Thr Ser Tyr Leu Leu Leu Phe Ile Ser Phe Tyr Ile
290                 295                 300

Gln Ser Tyr Lys Lys Gly Gly Lys Lys Thr Val Lys Lys Glu Ser Glu
305                 310                 315                 320

Val Ser Gly Ser Val Ala Ser Gly Ser Ser Thr Gly Val Lys Thr Ser
                325                 330                 335

Asn Thr Lys Val Ser Ser Arg Lys Ala
                340                 345

<210> SEQ ID NO 15
<211> LENGTH: 1020
<212> TYPE: DNA
<213> ORGANISM: Saccharomyces cerevisiae

<400> SEQUENCE: 15
atgccattac ctccgtcaac attgaaccag aaatctaata gagtctactc tgtagctagg      60
gtgtacaaga atgcctgcga ggagagacca caagaatact gggactacga acaagggtg     120 accatcgatt ggggaaagat ttccaattac gaattatca acaaaattgg aagagggaaa     180
tattccgaag tgttcagcgg tagatgtatt gtaacaacc agaagtgtgt tattaaagtt     240
ttaaaaccag ttaaaatgaa aaaaatttat agagagttga aaattctgac caatctaaca     300
```

```
ggcggcccca atgttgttgg cctttatgat atagtacaag acgctgactc caaaatacct    360
gctttgatct tgaggaaat  caaaatgtt  gatttcagaa cttatatcc  tacattcaaa    420
cttcctgaca tccagtatta tttcacgcaa ttattgattg cgttagacta ctgtcactcc    480
atgggcataa tgcacagaga cgtaaagcct cagaatgtca tgattgatcc tacggaacgt    540
aaactaaggc tgatcgattg gggcctggcg gagttctacc atccaggtgt agattacaac    600
gttcgtgtcg cttcgcgtta ccacaaggga ccagaacttt tagtaaactt gaaccaatat    660
gactactccc tagacttatg gtcagtagga tgcatgctag cagctattgt cttcaaaaaa    720
gaacctttt  tcaaagggtc gtctaatcca gatcaactgg taagattgc  cacagtacta    780
ggaaccaagg aactgttagg ctatttgggt aagtacgggt tgcacttacc atctgaatac    840
gacaacatta tgagagactt tacaaaaaaa tcgtggacac actttataac ctccgagacc    900
aaattagctg ttcctgaagt ggttgattta atcgacaatt tattaaggta tgaccatcaa    960
gaaagattaa cagcaaagga ggctatggat cataagtttt tcaaaacgaa gtttgaataa   1020
```

```
<210> SEQ ID NO 16
<211> LENGTH: 339
<212> TYPE: PRT
<213> ORGANISM: Saccharomyces cerevisiae

<400> SEQUENCE: 16

Met Pro Leu Pro Pro Ser Thr Leu Asn Gln Lys Ser Asn Arg Val Tyr
1               5                   10                  15

Ser Val Ala Arg Val Tyr Lys Asn Ala Cys Glu Glu Arg Pro Gln Glu
            20                  25                  30

Tyr Trp Asp Tyr Glu Gln Gly Val Thr Ile Asp Trp Gly Lys Ile Ser
        35                  40                  45

Asn Tyr Glu Ile Ile Asn Lys Ile Gly Arg Gly Lys Tyr Ser Glu Val
    50                  55                  60

Phe Ser Gly Arg Cys Ile Val Asn Asn Gln Lys Cys Val Ile Lys Val
65                  70                  75                  80

Leu Lys Pro Val Lys Met Lys Lys Ile Tyr Arg Glu Leu Lys Ile Leu
                85                  90                  95

Thr Asn Leu Thr Gly Gly Pro Asn Val Val Gly Leu Tyr Asp Ile Val
            100                 105                 110

Gln Asp Ala Asp Ser Lys Ile Pro Ala Leu Ile Phe Glu Glu Ile Lys
        115                 120                 125

Asn Val Asp Phe Arg Thr Leu Tyr Pro Thr Phe Lys Leu Pro Asp Ile
    130                 135                 140

Gln Tyr Tyr Phe Thr Gln Leu Leu Ile Ala Leu Asp Tyr Cys His Ser
145                 150                 155                 160

Met Gly Ile Met His Arg Asp Val Lys Pro Gln Asn Val Met Ile Asp
                165                 170                 175

Pro Thr Glu Arg Lys Leu Arg Leu Ile Asp Trp Gly Leu Ala Glu Phe
            180                 185                 190

Tyr His Pro Gly Val Asp Tyr Asn Val Arg Val Ala Ser Arg Tyr His
        195                 200                 205

Lys Gly Pro Glu Leu Leu Val Asn Leu Asn Gln Tyr Asp Tyr Ser Leu
    210                 215                 220

Asp Leu Trp Ser Val Gly Cys Met Leu Ala Ala Ile Val Phe Lys Lys
225                 230                 235                 240

Glu Pro Phe Phe Lys Gly Ser Ser Asn Pro Asp Gln Leu Val Lys Ile
                245                 250                 255
```

```
Ala Thr Val Leu Gly Thr Lys Glu Leu Leu Gly Tyr Leu Gly Lys Tyr
                260                 265                 270

Gly Leu His Leu Pro Ser Glu Tyr Asp Asn Ile Met Arg Asp Phe Thr
            275                 280                 285

Lys Lys Ser Trp Thr His Phe Ile Thr Ser Gly Thr Lys Leu Ala Val
        290                 295                 300

Pro Glu Val Val Asp Leu Ile Asp Asn Leu Leu Arg Tyr Asp His Gln
305                 310                 315                 320

Glu Arg Leu Thr Ala Lys Glu Ala Met Asp His Lys Phe Phe Lys Thr
                325                 330                 335

Lys Phe Glu

<210> SEQ ID NO 17
<211> LENGTH: 651
<212> TYPE: DNA
<213> ORGANISM: Saccharomyces cerevisiae

<400> SEQUENCE: 17
atgattgacc gcactaaaaa cgaatctcca gcttttgaag agtctccgct taccccaat      60 gtgtctaacc tgaaaccatt cccttctcaa agcaacaaaa tatccactcc agtgaccgac    120
cataggagaa gacggtcatc cagcgtaata tcacatgtgg aacaggaaac cttcgaagac    180
gaaaatgacc agcagatgct tcccaacatg aacgctacgt gggtcgacca gcgaggcgcg    240
tggttgattc atatcgtcgt aatagtactc ttgaggctct tctactcctt gttcgggtcg    300
acgcccaaat ggacgtggac tttaacaaac atgacctaca tcatcggatt ctatatcatg    360
ttccaccttg tcaaaggtac gcccttcgac tttaacggtg gtgcgtacga caacctgacc    420
atgtgggagc agattaacga tgagactttg tacacaccca ctagaaaatt tctgctgatt    480
gtacccattg tgttgttcct gattagcaac cagtactacc gcaacgacat gacactattc    540
ctctccaacc tcgccgtgac ggtgcttatt ggtgtcgttc ctaagctggg aattacgcat    600
agactaagaa tatccatccc tggtattacg ggccgtgctc aaattagtta g             651

<210> SEQ ID NO 18
<211> LENGTH: 216
<212> TYPE: PRT
<213> ORGANISM: Saccharomyces cerevisiae

<400> SEQUENCE: 18

Met Ile Asp Arg Thr Lys Asn Glu Ser Pro Ala Phe Glu Glu Ser Pro
1               5                   10                  15

Leu Thr Pro Asn Val Ser Asn Leu Lys Pro Phe Pro Ser Gln Ser Asn
            20                  25                  30

Lys Ile Ser Thr Pro Val Thr Asp His Arg Arg Arg Ser Ser Ser Ser
        35                  40                  45

Val Ile Ser His Val Glu Gln Glu Thr Phe Glu Asp Glu Asn Asp Gln
    50                  55                  60

Gln Met Leu Pro Asn Met Asn Ala Thr Trp Val Asp Gln Arg Gly Ala
65                  70                  75                  80

Trp Leu Ile His Ile Val Val Ile Val Leu Leu Arg Leu Phe Tyr Ser
                85                  90                  95

Leu Phe Gly Ser Thr Pro Lys Trp Thr Trp Thr Leu Thr Asn Met Thr
            100                 105                 110

Tyr Ile Ile Gly Phe Tyr Ile Met Phe His Leu Val Lys Gly Thr Pro
        115                 120                 125
```

Phe Asp Phe Asn Gly Gly Ala Tyr Asp Asn Leu Thr Met Trp Glu Gln
    130                 135                 140

Ile Asn Asp Glu Thr Leu Tyr Thr Pro Thr Arg Lys Phe Leu Leu Ile
145                 150                 155                 160

Val Pro Ile Val Leu Phe Leu Ile Ser Asn Gln Tyr Tyr Arg Asn Asp
                165                 170                 175

Met Thr Leu Phe Leu Ser Asn Leu Ala Val Thr Val Leu Ile Gly Val
            180                 185                 190

Val Pro Lys Leu Gly Ile Thr His Arg Leu Arg Ile Ser Ile Pro Gly
        195                 200                 205

Ile Thr Gly Arg Ala Gln Ile Ser
    210                 215

<210> SEQ ID NO 19
<211> LENGTH: 1083
<212> TYPE: DNA
<213> ORGANISM: Saccharomyces cerevisiae

<400> SEQUENCE: 19
atgtcgatag tctacaataa aacaccatta ttacgtcaat tcttcccgg aaaggcttct      60
gcacaatttt tcttgaaata tgaatgcctt caaccaagtg gctccttcaa aagtagagga    120
atcggtaatc tcatcatgaa aagtgccatt cgaattcaaa aggacggtaa aagatctcct    180
caggttttcg ctagttctgg cggtaatgcc ggttttgctg ctgcaacagc atgtcaaaga    240
ctgtctctac catgtacagt cgtggttcct acagcgacaa agaagagaat ggtagataaa    300
atcaggaaca ccggtgccca ggttatcgtg agtggtgcct actggaaaga agcagatact    360
ttttttaaaaa caaatgtcat gaataaaata gactctcagg tcattgagcc catttatgtt    420
catcccttcg ataatccgga tatttgggaa ggacattcat ctatgataga tgaaatagta    480
caagatttga atcgcaaca tatttccgta ataaggtta aaggcatagt atgcagcgtt    540
ggtggaggtg gtttatacaa tggtattatt caaggtttgg aaaggtatgg tttagctgat    600
aggatcccta ttgtgggggt ggaaacgaat ggatgtcatg ttttcaatac ttctttgaaa    660
ataggccaac cagttcaatt caagaagata acaagtattg ctacttctct aggaacggcc    720
gtgatctcta atcaaacttt cgaatacgct cgcaaataca acaccagatc cgttgtaata    780
gaggacaaag atgttattga aacctgtctt aaatatacac atcaattcaa tatggtgatt    840
gaaccggcat gtggcgccgc attgcatttg ggttacaaca ctaagatcct agaaaatgca    900
ctgggctcaa aattagctgc ggatgacatt gtgataatta ttgcttgtgg cggctcctct    960
aatactataa aggacttgga agaagcgttg gatagcatga aaaaaaaga cactcctgta   1020
atagaagtcg ctgacaattt catatttcca gaaaaaaata ttgtgaattt aaaaagtgct   1080
tga                                                                1083

<210> SEQ ID NO 20
<211> LENGTH: 360
<212> TYPE: PRT
<213> ORGANISM: Saccharomyces cerevisiae

<400> SEQUENCE: 20

Met Ser Ile Val Tyr Asn Lys Thr Pro Leu Leu Arg Gln Phe Phe Pro
1               5                   10                  15

Gly Lys Ala Ser Ala Gln Phe Phe Leu Lys Tyr Glu Cys Leu Gln Pro
            20                  25                  30

Ser Gly Ser Phe Lys Ser Arg Gly Ile Gly Asn Leu Ile Met Lys Ser
            35                  40                  45

Ala Ile Arg Ile Gln Lys Asp Gly Lys Arg Ser Pro Gln Val Phe Ala
 50                  55                  60

Ser Ser Gly Gly Asn Ala Gly Phe Ala Ala Thr Ala Cys Gln Arg
 65                  70                  75                  80

Leu Ser Leu Pro Cys Thr Val Val Pro Thr Ala Thr Lys Lys Arg
                 85                  90                  95

Met Val Asp Lys Ile Arg Asn Thr Gly Ala Gln Val Ile Val Ser Gly
            100                 105                 110

Ala Tyr Trp Lys Glu Ala Asp Thr Phe Leu Lys Thr Asn Val Met Asn
         115                 120                 125

Lys Ile Asp Ser Gln Val Ile Glu Pro Ile Tyr Val His Pro Phe Asp
         130                 135                 140

Asn Pro Asp Ile Trp Glu Gly His Ser Ser Met Ile Asp Glu Ile Val
145                 150                 155                 160

Gln Asp Leu Lys Ser Gln His Ile Ser Val Asn Lys Val Lys Gly Ile
                 165                 170                 175

Val Cys Ser Val Gly Gly Gly Gly Leu Tyr Asn Gly Ile Ile Gln Gly
             180                 185                 190

Leu Glu Arg Tyr Gly Leu Ala Asp Arg Ile Pro Ile Val Gly Val Glu
         195                 200                 205

Thr Asn Gly Cys His Val Phe Asn Thr Ser Leu Lys Ile Gly Gln Pro
         210                 215                 220

Val Gln Phe Lys Lys Ile Thr Ser Ile Ala Thr Ser Leu Gly Thr Ala
225                 230                 235                 240

Val Ile Ser Asn Gln Thr Phe Glu Tyr Ala Arg Lys Tyr Asn Thr Arg
                 245                 250                 255

Ser Val Val Ile Glu Asp Lys Asp Val Ile Glu Thr Cys Leu Lys Tyr
             260                 265                 270

Thr His Gln Phe Asn Met Val Ile Glu Pro Ala Cys Gly Ala Ala Leu
         275                 280                 285

His Leu Gly Tyr Asn Thr Lys Ile Leu Glu Asn Ala Leu Gly Ser Lys
         290                 295                 300

Leu Ala Ala Asp Asp Ile Val Ile Ile Ala Cys Gly Gly Ser Ser
305                 310                 315                 320

Asn Thr Ile Lys Asp Leu Glu Glu Ala Leu Asp Ser Met Arg Lys Lys
                 325                 330                 335

Asp Thr Pro Val Ile Glu Val Ala Asp Asn Phe Ile Phe Pro Glu Lys
             340                 345                 350

Asn Ile Val Asn Leu Lys Ser Ala
         355                 360

<210> SEQ ID NO 21
<211> LENGTH: 978
<212> TYPE: DNA
<213> ORGANISM: Pichia ciferrii

<400> SEQUENCE: 21
atgtcctccc atcaattctt gatcaatcaa actactttgg ctgctccacc agttcatttg     60
gttgaaaaac catctttgat caacggtatc ccagataaca ttttggcttt gattgctcca    120
gttatcgcct actattctta ctctggtttc ttctacgtta tcgacacctt ggaaattgcc    180
gaattataca gaattcaccc accagaagaa gtctccagta gaaacaaagc tactaagttc    240

```
gatgttttga aggacgttgt cttgcaacac ttcatccaat ctgttgttgg ttacatcttc    300
acctacttcg acccaattca atacactggt gatgaagaat atcaagcctg aagttgcaa    360 caaactttgc cattttttgcc tttcgatgtt gcttactact ggaatatgta tggttggtcc    420
tgtttgaaga ttggtttggc cttcttgatt atcgactctt ggcaatattg gttgcacaga    480
atcatgcatt tgaacaagac cttgtacaaa agattccact ccagacacca cagattatat    540
gttccatatg cttttggtgc cttgtataac gatccattcg aaggttttt gttggatact     600 ttgggtactg gtattgctgc tatcgttact caattgactc aagagaatc cattgtcttg     660 tacactttct ctaccttgaa accgttgat gatcattgcg ttattcctt gccatatgat      720 ccattccaaa tcttgttccc aaacaactcc atctaccatg atatccatca tcaacaattc    780
ggtatcaaga ccaacttctc tcaaccattt ttcacccatt gggacgtttt ctctaacacc    840
agatacaaag aaatcgacga atacagagaa aagcaaaagg ctattaccat tgccaagtac    900
aaagaatttt tacacgacag agaaatcgcc aagcaaaaga gaaagctga aatctacaag     960 gacaaaaaga ctgattaa                                                   978
```

<210> SEQ ID NO 22
<211> LENGTH: 325
<212> TYPE: PRT
<213> ORGANISM: Pichia ciferrii

<400> SEQUENCE: 22

```
Met Ser Ser His Gln Phe Leu Ile Asn Gln Thr Thr Leu Ala Ala Pro
1               5                   10                  15

Pro Val His Leu Val Glu Lys Pro Ser Leu Ile Asn Gly Ile Pro Asp
            20                  25                  30

Asn Ile Leu Ala Leu Ile Ala Pro Val Ile Ala Tyr Tyr Ser Tyr Ser
        35                  40                  45

Gly Phe Phe Tyr Val Ile Asp Thr Leu Glu Ile Ala Glu Leu Tyr Arg
    50                  55                  60

Ile His Pro Pro Glu Glu Val Ser Ser Arg Asn Lys Ala Thr Lys Phe
65                  70                  75                  80

Asp Val Leu Lys Asp Val Val Leu Gln His Phe Ile Gln Ser Val Val
                85                  90                  95

Gly Tyr Ile Phe Thr Tyr Phe Asp Pro Ile Gln Tyr Thr Gly Asp Glu
            100                 105                 110

Glu Tyr Gln Ala Trp Lys Leu Gln Gln Thr Leu Pro Phe Leu Pro Phe
        115                 120                 125

Asp Val Ala Tyr Tyr Trp Asn Met Tyr Gly Trp Ser Cys Leu Lys Ile
    130                 135                 140

Gly Leu Ala Phe Leu Ile Ile Asp Ser Trp Gln Tyr Trp Leu His Arg
145                 150                 155                 160

Ile Met His Leu Asn Lys Thr Leu Tyr Lys Arg Phe His Ser Arg His
                165                 170                 175

His Arg Leu Tyr Val Pro Tyr Ala Phe Gly Ala Leu Tyr Asn Asp Pro
            180                 185                 190

Phe Glu Gly Phe Leu Leu Asp Thr Leu Gly Thr Gly Ile Ala Ala Ile
        195                 200                 205

Val Thr Gln Leu Thr Pro Arg Glu Ser Ile Val Leu Tyr Thr Phe Ser
    210                 215                 220

Thr Leu Lys Thr Val Asp Asp His Cys Gly Tyr Ser Leu Pro Tyr Asp
225                 230                 235                 240
```

-continued

```
Pro Phe Gln Ile Leu Phe Pro Asn Asn Ser Ile Tyr His Asp Ile His
            245                 250                 255

His Gln Gln Phe Gly Ile Lys Thr Asn Phe Ser Gln Pro Phe Phe Thr
        260                 265                 270

His Trp Asp Val Phe Ser Asn Thr Arg Tyr Lys Glu Ile Asp Glu Tyr
    275                 280                 285

Arg Glu Lys Gln Lys Ala Ile Thr Ile Ala Leu Tyr Lys Glu Phe Leu
    290                 295                 300

His Asp Arg Glu Ile Ala Lys Gln Lys Lys Lys Ala Glu Ile Tyr Lys
305                 310                 315                 320

Asp Lys Lys Thr Asp
            325

<210> SEQ ID NO 23
<211> LENGTH: 65
<212> TYPE: DNA
<213> ORGANISM: Artificial Sequence
<220> FEATURE:
<223> OTHER INFORMATION: primer

<400> SEQUENCE: 23
taagtgctgg atagacaaga gacaggaaaa ttaaccagcg agatgccagc tgaagcttcg      60
tacgc                                                                 65

<210> SEQ ID NO 24
<211> LENGTH: 67
<212> TYPE: DNA
<213> ORGANISM: Artificial Sequence
<220> FEATURE:
<223> OTHER INFORMATION: primer

<400> SEQUENCE: 24
tcaagggcaa attgatgctt caacgaaaaa gttattggat tttcagcata ggccactagt      60
ggatctg                                                               67

<210> SEQ ID NO 25
<211> LENGTH: 65
<212> TYPE: DNA
<213> ORGANISM: Artificial Sequence
<220> FEATURE:
<223> OTHER INFORMATION: primer

<400> SEQUENCE: 25
aagactatac cattataaaa acgcataaga aacagtttca tcatgccagc tgaagcttcg      60
tacgc                                                                 65

<210> SEQ ID NO 26
<211> LENGTH: 67
<212> TYPE: DNA
<213> ORGANISM: Artificial Sequence
<220> FEATURE:
<223> OTHER INFORMATION: primer

<400> SEQUENCE: 26
atatatatat atatatacat atatgcgtat aggcagagcc aactagcata ggccactagt      60
ggatctg                                                               67

<210> SEQ ID NO 27
<211> LENGTH: 68
<212> TYPE: DNA
<213> ORGANISM: Artificial Sequence
```

```
<220> FEATURE:
<223> OTHER INFORMATION: primer

<400> SEQUENCE: 27
aaatagaagg aacaataaac ctaaaagaat agaagaaaca gaatgccagc tgaagcttcg    60
tacgctgc                                                            68

<210> SEQ ID NO 28
<211> LENGTH: 69
<212> TYPE: DNA
<213> ORGANISM: Artificial Sequence
<220> FEATURE:
<223> OTHER INFORMATION: primer

<400> SEQUENCE: 28
tggtggaaaa agaattgcct tgctaagagt attgttgtcc aattaccgca taggccacta    60
gtggatctg                                                           69

<210> SEQ ID NO 29
<211> LENGTH: 65
<212> TYPE: DNA
<213> ORGANISM: Artificial Sequence
<220> FEATURE:
<223> OTHER INFORMATION: primer

<400> SEQUENCE: 29
aagtctagca gcgaaaagta cgcgaagaat ctactataga taatgccagc tgaagcttcg    60
tacgc                                                               65

<210> SEQ ID NO 30
<211> LENGTH: 67
<212> TYPE: DNA
<213> ORGANISM: Artificial Sequence
<220> FEATURE:
<223> OTHER INFORMATION: primer

<400> SEQUENCE: 30
ttttacaaaa aaatcatttt tgaaggaaaa tataacgtta atctagcata ggccactagt    60
ggatctg                                                             67

<210> SEQ ID NO 31
<211> LENGTH: 65
<212> TYPE: DNA
<213> ORGANISM: Artificial Sequence
<220> FEATURE:
<223> OTHER INFORMATION: primer

<400> SEQUENCE: 31
aaaccacaaa tagtgtaaga tttaaacagt aagccaaaag agatgccagc tgaagcttcg    60
tacgc                                                               65

<210> SEQ ID NO 32
<211> LENGTH: 67
<212> TYPE: DNA
<213> ORGANISM: Artificial Sequence
<220> FEATURE:
<223> OTHER INFORMATION: primer

<400> SEQUENCE: 32
ttgattaatt gttcagtacg aaggaaaaga ttaagtaaag tgtcagcata ggccactagt    60
ggatctg                                                             67
```

<210> SEQ ID NO 33
<211> LENGTH: 66
<212> TYPE: DNA
<213> ORGANISM: Artificial Sequence
<220> FEATURE:
<223> OTHER INFORMATION: primer

<400> SEQUENCE: 33
ttattcggct tttttccgtt tgtttacgaa acataaacag tcatgccagc tgaagcttcg    60
tacgct    66

<210> SEQ ID NO 34
<211> LENGTH: 67
<212> TYPE: DNA
<213> ORGANISM: Artificial Sequence
<220> FEATURE:
<223> OTHER INFORMATION: primer

<400> SEQUENCE: 34
tttttctttt tcattcgct gtcaaaaatt ctcgcttcct atttagcata ggccactagt    60
ggatctg    67

<210> SEQ ID NO 35
<211> LENGTH: 36
<212> TYPE: DNA
<213> ORGANISM: Artificial Sequence
<220> FEATURE:
<223> OTHER INFORMATION: primer

<400> SEQUENCE: 35
gatggcgcgc caacaaaccg aagttatctg atgtag    36

<210> SEQ ID NO 36
<211> LENGTH: 46
<212> TYPE: DNA
<213> ORGANISM: Artificial Sequence
<220> FEATURE:
<223> OTHER INFORMATION: primer

<400> SEQUENCE: 36
gaagcttcag ctggcggccg ccatgattta tcttcgtttc ctgcag    46

<210> SEQ ID NO 37
<211> LENGTH: 49
<212> TYPE: DNA
<213> ORGANISM: Artificial Sequence
<220> FEATURE:
<223> OTHER INFORMATION: primer

<400> SEQUENCE: 37
ctagtggcct atgcggccgc taaaaaactg tattataagt aaatgcatg    49

<210> SEQ ID NO 38
<211> LENGTH: 32
<212> TYPE: DNA
<213> ORGANISM: Artificial Sequence
<220> FEATURE:
<223> OTHER INFORMATION: primer

<400> SEQUENCE: 38
gatggcgcgc ccccaagcct tgtcccaagg ca    32

<210> SEQ ID NO 39
<211> LENGTH: 33

```
<212> TYPE: DNA
<213> ORGANISM: Artificial Sequence
<220> FEATURE:
<223> OTHER INFORMATION: primer

<400> SEQUENCE: 39
gatggcgcgc cccacgacgc tttgtcttca ttc                              33

<210> SEQ ID NO 40
<211> LENGTH: 38
<212> TYPE: DNA
<213> ORGANISM: Artificial Sequence
<220> FEATURE:
<223> OTHER INFORMATION: primer

<400> SEQUENCE: 40
tcactagcgg ccgccatctt tgccttcgtt tatcttgc                         38

<210> SEQ ID NO 41
<211> LENGTH: 39
<212> TYPE: DNA
<213> ORGANISM: Artificial Sequence
<220> FEATURE:
<223> OTHER INFORMATION: primer

<400> SEQUENCE: 41
aagatggcgg ccgctagtga caccgattat ttaaagctg                        39

<210> SEQ ID NO 42
<211> LENGTH: 39
<212> TYPE: DNA
<213> ORGANISM: Artificial Sequence
<220> FEATURE:
<223> OTHER INFORMATION: primer

<400> SEQUENCE: 42
aagatggcgg ccgctagtga caccgattat ttaaagctg                        39

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
gatggcgcgc cctcaggtat cgtaagatgc aagag                            35

<210> SEQ ID NO 44
<211> LENGTH: 38
<212> TYPE: DNA
<213> ORGANISM: Artificial Sequence
<220> FEATURE:
<223> OTHER INFORMATION: primer

<400> SEQUENCE: 44
tttttagcgg ccgccattag aatggtatat ccttgaaa                         38

<210> SEQ ID NO 45
<211> LENGTH: 44
<212> TYPE: DNA
<213> ORGANISM: Artificial Sequence
<220> FEATURE:
<223> OTHER INFORMATION: primer

<400> SEQUENCE: 45
```
ctaatggcgg ccgctaaaaa gattctcttt ttttatgata tttg    44

<210> SEQ ID NO 46
<211> LENGTH: 34
<212> TYPE: DNA
<213> ORGANISM: Artificial Sequence
<220> FEATURE:
<223> OTHER INFORMATION: primer

<400> SEQUENCE: 46
gatggcgcgc cctacgtcgt taaggccgtt tctg    34

<210> SEQ ID NO 47
<211> LENGTH: 47
<212> TYPE: DNA
<213> ORGANISM: Artificial Sequence
<220> FEATURE:
<223> OTHER INFORMATION: primer

<400> SEQUENCE: 47
agatcttaag gggatatctt aatggggagc gctgattctc ttttggt    47

<210> SEQ ID NO 48
<211> LENGTH: 49
<212> TYPE: DNA
<213> ORGANISM: Artificial Sequence
<220> FEATURE:
<223> OTHER INFORMATION: primer

<400> SEQUENCE: 48
gggaacctcg aggatatcat gtccacaaaa tcatatacca gtagagctg    49

<210> SEQ ID NO 49
<211> LENGTH: 3638
<212> TYPE: DNA
<213> ORGANISM: Artificial Sequence
<220> FEATURE:
<223> OTHER INFORMATION: plasmid

<400> SEQUENCE: 49
cggtgcgggc ctcttcgcta ttacgccagc tggcgaaagg gggatgtgct gcaaggcgat    60
taagttgggt aacgccaggg ttttcccagt cacgacgttg taaaacgacg gccagtgaat   120
tgtaatacga ctcactatag ggcgacccct aggatctaag cattggcgcg ccccggctgt   180
ctgccatgct gcccggtgta ccgacataac cgccggtggc atagccgcgc atacgcgtct   240
ccagcgtgtt ttatctctgc gagcataatg cctgcgtcat ccgccagcag gagctggact   300
ttactgatgc ccgttatatc tgcgaaaaga ccgggatctg gacccgtgat ggcattctct   360
ggttttcgtc atccggtgaa gagattgagc cacctgacag tgtgaccttt cacatctgga   420
cagcgtacag cccgttcacc acctgggtgc agattgtcaa agactggatg aaaacgaaag   480
gggatacggg aaaacgtaaa accttcgtaa acaccacgct cggtgagacg tgggaggcga   540
aaattggcga acgtccggat gctgaagtga tggcagagcg gaaagagcat tattcagcgc   600
ccgttcctga ccgtgtggct tacctgaccg ccggtatcga ctcccagctg accgctacg    660
aaatgcgcgt atggggatgg gggccgggtg aggaaagctg gctgattgac ggcagatta    720
ttatgggccg ccacgacgat gaacagacgc tgctgcgtgt ggatgaggcc atcaataaaa   780
cctatacccg ccggaatggt gcagaaatgt cgatatcccg tatctgctgg gatactggac   840
gcgttttccc gtctttcagt gccttgttca gttcttcctg acgggcggta tatttctcca   900
gcttggcgcg cctaagactt agatcttaag gggatatcct cgaggttccc tttagtgagg   960

```
gttaattgcg agcttggcgt aatcatggtc atagctgttt cctgtgtgaa attgttatcc   1020
gctcacaatt ccacacaaca tacgagccgg aagcataaag tgtaaagcct ggggtgccta   1080
atgagtgagc taactcacat taattgcgtt gcgctcactg cccgctttcc agtcgggaaa   1140
cctgtcgtgc cagctgcatt aatgaatcgg ccaacgcgcg gggagaggcg gtttgcgtat   1200
tgggcgctct tccgcttcct cgctcactga ctcgctgcgc tcggtcgttc ggctgcggcg   1260
agcggtatca gctcactcaa aggcggtaat acggttatcc acagaatcag gggataacgc   1320
aggaaagaac atgtgagcaa aaggccagca aaaggccagg aaccgtaaaa aggccgcgtt   1380
gctggcgttt ttccataggc tccgcccccc tgacgagcat cacaaaaatc gacgctcaag   1440
tcagaggtgg cgaaacccga caggactata aagataccag gcgtttcccc ctggaagctc   1500
cctcgtgcgc tctcctgttc cgaccctgcc gcttaccgga tacctgtccg cctttctccc   1560
ttcgggaagc gtggcgcttt ctcatagctc acgctgtagg tatctcagtt cggtgtaggt   1620
cgttcgctcc aagctgggct gtgtgcacga accccccgtt cagcccgacc gctgcgcctt   1680
atccggtaac tatcgtcttg agtccaaccc ggtaagacac gacttatcgc cactggcagc   1740
agccactggt aacaggatta gcagagcgag gtatgtaggc ggtgctacag agttcttgaa   1800
gtggtggcct aactacggct acactagaag aacagtattt ggtatctgcg ctctgctgaa   1860
gccagttacc ttcggaaaaa gagttggtag ctcttgatcc ggcaaacaaa ccaccgctgg   1920
tagcggtggt ttttttgttt gcaagcagca gattacgcgc agaaaaaaag gatctcaaga   1980
agatcctttg atcttttcta cggggtctga cgctcagtgg aacgaaaact cacgttaagg   2040
gattttggtc atgagattat caaaaaggat cttcacctag atccttttaa attaaaaatg   2100
aagttttaaa tcaatctaaa gtatatatga gtaaacttgg tctgacagtt accaatgctt   2160
aatcagtgag gcacctatct cagcgatctg tctatttcgt tcatccatag ttgcctgact   2220
ccccgtcgtg tagataacta cgatacggga gggcttacca tctggcccca gtgctgcaat   2280
gataccgcga gacccacgct caccggctcc agatttatca gcaataaacc agccagccgg   2340
aagggccgag cgcagaagtg gtcctgcaac tttatccgcc tccatccagt ctattaattg   2400
ttgccgggaa gctagagtaa gtagttcgcc agttaatagt ttgcgcaacg ttgttgccat   2460
tgctacaggc atcgtggtgt cacgctcgtc gtttggtatg gcttcattca gctccggttc   2520
ccaacgatca aggcgagtta catgatcccc catgttgtgc aaaaaagcgg ttagctcctt   2580
cggtcctccg atcgttgtca agtaagtt ggccgcagtg ttatcactca tggttatggc   2640
agcactgcat aattctctta ctgtcatgcc atccgtaaga tgcttttctg tgactggtga   2700
gtactcaacc aagtcattct gagaatagtg tatgcggcga ccgagttgct cttgcccggc   2760
gtcaatacgg ataataccg cgccacatag cagaacttta aaagtgctca tcattggaaa   2820
acgttcttcg gggcgaaaac tctcaaggat cttaccgctg ttgagatcca gttcgatgta   2880
acccactcgt gcacccaact gatcttcagc atcttttact ttcaccagcg tttctgggtg   2940
agcaaaaaca ggaaggcaaa atgccgcaaa aaagggaata agggcgacac ggaaatgttg   3000
aatactcata ctcttccttt ttcaatatta ttgaagcatt tatcagggtt attgtctcat   3060
gagcggatac atatttgaat gtatttagaa aaataaacaa ataggggttc cgcgcacatt   3120
tccccgaaaa gtgccacctg acgcgccctg tagcggcgca ttaagcgcgg cgggtgtggt   3180
ggttacgcgc agcgtgaccg ctacacttgc cagcgcccta gcgcccgctc ctttcgcttt   3240
cttcccttcc tttctcgcca cgttcgccgg ctttccccgt caagctctaa atcgggggct   3300
```

```
ccctttaggg ttccgattta gtgctttacg gcacctcgac cccaaaaaac ttgattaggg    3360
tgatggttca cgtagtgggc catcgccctg atagacggtt tttcgccctt tgacgttgga    3420
gtccacgttc tttaatagtg gactcttgtt ccaaactgga acaacactca accctatctc    3480
ggtctattct tttgatttat aagggatttt gccgatttcg gcctattggt taaaaaatga    3540
gctgatttaa caaaaattta acgcgaattt taacaaaata ttaacgctta caatttgcca    3600
ttcgccattc aggctgcgca actgttggga agggcgat                            3638

<210> SEQ ID NO 50
<211> LENGTH: 3819
<212> TYPE: DNA
<213> ORGANISM: Artificial Sequence
<220> FEATURE:
<223> OTHER INFORMATION: plasmid

<400> SEQUENCE: 50
cggtgcgggc ctcttcgcta ttacgccagc tggcgaaagg gggatgtgct gcaaggcgat      60
taagttgggt aacgccaggg ttttcccagt cacgacgttg taaaacgacg gccagtgaat     120
tgtaatacga ctcactatag ggcgacccct aggatctaag cattggcgcg cccccaagcc     180
ttgtcccaag gcagcgtttt gttcttggaa acgctgccct acacgttcgc tatgcttcaa     240
gaacttttct gagcacttca tgatgcatgt tgttccctta ttggttagct ttgatgttgt     300
gaagtcattg acacagtctg tgaaacatct ttctaccaga ttagagtaca aacgcatgaa     360
atccttcatt tgcttttgtt ccactacttt ttggaactct tgttgttctt tggagttcaa     420
tgcgtccatc tttacagtcc tgtcttattg ttcttgattt gtgccccgta aaatactgtt     480
acttggttct ggcgaggtat tggatagttc ctttttataa aggccatgaa gcttttttctt    540 tccaattttt ttttttcgt cattatagaa atcattacga ccgagattcc cgggtaataa     600
ctgatataat taaattgaag ctctaatttg tgagtttagt atacatgcat ttacttataa     660
tacagttttt tagcggccgc catgatttat cttcgtttcc tgcaggtttt tgttctgtgc     720
agttgggtta agaatactgg gcaatttcat gttttcttcaa caccacatat gcgtatatat     780
accaatctaa gtctgtgctc cttccttcgt tcttccttct gctcggagat taccgaatca     840
aaaaaatttc aaagaaaccg gaatcaaaaa aagaacaaaa aaaaaaaag atgaattgaa     900 aagctttatg gaccctgaaa ccacagccac attaaccttc tttgatggtc aaaacttatc     960
cttcaccata aatatgcctc gcaaaaaagg taattaacat atatagaatt acattatta     1020 tgaaatatca tcactatctc ttagcatctt taatcctttt ctacatcaga taacttcggt    1080
ttgttggcgc gcctaagact tagatcttaa ggggatatcc tcgaggttcc ctttagtgag    1140
ggttaattgc gagcttggcg taatcatggt catagctgtt tcctgtgtga attgttatc     1200 cgctcacaat tccacacaac atacgagccg gaagcataaa gtgtaaagcc tggggtgcct    1260
aatgagtgag ctaactcaca ttaattgcgt tgcgctcact gcccgctttc cagtcgggaa    1320
acctgtcgtg ccagctgcat taatgaatcg gccaacgcgc ggggagaggc ggtttgcgta    1380
ttgggcgctc ttccgcttcc tcgctcactg actcgctgcg ctcggtcgtt cggctgcggc    1440
gagcggtatc agctcactca aaggcggtaa tacggttatc cacagaatca ggggataacg    1500
caggaaagaa catgtgagca aaaggccagc aaaaggccag gaaccgtaaa aaggccgcgt    1560
tgctggcgtt tttccatagg ctccgccccc ctgacgagca tcacaaaaat cgacgctcaa    1620
gtcagaggtg gcgaaacccg acaggactat aaagatacca ggcgtttccc cctggaagct    1680
ccctcgtgcg ctctcctgtt ccgaccctgc cgcttaccgg atacctgtcc gcctttctcc    1740
```

```
cttcgggaag cgtggcgctt tctcatagct cacgctgtag gtatctcagt tcggtgtagg   1800
tcgttcgctc caagctgggc tgtgtgcacg aacccccccgt tcagcccgac cgctgcgcct   1860
tatccggtaa ctatcgtctt gagtccaacc cggtaagaca cgacttatcg ccactggcag   1920
cagccactgg taacaggatt agcagagcga ggtatgtagg cggtgctaca gagttcttga   1980
agtggtggcc taactacggc tacactagaa gaacagtatt tggtatctgc gctctgctga   2040
agccagttac cttcggaaaa agagttggta gctcttgatc cggcaaacaa accaccgctg   2100
gtagcggtgg ttttttttgtt tgcaagcagc agattacgcg cagaaaaaaa ggatctcaag   2160
aagatccttt gatcttttct acggggtctg acgctcagtg gaacgaaaac tcacgttaag   2220
ggattttggt catgagatta tcaaaaagga tcttcaccta gatcctttta aattaaaaat   2280
gaagttttaa atcaatctaa agtatatatg agtaaacttg gtctgacagt taccaatgct   2340
taatcagtga ggcacctatc tcagcgatct gtctatttcg ttcatccata gttgcctgac   2400
tccccgtcgt gtagataact acgatacggg agggcttacc atctggcccc agtgctgcaa   2460
tgataccgcg agacccacgc tcaccggctc cagatttatc agcaataaac cagccagccg   2520
gaagggccga gcgcagaagt ggtcctgcaa ctttatccgc ctccatccag tctattaatt   2580
gttgccggga agctagagta agtagttcgc cagttaatag tttgcgcaac gttgttgcca   2640
ttgctacagg catcgtggtg tcacgctcgt cgtttggtat ggcttcattc agctccggtt   2700
cccaacgatc aaggcgagtt acatgatccc ccatgttgtg caaaaaagcg gttagctcct   2760
tcggtcctcc gatcgttgtc agaagtaagt tggccgcagt gttatcactc atggttatgg   2820
cagcactgca taattctctt actgtcatgc catccgtaag atgcttttct gtgactggtg   2880
agtactcaac caagtcattc tgagaatagt gtatgcggcg accgagttgc tcttgcccgg   2940
cgtcaatacg ggataatacc gcgccacata gcagaacttt aaaagtgctc atcattggaa   3000
aacgttcttc ggggcgaaaa ctctcaagga tcttaccgct gttgagatcc agttcgatgt   3060
aacccactcg tgcacccaac tgatcttcag catcttttac tttcaccagc gtttctgggt   3120
gagcaaaaac aggaaggcaa aatgccgcaa aaaagggaat aagggcgaca cggaaatgtt   3180
gaatactcat actcttcctt tttcaatatt attgaagcat ttatcagggt tattgtctca   3240
tgagcggata catatttgaa tgtatttaga aaaataaaca ataggggtt ccgcgcacat   3300 ttccccgaaa agtgccacct gacgcgcccc gtagcggcgc attaagcgcg gcgggtgtgg   3360
tggttacgcg cagcgtgacc gctacacttg ccagcgccct agcgcccgct cctttcgctt   3420
tcttcccttc ctttctcgcc acgttcgccg gctttccccg tcaagctcta aatcgggggc   3480
tccctttagg gttccgattt agtgctttac ggcacctcga ccccaaaaaa cttgattagg   3540
gtgatggttc acgtagtggg ccatcgccct gatagacggt ttttcgccct ttgacgttgg   3600
agtccacgtt ctttaatagt ggactcttgt tccaaactgg aacaacactc aaccctatct   3660
cggtctattc ttttgattta agggattt tgccgatttc ggcctattgg ttaaaaaatg   3720
agctgattta acaaaaattt aacgcgaatt ttaacaaaat attaacgctt acaatttgcc   3780
attcgccatt caggctgcgc aactgttggg aagggcgat                          3819
```

<210> SEQ ID NO 51
<211> LENGTH: 5389
<212> TYPE: DNA
<213> ORGANISM: Artificial Sequence
<220> FEATURE:
<223> OTHER INFORMATION: plasmid

```
<400> SEQUENCE: 51
cggtgcgggc ctcttcgcta ttacgccagc tggcgaaagg gggatgtgct gcaaggcgat      60
taagttgggt aacgccaggg ttttcccagt cacgacgttg taaaacgacg ccagtgaat     120
tgtaatacga ctcactatag ggcgacccct aggatctaag cattggcgcg ccgcgcacct    180
gcgttgttac cacaactctt atgaggcccg cggacagcat caaactgtaa gattccgcca    240
cattttatac actctggtcc tttaactggc aaaccttcgg gcgtaatgcc caattttcg     300
cctttgtctt ttgccttttt cacttcacgt gcttctggta catacttgca atttatacag    360
tgatgaccgc tgaatttgta tcttccatag catctagcac atactcgatt tttaccactc    420
caatctttat aaaaatactt gattcccttt ctgggacaag caacacagtg ttttagattc    480
ttttttttgtg atatttttaag ctgttctccc acacagcagc ctcgacatga tttcacttct   540
attttgttgc caagcaagaa atttttatgg ccgcggccgc ataggccact agtggatctg    600
atatcaccta taacttcgt atagcataca ttatacgaag ttatattaag ggttctcgag     660
agctcgtttt atttaggttc tatcgaggag aaaaagcgac aagaagagat agaccatgga    720
taaatgatta tgttctaaac actcctcaga agctcatcga actgtcatcc tgcgtgaaga    780
ttaaaatcca acttagaaat ttcgagctta cggagacaat catatgggag aagcaattgg    840
aagatagaaa aaaggtactc ggtacataaa tatatgtgat tctgggtaga agatcggtct    900
gcattggatg gtggtaacgc atttttttac acacattact tgcctcgagc atcaaatggt    960
ggttattcgt ggatctatat cacgtgattt gcttaagaat tgtcgttcat ggtgacactt   1020
ttagcttgga catgattaag ctcatctcaa ttgatgttat ctaaagtcat ttcaactatc   1080
taagatgtgg ttgtgattgg gccattttgt gaaagccagt acgccagcgt caatacactc   1140
ccgtcaatta gttgcaccat gtccacaaaa tcatatacca gtagactgca gactcatgca   1200
agtccggttg catcgaaact tttacgttta atggatgaaa agaagaccaa tttgtgtgct   1260
tctcttgacg ttcgttcgac tgatgagcta ttgaaacttg ttgaaacgtt gggtccatac   1320
atttgccttt tgaaaacaca cgttgatatc ttggatgatt tcagttatga gggtactgtc   1380
gttccattga aagcattggc agagaaatac aagttcttga tatttgagga cagaaaattc   1440
gccgatatcg gtaacacagt caaattacaa tatacatcgg gcgtttaccg tatcgcagaa   1500
tggtctgata tcaccaacgc ccacgggggtt actggtgctg gtattgttgc tggcttgaaa   1560
caaggtgcgc aagaggtcac caaagaacca aggggattat tgatgcttgc tgaattgtct   1620
tccaagggtt ctctagcaca cggtgaatat actaagggta ccgttgatat tgcaaagagt   1680
gataaagatt tcgttattgg gttcattgct cagaacgata tgggaggaag agaagaaggg   1740
tttgattggc taatcatgac cccaggtgta ggtttagacg acaaaggcga tgcattgggt   1800
cagcagtaca gaaccgtcga cgaagttgta agtggtggat cagatatcat cattgttggc   1860
agaggacttt tcgccaaggg tagagatcct aaggttgaag gtgaaagata cagaaatgct   1920
ggatgggaag cgtaccaaaa gagaatcagc gctccccatt aattatacag gaaacttaat   1980
agaacaaatc acatatttaa tctaatagcc acctgcattg gcacggtgca acactacttc   2040
aacttcatct tacaaaaaga tcacgtgatc tgttgtattg gatctctag acctaataac    2100
ttcgtatagc atacattata cgaagttata ttaagggttg tcgacctgca gcgtacgaag   2160
cttcagctgg cggccgcgaa atattctcct ttagagcgct ccatttcttc tatgaagcgt   2220
tttgcggcaa actcacctt c aactgtcatt gggaatgtct tatgatggtt ttttggaatt   2280
attattatcc taccatcaag cgtctgacat tgctgcagat ttctccatct cactttatat   2340
```

```
ttggtggcat tcctaccact tttttccaac agtggtttgg tagggaccct gactgacaat    2400
ttatgacctg cagtacattg taatgcaaga cgctgataaa ctgttctacg cctgggatct    2460
aacctaccag gttcacccttc aaaagctctg tgtttggttt tttgctgtat attatagatt   2520
ttctgatagc cctgtgtgac atttatgacg cgggcagcgg agccatctgc gcacataacg    2580
taagagttag ccgtgacgtt tgcgatgtct ttaatttcac cgttagccat cagaatagtc    2640
gtgttttcag aaagcggcgc gcctaagact tagatcttaa ggggatatcc tcgaggttcc    2700
ctttagtgag ggttaattgc gagcttggcg taatcatggt catagctgtt tcctgtgtga    2760
aattgttatc cgctcacaat tccacacaac atacgagccg aagcataaa gtgtaaagcc     2820 tggggtgcct aatgagtgag ctaactcaca ttaattgcgt tgcgctcact gcccgctttc    2880
cagtcgggaa acctgtcgtg ccagctgcat taatgaatcg ccaacgcgc ggggagaggc     2940 ggtttgcgta ttgggcgctc ttccgcttcc tcgctcactg actcgctgcg ctcggtcgtt    3000
cggctgcggc gagcggtatc agctcactca aaggcggtaa tacggttatc cacagaatca    3060
ggggataacg caggaaagaa catgtgagca aaaggccagc aaaaggccag gaaccgtaaa    3120
aaggccgcgt tgctggcgtt tttccatagg ctccgccccc ctgacgagca tcacaaaaat    3180
cgacgctcaa gtcagaggtg gcgaaacccg acaggactat aaagatacca ggcgtttccc    3240
cctggaagct ccctcgtgcg ctctcctgtt ccgaccctgc cgcttaccgg atacctgtcc    3300
gcctttctcc cttcgggaag cgtggcgctt tctcatagct cacgctgtag gtatctcagt    3360
tcggtgtagg tcgttcgctc caagctgggc tgtgtgcacg aacccccgt tcagcccgac     3420 cgctgcgcct tatccggtaa ctatcgtctt gagtccaacc cggtaagaca cgacttatcg    3480
ccactggcag cagccactgg taacaggatt agcagagcga ggtatgtagg cggtgctaca    3540
gagttcttga agtggtggcc taactacggc tacactagaa gaacagtatt tggtatctgc    3600
gctctgctga agccagttac cttcggaaaa agagttggta gctcttgatc cggcaaacaa    3660
accaccgctg gtagcggtgg ttttttttgtt tgcaagcagc agattacgcg cagaaaaaaa   3720
ggatctcaag aagatccttt gatcttttct acggggtctg acgctcagtg gaacgaaaac    3780
tcacgttaag ggattttggt catgagatta tcaaaaagga tcttcaccta gatcctttta    3840
aattaaaaat gaagttttaa atcaatctaa agtatatatg agtaaacttg gtctgacagt    3900
taccaatgct taatcagtga ggcacctatc tcagcgatct gtctatttcg ttcatccata    3960
gttgcctgac tccccgtcgt gtagataact acgatacggg agggcttacc atctggcccc    4020
agtgctgcaa tgataccgcg agacccacgc tcaccggctc cagatttatc agcaataaac    4080
cagccagccg gaagggccga gcgcagaagt ggtcctgcaa ctttatccgc ctccatccag    4140
tctattaatt gttgccggga agctagagta agtagttcgc cagttaatag tttgcgcaac    4200
gttgttgcca ttgctacagg catcgtggtg tcacgctcgt cgtttggtat ggcttcattc    4260
agctccggtt cccaacgatc aaggcgagtt acatgatccc ccatgttgtg caaaaaagcg    4320
gttagctcct tcggtcctcc gatcgttgtc agaagtaagt tggccgcagt gttatcactc    4380
atggttatgg cagcactgca taattctctt actgtcatgc catccgtaag atgcttttct    4440
gtgactggtg agtactcaac caagtcattc tgagaatagt gtatgcggcg accgagttgc    4500
tcttgcccgg cgtcaatacg ggataatacc gcgccacata gcagaacttt aaaagtgctc    4560
atcattggaa aacgttcttc ggggcgaaaa ctctcaagga tcttaccgct gttgagatcc    4620
agttcgatgt aacccactcg tgcacccaac tgatcttcag catcttttac tttcaccagc    4680
```

| | | | |
|---|---|---|---|
| gtttctgggt gagcaaaaac aggaaggcaa aatgccgcaa aaaagggaat aagggcgaca | 4740 |
| cggaaatgtt gaatactcat actcttcctt tttcaatatt attgaagcat ttatcagggt | 4800 |
| tattgtctca tgagcggata catatttgaa tgtatttaga aaaataaaca aatagggggtt | 4860 |
| ccgcgcacat ttccccgaaa agtgccacct gacgcgccct gtagcggcgc attaagcgcg | 4920 |
| gcgggtgtgg tggttacgcg cagcgtgacc gctacacttg ccagcgccct agcgcccgct | 4980 |
| cctttcgctt tcttcccttc ctttctcgcc acgttcgccg ctttccccg tcaagctcta | 5040 |
| aatcggggc tccctttagg gttccgattt agtgctttac ggcacctcga ccccaaaaaa | 5100 |
| cttgattagg gtgatggttc acgtagtggg ccatcgccct gatagacggt ttttcgccct | 5160 |
| ttgacgttgg agtccacgtt ctttaatagt ggactcttgt tccaaactgg aacaacactc | 5220 |
| aaccctatct cggtctattc ttttgattta aagggattt tgccgatttc ggcctattgg | 5280 |
| ttaaaaatg agctgatta acaaaaattt aacgcgaatt ttaacaaaat attaacgctt | 5340 |
| acaatttgcc attcgccatt caggctgcgc aactgttggg aagggcgat | 5389 |

<210> SEQ ID NO 52
<211> LENGTH: 9675
<212> TYPE: DNA
<213> ORGANISM: Artificial Sequence
<220> FEATURE:
<223> OTHER INFORMATION: plasmid

<400> SEQUENCE: 52

| | | | |
|---|---|---|---|
| cgcgcctgat gagcctgaac tgcccgggca aatcagctgg cgtaatagcg aagaggcccg | 60 |
| caccgatcgc ccttcccaac agttgcgcag cctgaatggc gaatggcgcg acgcgccctg | 120 |
| tagcggcgca ttaagcgcgg cgggtgtggt ggttacgcgc agcgtgaccg ctacacttgc | 180 |
| cagcgcccta gcgcccgctc ctttcgcttt cttcccttcc tttctcgcca cgttcgccgg | 240 |
| ctttccccgt caagctctaa atcggggggct cccttaggg ttccgattta gtgctttacg | 300 |
| gcacctcgac cccaaaaaac ttgattaggg tgatggttca cgtagtgggc catcgccctg | 360 |
| atagacggtt tttcgccctt tgacgttgga gtccacgttc tttaatagtg gactcttgtt | 420 |
| ccaaactgga caacactca accctatctc ggtctattct tttgatttat aagggatttt | 480 |
| gccgatttcg gcctattggt taaaaaatga gctgatttaa caaaaattta acgcgaattt | 540 |
| taacaaaata ttaacgttta caattcctg atgcggtatt ttctccttac gcatctgtgc | 600 |
| ggtatttcac accgcataga tccgtcgagt tcaagagaaa aaaaagaaa aagcaaaaag | 660 |
| aaaaaaggaa agcgcgcctc gttcagaatg acacgtatag aatgatgcat taccttgtca | 720 |
| tcttcagtat catactgttc gtatacatac ttactgacat tcataggtat acatatatac | 780 |
| acatgtatat atatcgtatg ctgcagcttt aaataatcgg tgtcactaca taagaacacc | 840 |
| tttggtggag ggaacatcgt tggtaccatt gggcgaggtg gcttctctta tggcaaccgc | 900 |
| aagagccttg aacgcactct cactacggtg atgatcattc ttgcctcgca gacaatcaac | 960 |
| gtggagggta attctgctag cctctgcaaa actttcaaga aaatgcggga tcatctcgca | 1020 |
| agagagatct cctactttct ccctttgcaa accaagttcg acaactgcgt acggcctgtt | 1080 |
| cgaaagatct accaccgctc tggaaagtgc ctcatccaaa ggcgcaaatc ctgatccaaa | 1140 |
| cctttttact ccacgcacgg cccctagggc ctctttaaag gcttgaccga gagcaatccc | 1200 |
| gcagtcttca gtggtgtgat ggtcgtctat gtgtaagtca ccaatgcact caacgattag | 1260 |
| cgaccagccg gaatgcttgg ccagagcatg tatcatatgg tccagaaacc ctatacctgt | 1320 |
| gtggacgtta atcacttgcg attgtgtggc ctgttctgct actgcttctg cctctttttc | 1380 |

```
tgggaagatc gagtgctcta tcgctagggg accacccttt aaagagatcg caatctgaat    1440
cttggtttca tttgtaatac gctttactag ggctttctgc tctgtcatct ttgccttcgt    1500
ttatcttgcc tgctcatttt ttagtatatt cttcgaagaa atcacattac tttatataat    1560
gtataattca ttatgtgata atgccaatcg ctaagaaaaa aaaagagtca tccgctaggg    1620
gaaaaaaaaa aatgaaaatc attaccgagg cataaaaaaa tatagagtgt actagaggag    1680
gccaagagta atagaaaaag aaaattgcgg gaaaggactg tgttatgact tccctgacta    1740
atgccgtgtt caaacgatac ctggcagtga ctcctagcgc tcaccaagct cttaaaacgg    1800
gaatttatgg tgcactctca gtacaatctg ctctgatgcc gcatagttaa gccagccccg    1860
acacccgcca acacgcgctg acgcgccctg acgggcttgt ctgctcccgg catccgctta    1920
cagacaagct gtgaccgtct ccgggagctg catgtgtcag aggttttcac cgtcatcacc    1980
gaaacgcgcg agacgaaagg gcctcgtgat acgcctattt ttataggtta atgtcatgat    2040
aataatggtt tcttaggacg gatcgcttgc ctgtaactta cacgcgcctc gtatcttta    2100 atgatggaat aatttgggaa tttactctgt gtttatttat ttttatgttt tgtatttgga    2160
ttttagaaag taaataaaga aggtagaaga gttacggaat gaagaaaaaa aaataaacaa    2220
aggtttaaaa aatttcaaca aaaagcgtac tttacatata tatttattag acaagaaaag    2280
cagattaaat agatatacat tcgattaacg ataagtaaaa tgtaaaatca caggattttc    2340
gtgtgtggtc ttctacacag acaagatgaa acaattcggc attaatacct gagagcagga    2400
agagcaagat aaaaggtagt atttgttggc gatcccccta gagtctttta catcttcgga    2460
aaacaaaaac tatttttct ttaatttctt tttttacttt ctattttaa tttatatatt    2520 tatattaaaa aatttaaatt ataattattt ttatagcacg tgatgaaaag gacccaggtg    2580
gcacttttcg gggaaatgtg cgcggaaccc ctatttgttt attttctaa atacattcaa    2640 atatgtatcc gctcatgaga caataaccct gataaatgct tcaataatat tgaaaaagga    2700
agagtatgag tattcaacat ttccgtgtcg cccttattcc cttttttgcg gcattttgcc    2760
ttcctgtttt tgctcaccca gaaacgctgg tgaaagtaaa agatgctgaa gatcagttgg    2820
gtgcacgagt gggttacatc gaactggatc tcaacagcgg taagatcctt gagagttttc    2880
gccccgaaga acgttttcca atgatgagca cttttaaagt tctgctatgt ggcgcggtat    2940
tatcccgtat tgacgccggg caagagcaac tcggtcgccg catacactat tctcagaatg    3000
acttggttga gtactcacca gtcacagaaa agcatcttac ggatggcatg acagtaagag    3060
aattatgcag tgctgccata accatgagtg ataacactgc ggccaactta cttctgacaa    3120
cgatcggagg accgaaggag ctaaccgctt ttttgcacaa catgggggat catgtaactc    3180
gccttgatcg ttgggaaccg gagctgaatg aagccatacc aaacgacgag cgtgacacca    3240
cgatgcctgt agcaatggca acaacgttgc gcaaactatt aactggcgaa ctacttactc    3300
tagcttcccg gcaacaatta atagactgga tggaggcgga taaagttgca ggaccacttc    3360
tgcgctcggc ccttccggct ggctggttta ttgctgataa atctggagcc ggtgagcgtg    3420
ggtctcgcgg tatcattgca gcactggggc cagatggtaa gccctcccgt atcgtagtta    3480
tctacacgac ggggagtcag gcaactatgg atgaacgaaa tagacagatc gctgagatag    3540
gtgcctcact gattaagcat tggtaactgt cagaccaagt ttactcatat atactttaga    3600
ttgatttaaa acttcatttt taatttaaaa ggatctaggt gaagatcctt tttgataatc    3660
tcatgaccaa aatcccttaa cgtgagtttt cgttccactg agcgtcagac cccgtagaaa    3720
```

```
agatcaaagg atcttcttga gatccttttt ttctgcgcgt aatctgctgc ttgcaaacaa    3780
aaaaaccacc gctaccagcg gtggtttgtt tgccggatca agagctacca actcttttttc   3840
cgaaggtaac tggcttcagc agagcgcaga taccaaatac tgtccttcta gtgtagccgt    3900
agttaggcca ccacttcaag aactctgtag caccgcctac atacctcgct ctgctaatcc    3960
tgttaccagt ggctgctgcc agtggcgata gtcgtgtct taccgggttg gactcaagac     4020
gatagttacc ggataaggcg cagcggtcgg gctgaacggg gggttcgtgc acacagccca    4080
gcttggagcg aacgacctac accgaactga gatacctaca gcgtgagcta tgagaaagcg    4140
ccacgcttcc cgaagggaga aaggcggaca ggtatccggt aagcggcagg gtcggaacag    4200
gagagcgcac gagggagctt ccaggggaaa acgcctggta tctttatagt cctgtcgggt    4260
ttcgccacct ctgacttgag cgtcgatttt tgtgatgctc gtcagggggg cggagcctat    4320
ggaaaaacgc cagcaacgcg gcctttttac ggttcctggc cttttgctgg ccttttgctc    4380
acatgttctt tcctgcgtta tcccctgatt ctgtggataa ccgtattacc gcctttgagt    4440
gagctgatac cgctcgccgc agccgaacga ccgagcgcag cgagtcagtg agcgaggaag    4500
cggaagagcg cccaatacgc aaaccgcctc tccccgcgcg ttggccgatt cattaatgca    4560
gctgatttgc ccgggcagtt caggctcatc aggcgcgccg agcgacctca tgctatacct    4620
gagaaagcaa cctgacctac aggaaagagt tactcaagaa taagaatttt cgttttaaaa    4680
cctaagagtc actttaaaat ttgtatacac ttatttttt tataacttat ttaataataa     4740
aaatcataaa tcataagaaa ttcgcttatt tagaagtgtc aacaacgtat ctaccaacga    4800
tttgacccct ttccatcttt tcgtaaattt ctggcaaggt agacaagccg acaaccttga    4860
ttggagactt gaccaaacct ctggcgaaga attgttaatt aagagctcgt tgcggttat     4920
ttattagatt cttggcaaca ggcaaggatg gactgcttga cactttcgca agcattttttg   4980
agttcctctg gggacatggc ggcgttacag cagattttca agctagggac aattggtagc    5040
gtctcctgtt ttaaaacaat agtgtttctt gtgatgagaa cgttgtagtt aataagagca    5100
tgatctacta tggactgcag aaattttttcc tcctcttcgt atggctcaat gaatttgttt    5160
gtctgggact tcttttgcaa agctgacatg gtttcgaata gctgttcgca ggtgtatccg    5220
aacttgcgag acctatatgc gggagtcagt tgcagatgta ggacagcaga cactggagag    5280
gacgtgacga ttacgtatga acgcaaggag tcgtcagatg caaaggaatc atgcaaagat    5340
ttggatagtt tttgcagcgt ctggacggcg tcgttgttgg agtccatcaa tttcaagact    5400
ttggagacgt atgtgacggt gtaagccggc aaacaggcag aaaaacaata tgcattggaa    5460
ccaatacgct ggtgcaaaca cataacactg tcacccagga caaaaccacc ggtggacccc    5520
aacgcggtgg ccatggaccc aacggtaatg tcaatggcag ttgcgcgatc catgttgaag    5580
tgctctgaca acccacggcc cgtagcgcca agaacaccaa tggagaaggt ttcgtcaaca    5640
aatagtctga acttgtactt gttcttcagc ttagtcaact caggcaacgg agctaaatcg    5700
cccgagttgt ggaaaatacc ctcagtgacg ataaattttc ttggaatggc gggcagtttc    5760
tcaagtttct cctgttcggt caactcgttt aataaacatt ctagcgaatt catatcgttg    5820
tggttgaagt agtagactgt ggatctgctt agttgcagag cattttgcac tggtaatgac    5880
acctggtcgt ctgccacgat aacatcacca cgctttgtga aagcaggcag aacagagggt    5940
gcggcacaaa agtcttgccc gtacagaacg gaaccttggg tgccaaagaa ctgtgctaaa    6000
tcatattcca acgtgtaatg aacgtcctgg ttaccgtaga acccggcggg accacaggcg    6060
cccacaccgt aattcttgat agtggtcttg accacttctt tcacgggctc cgtagcggac    6120
```

```
aattgcaaaa agttgttcga ggccaaattg aaaacattgg tatacttctc ctgcagattg    6180
tttctggtga tagtaatatg gttctgaatg ggcatttcca tggtgacggg tgttttggcc    6240
accctccacg attgctcatc ggtggcagaa gggtcgacta gaggctcggg ctcccagtcc    6300
tcaattagcg cgtcaatctc ctggggcgat aggttgggct tctgtgcttg aagactcttt    6360
ttctgttgtg gcttggacaa gtaatagatg atcccgtata aaataagccc tatctcaacc    6420
gtggtcctgt atggatcgtc atgatgcgat ttccttgatgt acgaaacgat gaattggcct    6480
cccgggattt gagtcaacac cagattgaag tagtaccata ggtacgatga ggtggtaaca    6540
ataaatgccg gaatcggtat tgatttgggt aaaacctctg gatgtgtgc cattttaagc     6600 tagctatttt gtaattaaaa cttagattag attgctatgc tttctttcta atgagcaaga    6660
agtaaaaaaa gttgtaatag aacaagaaaa atgaaactga aacttgagaa attgaagacc    6720
gtttattaac ttaaatatca atgggaggtc atcgaaagag aaaaaaatca aaaaaaaaa     6780 ttttcaagaa aaagaaacgt gataaaaatt tttattgcct ttttcgacga agaaaagaa     6840 acgaggcggt ctctttttc ttttccaaac ctttagtacg ggtaattaac gacaccctag     6900
aggaagaaag aggggaaatt tagtatgctg tgcttgggtg ttttgaagtg gtacggcgat    6960
gcgcggagtc cgagaaaatc tggaagagta aaaaaggagt agaaacattt tgaagctaag    7020
atctacgcac agatattata acatctgcat aataggcatt tgcaagaatt actcgtgagt    7080
aaggaaagag tgaggaacta tcgcatacct gcatttaaag atgccgattt gggcgcgaat    7140
cctttatttt ggcttcaccc tcatactatt atcaggccca gaaaaaggaa gtgtttccct    7200
ccttcttgaa ttgatgttac cctcataaag cacgtggcct cttatcgaga aagaaattac    7260
cgtcgctcgt gatttgtttg caaaaagaac aaaactgaaa aaacccagac acgctcgact    7320
tcctgtcttc ctattgattg cagcttccaa tttcgtcaca caacaaggtc ctagcgacgg    7380
ctcacaggtt ttgtaacaag caatcgaagg ttctggaatg gcgggaaagg gtttagtacc    7440
acatgctatg atgcccactg tgatctccag agcaaagttc gttcgatcgt actgttactc    7500
tctctctttc aaacagaatt gtccgaatcg tgtgacaaca acagcctgtt ctcacacact    7560
cttttcttct aaccaagggg gtggtttagt ttagtagaac ctcgtgaaac ttacatttac    7620
atatatataa acttgcataa attggtcaat gcaagaaata catatttggt cttttctaat    7680
tcgtagtttt tcaagttctt agatgctttc tttttctctt ttttacagat catcaaggaa    7740
gtaattatct acttttaca acaaatataa aacaaagctt aaaatgagta ctcctgcaaa    7800 ctataccgt gtgcccctgt gcgaaccaga ggagctgcca gacgacatac aaaaagaaa     7860 tgaatatggt acactagatt ctccggggca tttgtatcaa gtcaagtcac gtcatgggaa    7920
gccactacct gagcccgttg tcgacacccc tccttattac atttctttgt taacatatct    7980
aaattatttg attctgatta tattaggtca tgttcacgac ttcttaggta tgaccttcca    8040 aaaaacaaa catctggatc ttttagagca tgatggggtta gcaccttggt tttcaaattt    8100
cgagagtttt tatgtcagga gaattaaaat gagaattgat gattgctttt ctagaccaac    8160
tactggtgtt cctggtagat ttattcgttg tattgataga attctcata atataaatga     8220 gtattttacc tactcaggcg cagtgtatcc atgcatgaac ttatcatcat ataactattt    8280
aggcttcgca caaagtaagg gtcaatgtac cgatgccgcc ttggaatctg tcgataaata    8340
ttctattcaa tctggtggtc caagagctca aatcggtacc acagatttgc acattaaagc    8400
agagaaatta gttgctagat ttatcggtaa ggaggatgcc ctcgtttttt cgatgggtta    8460
```

| | | | | |
|---|---|---|---|---|
| tggtacaaat | gcaaacttgt | tcaacgcttt | cctcgataaa | aagtgtttag ttatctctga | 8520 |
| cgaattgaac | cacacctcta | ttagaacagg | tgttaggctt | tctggtgctg ctgtgcgaac | 8580 |
| tttcaagcat | ggtgatatgg | tgggtttaga | aaagctcatc | agagaacaga tagtacttgg | 8640 |
| tcaaccaaaa | acaaatcgtc | catggaagaa | aattttaatt | tgcgcagaag ggttgttttc | 8700 |
| catggaaggt | actttgtgta | acttgccaaa | attggttgaa | ttgaagaaga aatataaatg | 8760 |
| ttacttgttt | atcgatgaag | cccattctat | aggcgctatg | ggcccaactg gtcgcggtgt | 8820 |
| ttgtgaaata | tttggcgttg | atcccaagga | cgtcgacatt | ctaatgggta ctttcactaa | 8880 |
| gtcgtttggt | gctgctggtg | gttacattgc | tgctgatcaa | tggattatcg atagactgag | 8940 |
| gttggattta | accactgtga | gttatagtga | gtcaatgccg | gctcctgttt tagctcaaac | 9000 |
| tatttcctca | ttacaaacca | ttagtggtga | aatatgtccc | ggacaaggta ctgaaagatt | 9060 |
| gcaacgtata | gcctttaatt | cccgttatct | acgtttagct | ttgcaaaggt taggatttat | 9120 |
| tgtctacggt | gtggctgact | caccagttat | tcccttacta | ctgtattgtc cctcaaagat | 9180 |
| gcccgcattt | tcgagaatga | tgttacaaag | acggattgct | gttgttgttg ttgcttatcc | 9240 |
| tgctactccg | ctgatcgaat | caagagtaag | attctgtatg | tctgcatctt taacaaagga | 9300 |
| agatatcgat | tatttactgc | gtcatgttag | tgaagttggt | gacaaattga atttgaaatc | 9360 |
| aaattccggc | aaatccagtt | acgacggtaa | acgtcaaaga | tgggacatcg aggaagttat | 9420 |
| caggagaaca | cctgaagatt | gtaaggacga | caagtatttt | gttaattgac cgcggctagc | 9480 |
| taagatccgc | tctaaccgaa | aggaaggag | ttagacaacc | tgaagtctag gtccctattt | 9540 |
| attttttttat | agttatgtta | gtattaagaa | cgttatttat | atttcaaatt tttctttttt | 9600 |
| ttctgtacag | acgcgtgtac | gcatgtaaca | ttatactgaa | aaccttgctt gagaaggttt | 9660 |
| tgggacgctc | gaagg | | | | 9675 |

<210> SEQ ID NO 53
<211> LENGTH: 8241
<212> TYPE: DNA
<213> ORGANISM: Artificial Sequence
<220> FEATURE:
<223> OTHER INFORMATION: plasmid

<400> SEQUENCE: 53

| | | | | |
|---|---|---|---|---|
| cgcgcctgat | gagcctgaac | tgcccgggca | aatcagctgg | cgtaatagcg aagaggcccg | 60 |
| caccgatcgc | ccttcccaac | agttgcgcag | cctgaatggc | gaatggcgcg acgcgccctg | 120 |
| tagcggcgca | ttaagcgcgg | cgggtgtggt | ggttacgcgc | agcgtgaccg ctacacttgc | 180 |
| cagcgcccta | gcgcccgctc | ctttcgcttt | cttcccttcc | tttctcgcca cgttcgccgg | 240 |
| ctttccccgt | caagctctaa | atcgggggct | ccctttaggg | ttccgattta gtgctttacg | 300 |
| gcacctcgac | cccaaaaaac | ttgattaggg | tgatggttca | cgtagtgggc catcgccctg | 360 |
| atagacggtt | tttcgccctt | tgacgttgga | gtccacgttc | tttaatagtg gactcttgtt | 420 |
| ccaaactgga | acaacactca | accctatctc | ggtctattct | tttgatttat aagggatttt | 480 |
| gccgatttcg | gcctattggt | taaaaaatga | gctgatttaa | caaaaattta acgcgaattt | 540 |
| taacaaaata | ttaacgttta | caatttcctg | atgcggtatt | ttctccttac gcatctgtgc | 600 |
| ggtatttcac | accgcatagg | gtaataactg | atataattaa | attgaagctc taatttgtga | 660 |
| gtttagtata | catgcattta | cttataatac | agttttttag | ttttgctggc cgcatcttct | 720 |
| caaatatgct | tcccagcctg | cttttctgta | acgttcaccc | tctaccttag catcccttcc | 780 |
| ctttgcaaat | agtcctcttc | aacaataat | aatgtcagat | cctgtagaga ccacatcatc | 840 |

```
cacggttcta tactgttgac ccaatgcgtc tcccttgtca tctaaaccca caccgggtgt    900
cataatcaac caatcgtaac cttcatctct tccacccatg tctctttgag caataaagcc    960
gataacaaaa tctttgtcgc tcttcgcaat gtcaacagta cccttagtat attctccagt   1020
agatagggag cccttgcatg acaattctgc taacatcaaa aggcctctag gttcctttgt   1080
tacttcttct gccgcctgct tcaaaccgct aacaatacct gggcccacca caccgtgtgc   1140
attcgtaatg tctgcccatt ctgctattct gtatacaccc gcagagtact gcaatttgac   1200
tgtattacca atgtcagcaa attttctgtc ttcgaagagt aaaaaattgt acttggcgga   1260
taatgccttt agcggcttaa ctgtgccctc catggaaaaa tcagtcaaga tatccacatg   1320
tgttttagt aaacaaattt tgggacctaa tgcttcaact aactccagta attccttggt    1380
ggtacgaaca tccaatgaag cacacaagtt tgtttgcttt tcgtgcatga tattaaatag   1440
cttggcagca acaggactag gatgagtagc agcacgttcc ttatatgtag ctttcgacat   1500
gatttatctt cgtttcctgc aggttttgt tctgtgcagt tgggttaaga atactgggca    1560
atttcatgtt tcttcaacac tacatatgcg tatatatacc aatctaagtc tgtgctcctt   1620
ccttcgttct tccttctgtt cggagattac cgaatcaaaa aaatttcaaa gaaaccgaaa   1680
tcaaaaaaaa gaataaaaaa aaaatgatga attgaattga aaagctgtgg tatggtgcac   1740
tctcagtaca atctgctctg atgccgcata gttaagccag ccccgacacc cgccaacacc   1800
cgctgacgcg ccctgacggg cttgtctgct cccggcatcc gcttacagac aagctgtgac   1860
cgtctccggg agctgcatgt gtcagaggtt tcaccgtca tcaccgaaac gcgcgagacg    1920
aaagggcctc gtgatacgcc tatttttata ggttaatgtc atgataataa tggtttctta   1980
ggacggatcg cttgcctgta acttacacgc gcctcgtatc ttttaatgat ggaataattt   2040
gggaatttac tctgtgttta tttatttta tgttttgtat ttggattta gaaagtaaat     2100
aaagaaggta gaagagttac ggaatgaaga aaaaaaata acaaaggtt taaaaattt      2160
caacaaaaag cgtactttac atatatattt attagacaag aaaagcagat taaatagata   2220
tacattcgat taacgataag taaaatgtaa aatcacagga ttttcgtgtg tggtcttcta   2280
cacagacaag atgaaacaat tcggcattaa tacctgagag caggaagagc aagataaaag   2340
gtagtatttg ttggcgatcc ccctagagtc ttttacatct tcggaaaaca aaaactattt   2400
tttctttaat ttctttttt actttctatt tttaatttat atatttatat taaaaattt     2460
aaattataat tatttttata gcacgtgatg aaaaggaccc aggtggcact tttcggggaa   2520
atgtgcgcgg aaccctatt tgtttatttt tctaaataca ttcaaatatg tatccgctca    2580
tgagacaata accctgataa atgcttcaat aatattgaaa aaggaagagt atgagtattc   2640
aacatttccg tgtcgccctt attcccttt ttgcggcatt ttgccttcct gttttgctc     2700
acccagaaac gctggtgaaa gtaaaagatg ctgaagatca gttgggtgca cgagtgggtt   2760
acatcgaact ggatctcaac agcggtaaga tccttgagag ttttcgcccc gaagaacgtt   2820
ttccaatgat gagcactttt aaagttctgc tatgtggcgc ggtattatcc cgtattgacg   2880
ccgggcaaga gcaactcggt cgccgcatac actattctca gaatgacttg gttgagtact   2940
caccagtcac agaaaagcat cttacggatg gcatgacagt aagagaatta tgcagtgctg   3000
ccataaccat gagtgataac actgcggcca acttacttct gacaacgatc ggaggaccga   3060
aggagctaac cgcttttttg cacaacatgg gggatcatgt aactcgcctt gatcgttggg   3120
aaccggagct gaatgaagcc ataccaaacg acgagcgtga caccacgatg cctgtagcaa   3180
```

```
tggcaacaac gttgcgcaaa ctattaactg gcgaactact tactctagct tcccggcaac    3240
aattaataga ctggatggag gcggataaag ttgcaggacc acttctgcgc tcggcccttc    3300
cggctggctg gtttattgct gataaatctg gagccggtga gcgtgggtct cgcggtatca    3360
ttgcagcact ggggccagat ggtaagccct cccgtatcgt agttatctac acgacgggga    3420
gtcaggcaac tatggatgaa cgaaatagac agatcgctga gataggtgcc tcactgatta    3480
agcattggta actgtcagac caagtttact catatatact ttagattgat ttaaaacttc    3540 attttaatt taaaaggatc taggtgaaga tcctttttga taatctcatg accaaaatcc    3600
cttaacgtga gttttcgttc cactgagcgt cagaccccgt agaaaagatc aaaggatctt    3660
cttgagatcc ttttttctg cgcgtaatct gctgcttgca acaaaaaaa ccaccgctac    3720 cagcggtggt ttgtttgccg gatcaagagc taccaactct ttttccgaag gtaactggct    3780
tcagcagagc gcagatacca aatactgtcc ttctagtgta gccgtagtta ggccaccact    3840
tcaagaactc tgtagcaccg cctacatacc tcgctctgct aatcctgtta ccagtggctg    3900
ctgccagtgg cgataagtcg tgtcttaccg ggttggactc aagacgatag ttaccggata    3960
aggcgcagcg gtcgggctga acggggggtt cgtgcacaca gcccagcttg gagcgaacga    4020
cctacaccga actgagatac ctacagcgtg agctatgaga agcgccacg cttcccgaag    4080 ggagaaaggc ggacaggtat ccggtaagcg gcagggtcgg aacaggagag cgcacgaggg    4140
agcttccagg gggaaacgcc tggtatcttt atagtcctgt cgggtttcgc cacctctgac    4200
ttgagcgtcg attttgtga tgctcgtcag ggggggcggag cctatggaaa aacgccagca    4260
acgcggcctt tttacggttc ctggcctttt gctggccttt tgctcacatg ttctttcctg    4320
cgttatcccc tgattctgtg gataaccgta ttaccgcctt tgagtgagct gataccgctc    4380
gccgcagccg aacgaccgag cgcagcgagt cagtgagcga ggaagcggaa gagcgcccaa    4440
tacgcaaacc gcctctcccc gcgcgttggc cgattcatta atgcagctga tttgcccggg    4500
cagttcaggc tcatcaggcg cgccgagcga cctcatgcta tacctgagaa agcaacctga    4560
cctacaggaa agagttactc aagaataaga attttcgttt taaaacctaa gagtcacttt    4620
aaaatttgta tacacttatt ttttttataa cttatttaat aataaaaatc ataaatcata    4680
agaaattcgc ttatttagaa gtgtcaacaa cgtatctacc aacgatttga ccctttttcca   4740 tcttttcgta aatttctggc aaggtagaca agccgacaac cttgattgga gacttgacca    4800
aacctctggc gaagaattgt taattaagag ctcgtttggt cagttggcct tcttgccgtc    4860
attttcacga aaccatttcc tgatatacca ggaacagcca accatgtaga atggcacgac    4920
cagaatgttt gataggacac caaaaatcca ttgcaacgga acaaagcggc ttttctttgc    4980
ggtgagccca aggtccatcc ccattatcat ccatccgaca aaatctgtaa aaacgtcatc    5040
atcacctctg gccagcgact tggcaatgat atcacatgct gtttgcatg ggatagcgtc     5100 tgagggcct tcgatcaact ttgtaatttc gggtttcgtt agctgctcta cagtgaaacc     5160
ttcgctttca aaattaccag gataaacaca actgatacgg aagttcgtca gttcttgtct    5220
taagattgct accagtgatt tgattgcagc ttttgcaggc gcatactggg aatagcccac    5280
aaatgggtaa agcgcggtgg cactagaaaa gatgatgagg tggtgttcct tggtttgctc    5340
tgcaagggca atctgatgtg ccacgttcaa agttgtttta tagttgatgt ccatacccaa    5400
gttcaactca tgtccgctta gcccacgaaa taacttagga acagcccccc ctgcacagca    5460
taacgtttgt gtagggagta aatccaagtc tctcagggca ttgaacaaac attccacgga    5520
ttcgtagcag gacaagtcgc atgggtagta aaataaccgt tgctcaaggt ccaagggcgc    5580
```

-continued

```
agccaactta tgttgcactt ggccctcgtc agtggtttcc cttctcaggt gagcttcaat    5640
cctaatttcg ttgcatgtgt ccagcagtct agcctctgac ctactgacga taataatctt    5700
tgtgttttca gcctcattat aatatttttt ggcgaattcc tttccaagac cttgtgaacc    5760
accagtgatc aacacaactt ggtcttctaa cgtaaacttc attttaagct attttgtaat    5820
taaaacttag attagattgc tatgctttct ttctaatgag caagaagtaa aaaagttgt     5880 aatagaacaa gaaaaatgaa actgaaactt gagaaattga agaccgttta ttaacttaaa    5940
tatcaatggg aggtcatcga agagaaaaa atcaaaaaa aaaatttttc aagaaaaaga     6000
aacgtgataa aaattttat tgccttttc gacgaagaaa agaaacgag gcggtctctt      6060 ttttctttc caaaccttta gtacgggtaa ttaacgacac cctagaggaa gaaagagggg    6120
aaatttagta tgctgtgctt gggtgttttg aagtggtacg gcgatgcgcg gagtccgaga    6180
aaatctggaa gagtaaaaaa ggagtagaaa cattttgaag ctaagatcta cgcacagata    6240
ttataacatc tgcataatag gcatttgcaa gaattactcg tgagtaagga aagagtgagg    6300
aactatcgca tacctgcatt taaagatgcc gatttgggcg cgaatccttt attttggctt    6360
caccctcata ctattatcag ggccagaaaa aggaagtgtt tccctccttc ttgaattgat    6420
gttaccctca taaagcacgt ggcctcttat cgagaaagaa attaccgtcg ctcgtgattt    6480
gtttgcaaaa agaacaaaac tgaaaaaacc cagacacgct cgacttcctg tcttcctatt    6540
gattgcagct tccaatttcg tcacacaaca aggtcctagc gacggctcac aggttttgta    6600
acaagcaatc gaaggttctg gaatggcggg aaagggttta gtaccacatg ctatgatgcc    6660
cactgtgatc tccagagcaa agttcgttcg atcgtactgt tactctctct ctttcaaaca    6720
gaattgtccg aatcgtgtga caacaacagc ctgttctcac acactctttt cttctaacca    6780 aggggtggt ttagtttagt agaacctcgt gaaacttaca tttacatata tataaacttg     6840
cataaattgg tcaatgcaag aaatacatat ttggtctttt ctaattcgta gtttttcaag    6900
ttcttagatg ctttcttttt ctctttttta cagatcatca aggaagtaat tatctacttt    6960
ttacaacaaa tataaaacaa agcttatgaa cgtaacatcg aatgcaactg cagccggttc    7020 cttccacta gcatttggtc tcaagacctc atttgggttt atgcactatg ccaaggcccc      7080
tgccattaat ttacgcccca aggaatcctt gctgccggaa atgagtgatg gtgtgctggc    7140
cttggttgcg ccggttgttg cctactgggc gttgtctggt atattccatg taatagacac    7200
tttccatctg gctgagaagt acagaattca tccgagcgaa gaggttgcca agaggaacaa    7260
ggcgtcgaga atgcatgttt tccttgaagt gattctacaa catatcatac agaccattgt    7320
tggccttatc tttatgcact tcgagccgat ctacatgact gggtttgaag aaaatgccat    7380
gtggaagcta cgtgcagacc ttcctcggat tattccagat gccgctattt attacggcta    7440
tatgtacgga atgtccgctt tgaagatctt tgcaggcttt ttattcgttg atacatggca    7500
ataccttttg catagattga tgcatatgaa taagacctta tacaaatggt tccactctgt    7560
tcatcatgaa ctatacgtgc catatgctta cggtgctctt ttcaacaatc tgttgagggg    7620
cttcttgtta gatactttgg gaaccggtat tgccatgacg ttaactcatt tgactcacag    7680
agagcaaatc attctttta cctttgccac catgaagact gtcgatgacc actgtgggta    7740
tgctttgcca cttgacccat tccaatggct tttccctaat aacgctgtct atcacgatat    7800
ccaccaccag caatttggta tcaagacgaa ctttgctcaa ccattttca ctttctggga    7860 caatttgttc caaactaact ttaaagggtt tgaagaatat caaaagaagc aaagacgtgt    7920
```

| | |
|---|---:|
| caccatcgac aagtacaaag agtttttgca agagagagaa ttggaaaaga aggagaaact | 7980 |
| caaaaacttc aaagctatga atgctgctga aaatgaagta aagaaagaga ataaccgcg | 8040 |
| gctagctaag atccgctcta accgaaaagg aaggagttag acaacctgaa gtctaggtcc | 8100 |
| ctatttattt ttttatagtt atgttagtat taagaacgtt atttatattt caaattttc | 8160 |
| ttttttttct gtacagacgc gtgtacgcat gtaacattat actgaaaacc ttgcttgaga | 8220 |
| aggttttggg acgctcgaag g | 8241 |

```
<210> SEQ ID NO 54
<211> LENGTH: 7434
<212> TYPE: DNA
<213> ORGANISM: Artificial Sequence
<220> FEATURE:
<223> OTHER INFORMATION: plasmid

<400> SEQUENCE: 54
```

| | |
|---|---:|
| tcgctattac gccagctgat ttgcccgggc agttcaggct catcaggcgc gccatgcagg | 60 |
| atgcattgat cagttaaccc atgggcatgc gaaggaaaat gagaaatatc gagggagacg | 120 |
| attcagagga gcaggacaaa ctataaccga ctgtttgttg gaggatgccg tacataacga | 180 |
| acactgctga agctaccatg tctacagttt agaggaatgg gtacaactca caggcgaggg | 240 |
| atggtgttca ctcgtgctag caaacgcggt gggagcaaaa agtagaatat tatctttat | 300 |
| tcgtgaaact tcgaacactg tcatctaaag atgctatata ctaatatagg catacttgat | 360 |
| aatgaaaact ataaatcgta aagacataag agatccgcgg atccccgggt cgagcctgaa | 420 |
| cggcctcgag gcctgaacgg cctcgacgaa ttcattattt gtagagctca tccatgccat | 480 |
| gtgtaatccc agcagcagtt acaaactcaa gaaggaccat gtggtcacgc ttttcgttgg | 540 |
| gatctttcga aagggcagat tgtgtcgaca ggtaatggtt gtctggtaaa aggacagggc | 600 |
| catcgccaat tggagtattt tgttgataat ggtctgctag ttgaacggat ccatcttcaa | 660 |
| tgttgtggcg aattttgaag ttagctttga ttccattctt ttgtttgtct gccgtgatgt | 720 |
| atacattgtg tgagttatag ttgtactcga gtttgtgtcc gagaatgttt ccatcttctt | 780 |
| taaaatcaat acctttaac tcgatacgat taacaagggt atcaccttca aacttgactt | 840 |
| cagcacgcgt cttgtagttc ccgtcatctt tgaaagatat agtgcgttcc tgtacataac | 900 |
| cttcgggcat ggcactcttg aaaaagtcat gccgtttcat atgatccgga taacgggaaa | 960 |
| agcattgaac accataagag aaagtagtga caagtgttgg ccatggaaca ggtagttttc | 1020 |
| cagtagtgca aataaattta agggtaagct ggccctgcag gccaagcttt gttttatatt | 1080 |
| tgttgtaaaa agtagataat tacttccttg atgatctgta aaaagagaa aagaaagca | 1140 |
| tctaagaact tgaaaaacta cgaattagaa aagaccaaat atgtatttct tgcattgacc | 1200 |
| aatttatgca agtttatata tatgtaaatg taagtttcac gaggttctac taaactaaac | 1260 |
| caccccttg gttagaagaa aagagtgtgt gagaacaggc tgttgttgtc acacgattcg | 1320 |
| gacaattctg tttgaaagag agagagtaac agtacgatcg aacgaacttt gctctggaga | 1380 |
| tcacagtggg catcatagca tgtggtacta aaccctttcc cgccattcca gaaccttcga | 1440 |
| ttgcttgtta caaacctgt gagccgtcgc taggaccttg ttgtgtgacg aaattggaag | 1500 |
| ctgcaatcaa taggaagaca ggaagtcgag cgtgtctggg ttttttcagt tttgttcttt | 1560 |
| ttgcaaacaa atcacgagcg acggtaattt cttctctcgat aagaggccac gtgctttatg | 1620 |
| agggtaacat caattcaaga aggagggaaa cacttccttt ttctggccct gataaatagta | 1680 |
| tgagggtgaa gccaaaataa aggattcgcg cccaaatcgg catctttaaa tgcaggtatg | 1740 |

```
cgatagttcc tcactctttc cttactcacg agtaattctt gcaaatgcct attatgcaga    1800
tgttataata tctgtgcgta gatctgatat ccctgcatgg cgcgcctgat gagcctgaac    1860
tgcccgggca aatcagctgc attaatgaat cggccaacgc gcggggagag gcggtttgcg    1920
tattgggcgc tcttccgctt cctcgctcac tgactcgctg cgctcggtcg ttcggctgcg    1980
gcgagcggta tcagctcact caaaggcggt aatacggtta ccacagaat caggggataa     2040 cgcaggaaag aacatgtgag caaaaggcca gcaaaaggcc aggaaccgta aaaaggccgc    2100
gttgctggcg ttttccata ggctccgccc ccctgacgag catcacaaaa atcgacgctc     2160
aagtcagagg tggcgaaacc cgacaggact ataaagatac caggcgtttc ccctggaag     2220 ctccctcgtg cgctctcctg ttccgaccct gccgcttacc ggatacctgt ccgcctttct    2280
cccttcggga agcgtggcgc tttctcatag ctcacgctgt aggtatctca gttcggtgta    2340
ggtcgttcgc tccaagctgg gctgtgtgca cgaaccccc gttcagcccg accgctgcgc     2400
cttatccggt aactatcgtc ttgagtccaa cccggtaaga cacgacttat cgccactggc    2460
agcagccact ggtaacagga ttagcagagc gaggtatgta ggcggtgcta cagagttctt    2520
gaagtggtgg cctaactacg gctacactag aaggacagta tttggtatct gcgctctgct    2580
gaagccagtt accttcggaa aaagagttgg tagctcttga tccggcaaac aaaccaccgc    2640
tggtagcggt ggtttttttg tttgcaagca gcagattacg cgcagaaaaa aaggatctca    2700
agaagatcct ttgatctttt ctacggggtc tgacgctcag tggaacgaaa actcacgtta    2760
agggattttg gtcatgagat tatcaaaaag gatcttcacc tagatccttt taaattaaaa    2820
atgaagtttt aaatcaatct aaagtatata tgagtaaact tggtctgaca gttaccaatg    2880
cttaatcagt gaggcaccta tctcagcgat ctgtctattt cgttcatcca tagttgcctg    2940
actccccgtc gtgtagataa ctacgatacg ggagggctta ccatctggcc ccagtgctgc    3000
aatgataccg cgagacccac gctcaccggc tccagattta tcagcaataa accagccagc    3060
cggaagggcc gagcgcagaa gtggtcctgc aactttatcc gcctccatcc agtctattaa    3120
ttgttgccgg gaagctagag taagtagttc gccagttaat agtttgcgca acgttgttgc    3180
cattgctaca ggcatcgtgg tgtcacgctc gtcgtttggt atggcttcat tcagctccgg    3240
ttcccaacga tcaaggcgag ttacatgatc ccccatgttg tgcaaaaaag cggttagctc    3300
cttcggtcct ccgatcgttg tcagaagtaa gttggccgca gtgttatcac tcatggttat    3360
ggcagcactg cataattctc ttactgtcat gccatccgta agatgctttt ctgtgactgg    3420
tgagtactca accaagtcat tctgagaata gtgtatgcgg cgaccgagtt gctcttgccc    3480
ggcgtcaata cgggataata ccgcgccaca tagcagaact ttaaaagtgc tcatcattgg    3540
aaaacgttct cggggcgaa aactctcaag gatcttaccg ctgttgagat ccagttcgat     3600
gtaacccact cgtgcaccca actgatcttc agcatctttt actttcacca gcgtttctgg    3660
gtgagcaaaa acaggaaggc aaaatgccgc aaaaaaggga taagggcga cacggaaatg     3720 ttgaatactc atactcttcc ttttcaata ttattgaagc atttatcagg gttattgtct      3780
catgagcgga tacatatttg aatgtattta gaaaaataaa caataggggg ttccgcgcac    3840
atttccccga aaagtgccac ctgggtcctt ttcatcacgt gctataaaaa taattataat    3900
ttaaattttt taatataaat atataaatta aaatagaaa gtaaaaaaag aaattaaaga    3960
aaaaatagtt tttgttttcc gaagatgtaa aagactctag ggggatcgcc aacaaatact    4020
accttttatc ttgctcttcc tgctctcagg tattaatgcc gaattgtttc atcttgtctg    4080
```

-continued

```
tgtagaagac cacacacgaa atcctgtga ttttacattt tacttatcgt taatcgaatg   4140
tatatctatt taatctgctt ttcttgtcta ataaatatat atgtaaagta cgcttttgt    4200 tgaaattttt taaacctttg tttatttttt tttcttcatt ccgtaactct tctaccttct   4260
ttatttactt tctaaaatcc aaatacaaaa cataaaaata aataaacaca gagtaaattc   4320
ccaaattatt ccatcattaa aagatacgag gcgcgtgtaa gttacaggca agcgatccgt   4380
cctaagaaac cattattatc atgacattaa cctataaaaa taggcgtatc acgaggccct   4440
ttcgtctcgc gcgtttcggt gatgacggtg aaaacctctg acacatgcag ctcccggaga   4500
cggtcacagc ttgtctgtaa gcggatgccg ggagcagaca agcccgtcag ggcgcgtcag   4560
cgggtgttgg cgggtgtcgg ggctggctta actatgcggc atcagagcag attgtactga   4620
gagtgcacca tatcgactac gtcgtaaggc cgtttctgac agagtaaaat tcttgaggga   4680
actttcacca ttatgggaaa tggttcaaga aggtattgac ttaaactcca tcaaatggtc   4740
aggtcattga gtgttttta tttgttgtat tttttttttt ttagagaaaa tcctccaata   4800
tcaaattagg aatcgtagtt tcatgatttt ctgttacacc taacttttg tgtggtgccc    4860 tcctccttgt caatattaat gttaaagtgc aattcttttt ccttatcacg ttgagccatt   4920
agtatcaatt tgcttacctg tattccttta ctatcctcct ttttctcctt cttgataaat   4980
gtatgtagat tgcgtatata gtttcgtcta ccctatgaac atattccatt ttgtaatttc   5040
gtgtcgtttc tattatgaat ttcatttata aagtttatgt acaaatatca taaaaaaaga   5100
gaatcttttt aagcaaggat tttcttaact tcttcggcga cagcatcacc gacttcggtg   5160
gtactgttgg aaccacctaa atcaccagtt ctgatacctg catccaaaac ctttttaact   5220
gcatcttcaa tggccttacc ttcttcaggc aagttcaatg acaatttcaa catcattgca   5280
gcagacaaga tagtggcgat agggtcaacc ttattctttg gcaaatctgg agcagaaccg   5340
tggcatggtt cgtacaaacc aaatgcggtg ttcttgtctg gcaaagaggc caaggacgca   5400
gatggcaaca aacccaagga acctgggata acggaggctt catcggagat gatatcacca   5460
aacatgttgc tggtgattat aataccattt aggtgggttg ggttcttaac taggatcatg   5520
gcggcagaat caatcaattg atgttgaacc ttcaatgtag ggaattcgtt cttgatggtt   5580
tcctccacag ttttttctcca taatcttgaa gaggccaaaa gattagcttt atccaaggac   5640
caaataggca atggtggctc atgttgtagg gccatgaaag cggccattct tgtgattctt   5700
tgcacttctg gaacggtgta ttgttcacta tcccaagcga caccatcacc atcgtcttcc   5760
tttctcttac caaagtaaat acctcccact aattctctga caacaacgaa gtcagtacct   5820
ttagcaaatt gtggcttgat tggagataag tctaaaagag agtcggatgc aaagttacat   5880
ggtcttaagt tggcgtacaa ttgaagttct ttacggattt ttagtaaacc ttgttcaggt   5940
ctaacactac cggtaccca tttaggacca gccacagcac ctaacaaaac ggcatcaacc     6000
ttcttggagg cttccagcgc ctcatctgga agtgggacac ctgtagcatc gatagcagca   6060
ccaccaatta aatgattttc gaaatcgaac ttgacattgg aacgaacatc agaaatagct   6120
ttaagaacct taatggcttc ggctgtgatt tcttgaccaa cgtggtcacc tggcaaaacg   6180
acgatcttct taggggcaga catagggca gacattagaa tggtatatcc ttgaaatata    6240
tatatatatt gctgaaatgt aaaaggtaag aaaagttaga aagtaagacg attgctaacc   6300
acctattgga aaaacaata ggtccttaaa taatattgtc aacttcaagt attgtgatgc    6360
aagcatttag tcatgaacgc ttctctattc tatatgaaaa gccggttccg gcctctcacc   6420
tttccttttt ctcccaattt ttcagttgaa aaaggtatat gcgtcaggcg acctctgaaa   6480
```

```
ttaacaaaaa atttccagtc atcgaatttg attctgtgcg atagcgcccc tgtgtgttct   6540
cgttatgttg aggaaaaaaa taatggttgc taagagattc gaactcttgc atcttacgat   6600
acctgagtat tcccacagtt aactgcggtc aagatatttc ttgaatcagg cgccttagac   6660
cgctcggcca acaaccaat tacttgttga gaaatagagt ataattatcc tataaatata    6720
acgtttttga acacacatga acaaggaagt acaggacaat tgattttgaa gagaatgtgg   6780
attttgatgt aattgttggg attccatttt taataaggca ataatattag gtatgtggat   6840
atactagaag ttctcctcga ccgtcgatat gcggtgtgaa ataccgcaca gatgcgtaag   6900
gagaaaatac cgcatcagga aattgtaaac gttaatattt tgttaaaatt cgcgttaaat   6960
ttttgttaaa tcagctcatt ttttaaccaa taggccgaaa tcggcaaaat cccttataaa   7020
tcaaaagaat agaccgagat agggttgagt gttgttccag tttggaacaa gagtccacta   7080
ttaaagaacg tggactccaa cgtcaaaggg cgaaaaaccg tctatcaggg cgatggccca   7140
ctacgtgaac catcacccta atcaagtttt tggggtcga ggtgccgtaa agcactaaat     7200
cggaacccta aagggagccc ccgatttaga gcttgacggg gaaagccggc gaacgtggcg   7260
agaaaggaag ggaagaaagc gaaggagcg ggcgctaggg cgctggcaag tgtagcggtc    7320
acgctgcgcg taaccaccac acccgccgcg cttaatgcgc cgctacaggg cgcgtcgcgc   7380
cattcgccat tcaggctgcg caactgttgg gaagggcgat cggtgcgggc ctct          7434
```

<210> SEQ ID NO 55
<211> LENGTH: 6979
<212> TYPE: DNA
<213> ORGANISM: Artificial Sequence
<220> FEATURE:
<223> OTHER INFORMATION: plasmid
<220> FEATURE:
<221> NAME/KEY: misc_feature
<222> LOCATION: (2382)..(2382)
<223> OTHER INFORMATION: n is a, c, g, or t

<400> SEQUENCE: 55

```
agaaaccatt attatcatga cattaaccta taaaaatagg cgtatcacga ggccctttcg     60
tctcgcgcgt ttcggtgatg acggtgaaaa cctctgacac atgcagctcc cggagacggt   120
cacagcttgt ctgtaagcgg atgccgggag cagacaagcc cgtcagggcg cgtcagcggg   180
tgttggcggg tgtcggggct ggcttaacta tgcggcatca gagcagattg tactgagagt   240
gcaccatacc acagctttc aattcaattc atcatttttt ttttattctt ttttttgatt     300
tcggtttctt tgaaattttt ttgattcggt aatctccgaa cagaaggaag aacgaaggaa   360
ggagcacaga cttagattgg tatatatacg catatgtagt gttgaagaaa catgaaattg   420
cccagtattc ttaacccaac tgcacagaac aaaaacctgc aggaaacgaa gataaatcat   480
gtcgaaagct acatataagg aacgtgctgc tactcatcct agtcctgttg ctgccaagct   540
atttaatatc atgcacgaaa agcaaacaaa cttgtgtgct tcattggatg ttcgtaccac   600
caaggaatta ctggagttag ttgaagcatt aggtcccaaa atttgtttac taaaaacaca   660
tgtggatatc ttgactgatt tttccatgga gggcacagtt aagccgctaa aggcattatc   720
cgccaagtac aattttttac tcttcgaaga cagaaaattt gctgacattg gtaatacagt   780
caaattgcag tactctgcgg gtgtatacag aatagcagaa tgggcagaca ttacgaatgc   840
acacggtgtg gtgggcccag gtattgttag cggtttgaag caggcggcag aagaagtaac   900
aaaggaacct agaggccttt tgatgttagc agaattgtca tgcaagggct ccctatctac   960
```

```
tggagaatat actaagggta ctgttgacat tgcgaagagc gacaaagatt ttgttatcgg   1020
ctttattgct caaagagaca tgggtggaag agatgaaggt tacgattggt tgattatgac   1080
acccggtgtg ggtttagatg acaagggaga cgcattgggt caacagtata gaaccgtgga   1140
tgatgtggtc tctacaggat ctgacattat tattgttgga agaggactat ttgcaaaggg   1200
aagggatgct aaggtagagg gtgaacgtta cagaaaagca ggctgggaag catatttgag   1260
aagatgcggc cagcaaaact aaaaaactgt attataagta aatgcatgta tactaaactc   1320
acaaattaga gcttcaattt aattatatca gttattaccc tatgcggtgt gaaataccgc   1380
acagatgcgt aaggagaaaa taccgcatca ggaaattgta aacgttaata ttttgttaaa   1440
attcgcgtta aattttgtt aaatcagctc attttttaac caataggccg aaatcggcaa   1500
aatcccttat aaatcaaaag aatagaccga gatagggttg agtgttgttc cagtttggaa   1560
caagagtcca ctattaaaga acgtggactc caacgtcaaa gggcgaaaaa ccgtctatca   1620
gggcgatggc ccactacgtg aaccatcacc ctaatcaagt tttttggggt cgaggtgccg   1680
taaagcacta aatcggaacc ctaaagggag cccccgattt agagcttgac ggggaaagcc   1740
ggcgaacgtg gcgagaaagg aagggaagaa agcgaaagga gcgggcgcta gggcgctggc   1800
aagtgtagcg gtcacgctgc gcgtaaccac cacacccgcc gcgcttaatg cgccgctaca   1860
gggcgcgtcg cgccattcgc cattcaggct gcgcaactgt tgggaagggc gatcggtgcg   1920
ggcctcttcg ctattacgcc agctggcgaa agggggatgt gctgcaaggc gattaagttg   1980
ggtaacgcca gggttttccc agtcacgacg ttgtaaaacg acggccagtg agcgcgcgta   2040
atacgactca ctatagggcg aattgggtac cggccgcaaa ttaaagcctt cgagcgtccc   2100
aaaaccttct caagcaaggt tttcagtata atgttacatg cgtacacgcg tctgtacaga   2160 aaaaaagaa aaatttgaaa tataaataac gttcttaata ctaacataac tataaaaaaa   2220 taaatagga cctagacttc aggttgtcta actccttcct tttcggttag agcggatgtg   2280
gggggagggc gtgaatgtaa gcgtgacata actaattaca tgactcgagg tcgacaattc   2340
caaccttacc caagagttcg ccaaactcag acatcacttt angcaaaacc gcgccgtgct   2400
tcttcctcgg tggcattcat cacgaaatgt tcagcactac gcatacttt gacaggaaac    2460 gcaacggata ttgagtcaat atcaggcatt ctatcgctca gctttacagt gacaatgacg   2520
gctggcgact gaatattagt gcttacagac agcactacat atttccgtc gatgttgaaa    2580 tccttctca tatgtcacca taaatatcaa ataattatag caatcattta cgcgttaatg    2640
gctaatcgcc atcttccagc aggcgcacca ttgcccctgt ttcactatcc agggtacgga   2700
tatagttcat gacaatattt acattggtcc agccaccagc ttgcatgatc tccggtattg   2760
aaactccagc gcgggccata tctcgcgcgg ctccgacacg ggcactgtgt ccagaccagg   2820
ccaggtatct ctgaccagag tcatccttag cgccgtaaat caatcgatga gttgcttcaa   2880
aaatcccttc cagggcgcga gttgatagct ggctggtggc agatggcgcg gcaacaccat   2940
tttttctgac ccggcaaaac aggtagttat tcggatcatc agctacacca gagacggaaa   3000
tccatcgctc gaccagttta gttaccccca ggctaagtgc cttctctaca cctgcggtgc   3060
taaccagcgt tttcgttctg ccaatatgga ttaacattct cccaccgtca gtacgtgaga   3120
tatctttaac cctgatcctg gcaatttcgg ctatacgtaa cagggtgtta taagcaatcc   3180
ccagaaatgc cagattacgt atatcctggc agcgatcgct attttccatg agtgaacgaa   3240
cctggtcgaa atcagtgcgt tcgaacgcta gagcctgttt tgcacgttca ccggcatcaa   3300
cgttttcttt tcggatccgc cgcataacca gtgaaacagc attgctgtca cttggtcgtg   3360
```

```
gcagcccgga ccgacgatga agcatgttta gctggcccaa atgttgctgg atagttttta    3420
ctgccagacc gcgcgcctga agatatagaa gataatcgcg aacatcttca ggttctgcgg    3480
gaaaccattt ccggttattc aacttgcacc atgccgccca cgaccggcaa acggacagaa    3540
gcattttcca ggtatgctca gaaaacgcct ggcgatccct gaacatgtcc atcaggttct    3600
tgcgaacctc atcactcgtt gcatcgaccg gtaatgcagg caaattttgg tgtacggtca    3660
gtaaattgga catttaacac tcagataatg ttttaagta agtgtacag gatcggctct      3720
gcccctcgac ggtatcgata agcttgatat cgaattcctg cagcccgggg gatccactag    3780
ttctagaatc cggggttttt tctccttgac gttaaagtat agaggtatat aacaatttt    3840
ttgttgatac ttttattaca tttgaataag aagtaataca aaccgaaaat gttgaaagta    3900
ttagttaaag tggttatgca gttttttgcat ttatatatct gttaatagat caaaaatcat   3960
cgcttcgctg attaattacc ccagaaataa ggctaaaaaa ctaatcgcat tatcatccta    4020
tggttgttaa tttgattcgt tcatttgaag gtttgtgggg ccaggttact gccaattttt    4080
cctcttcata accataaaag ctagtattgt agaatcttta ttgttcggag cagtgcggcg    4140
cgaggcacat ctgcgtttca ggaacgcgac cggtgaagac gaggacgcac ggaggagagt    4200
cttccttcgg agggctgtca cccgctcggc ggcttctaat ccgtactaga gctccagctt    4260
ttgttccctt tagtgagggt taattgcgcg cttggcgtaa tcatggtcat agctgttttcc   4320
tgtgtgaaat tgttatccgc tcacaattcc acacaacata ggagccggaa gcataaagtg    4380
taaagcctgg ggtgcctaat gagtgaggta actcacatta attgcgttgc gctcactgcc    4440
cgcttttcag tcgggaaacc tgtcgtgcca gctgcattaa tgaatcggcc aacgcgcggg    4500
gagaggcggt ttgcgtattg ggcgctcttc cgcttcctcg ctcactgact cgctgcgctc    4560
ggtcgttcgg ctgcggcgag cggtatcagc tcactcaaag gcggtaatac ggttatccac    4620
agaatcaggg gataacgcag gaaagaacat gtgagcaaaa ggccagcaaa aggccaggaa    4680
ccgtaaaaag gccgcgttgc tggcgttttt ccataggctc cgcccccctg acgagcatca    4740
caaaaatcga cgctcaagtc agaggtggcg aaacccgaca ggactataaa gataccaggc    4800
gtttccccct ggaagctccc tcgtgcgctc tcctgttccg accctgccgc ttaccggata    4860
cctgtccgcc tttctccctt cgggaagcgt ggcgctttct catagctcac gctgtaggta    4920
tctcagttcg gtgtaggtcg ttcgctccaa gctgggctgt gtgcacgaac cccccgttca    4980
gcccgaccgc tgcgccttat ccggtaacta tcgtcttgag tccaacccgg taagacacga    5040
cttatcgcca ctggcagcag ccactggtaa caggattagc agagcgaggt atgtaggcgg    5100
tgctacagag ttcttgaagt ggtggcctaa ctacggctac actagaagga cagtatttgg    5160
tatctgcgct ctgctgaagc cagttacctt cggaaaaaga gttggtagct cttgatccgg    5220
caaacaaacc accgctggta gcggtggttt ttttgtttgc aagcagcaga ttacgcgcag    5280
aaaaaaagga tctcaagaag atcctttgat cttttctacg gggtctgacg ctcagtggaa    5340
cgaaaactca cgttaaggga ttttggtcat gagattatca aaaaggatct tcacctagat    5400
ccttttaaat taaaaatgaa gttttaaatc aatctaaagt atatatgagt aaacttggtc    5460
tgacagttac caatgcttaa tcagtgaggc acctatctca gcgatctgtc tatttcgttc    5520
atccatagtt gcctgactcc ccgtcgtgta gataactacg atacgggagg gcttaccatc    5580
tggccccagt gctgcaatga taccgcgaga cccacgctca ccggctccag atttatcagc    5640
aataaaccag ccagccggaa gggccgagcg cagaagtggt cctgcaactt tatccgcctc    5700
```

-continued

```
catccagtct attaattgtt gccgggaagc tagagtaagt agttcgccag ttaatagttt    5760
gcgcaacgtt gttgccattg ctacaggcat cgtggtgtca cgctcgtcgt ttggtatggc    5820
ttcattcagc tccggttccc aacgatcaag gcgagttaca tgatccccca tgttgtgcaa    5880
aaaagcggtt agctccttcg gtcctccgat cgttgtcaga agtaagttgg ccgcagtgtt    5940
atcactcatg gttatggcag cactgcataa ttctcttact gtcatgccat ccgtaagatg    6000
cttttctgtg actggtgagt actcaaccaa gtcattctga aatagtgta tgcggcgacc    6060 gagttgctct tgcccggcgt caatacggga taataccgcg ccacatagca gaactttaaa    6120
agtgctcatc attggaaaac gttcttcggg gcgaaaactc tcaaggatct taccgctgtt    6180
gagatccagt tcgatgtaac ccactcgtgc acccaactga tcttcagcat cttttacttt    6240
caccagcgtt tctgggtgag caaaaacagg aaggcaaaat gccgcaaaaa agggaataag    6300
ggcgacacgg aaatgttgaa tactcatact cttccttttt caatattatt gaagcattta    6360
tcagggttat tgtctcatga gcggatacat atttgaatgt atttagaaaa ataaacaaat    6420
aggggttccg cgcacatttc cccgaaaagt gccacctggg tccttttcat cacgtgctat    6480
aaaaataatt ataatttaaa ttttttaata taaatatata aattaaaaat agaaagtaaa    6540
aaaagaaatt aaagaaaaaa tagttttgt tttccgaaga tgtaaaagac tctaggggga    6600
tcgccaacaa atactacctt ttatcttgct cttcctgctc tcaggtatta atgccgaatt    6660
gtttcatctt gtctgtgtag aagaccacac acgaaaatcc tgtgatttta cattttactt    6720
atcgttaatc gaatgtatat ctatttaatc tgcttttctt gtctaataaa tatatatgta    6780
aagtacgctt tttgttgaaa ttttttaaac ctttgtttat ttttttttct tcattccgta    6840
actcttctac cttctttatt tactttctaa aatccaaata caaaacataa aaataaataa    6900
acacagagta aattcccaaa ttattccatc attaaaagat acgaggcgcg tgtaagttac    6960
aggcaagcga tccgtcctta                                                6979
```

<210> SEQ ID NO 56
<211> LENGTH: 1704
<212> TYPE: DNA
<213> ORGANISM: Artificial Sequence
<220> FEATURE:
<223> OTHER INFORMATION: Gene deletion construct

<400> SEQUENCE: 56

```
tcaagggcaa attgatgctt caacgaaaaa gttattggat tttcagcata ggccactagt      60
ggatctgata tcacctaata acttcgtata gcatacatta tacgaagtta tattaagggt     120
tctcgagagc tcgttttcga cactggatgg cggcgttagt atcgaatcga cagcagtata     180
gcgaccagca ttcacatacg attgacgcat gatattactt tctgcgcact taacttcgca     240
tctgggcaga tgatgtcgag gcgaaaaaaa atataaatca cgctaacatt tgattaaaat     300
agaacaacta caatataaaa aaactataca aatgacaagt tcttgaaaac aagaatcttt     360
ttattgtcag tactgattag aaaaactcat cgagcatcaa atgaaactgc aatttattca     420
tatcaggatt atcaatacca tattttgaa aaagccgttt ctgtaatgaa ggagaaaact     480
caccgaggca gttccatagg atggcaagat cctggtatcg gtctgcgatt ccgactcgtc     540
caacatcaat acaacctatt aatttcccct cgtcaaaaat aaggttatca agtgagaaat     600
caccatgagt gacgactgaa tccggtgaga atggcaaaag cttatgcatt tctttccaga     660
cttgttcaac aggccagcca ttacgctcgt catcaaaatc actcgcatca accaaaccgt     720
tattcattcg tgattgcgcc tgagcgagac gaaatacgcg atcgctgtta aaaggacaat     780
```

```
tacaaacagg aatcgaatgc aaccggcgca ggaacactgc cagcgcatca acaatatttt    840
cacctgaatc aggatattct tctaatacct ggaatgctgt tttgccgggg atcgcagtgg    900
tgagtaacca tgcatcatca ggagtacgga taaaatgctt gatggtcgga agaggcataa    960
attccgtcag ccagtttagt ctgaccatct catctgtaac atcattggca acgctacctt   1020
tgccatgttt cagaaacaac tctggcgcat cgggcttccc atacaatcga tagattgtcg   1080
cacctgattg cccgacatta tcgcgagccc atttataccc atataaatca gcatccatgt   1140
tggaatttaa tcgcggcctc gaaacgtgag tcttttcctt acccatggtt gtttatgttc   1200
ggatgtgatg tgagaactgt atcctagcaa gattttaaaa ggaagtatat gaaagaagaa   1260
cctcagtggc aaatcctaac cttttatatt tctctacagg ggcgcggcgt ggggacaatt   1320
caacgcgtct gtgaggggag cgtttccctg ctcgcaggtc tgcagcgagg agccgtaatt   1380
tttgcttcgc gccgtgcggc catcaaaatg tatggatgca aatgattata catggggatg   1440
tatgggctaa atgtacgggc gacagtcaca tcatgcccct gagctgcgca cgtcaagact   1500
gtcaaggagg gtattctggg cctccatgtc gctggccggg tgacccggcg gggacgaggc   1560
aagctaaaca gatctctaga cctaataact tcgtatagca tacattatac gaagttatat   1620
taagggttgt cgacctgcag cgtacgaagc ttcagctggc atctcgctgg ttaattttcc   1680
tgtctcttgt ctatccagca ctta                                         1704
```

<210> SEQ ID NO 57
<211> LENGTH: 1467
<212> TYPE: DNA
<213> ORGANISM: Artificial Sequence
<220> FEATURE:
<223> OTHER INFORMATION: Gene deletion construct

<400> SEQUENCE: 57

```
aagtctagca gcgaaaagta cgcgaagaat ctactataga taatgccagc tgaagcttcg     60
tacgctgcag gtcgacaacc cttaatataa cttcgtataa tgtatgctat acgaagttat    120
taggtctaga gatctgttta gcttgccttg tccccgccgg gtcacccggc cagcgacatg    180
gaggcccaga ataccctcct tgacagtctt gacgtgcgca gctcagggc atgatgtgac    240 tgtcgcccgt acatttagcc catacatccc catgtataat catttgcatc catacatttt    300
gatggccgca cggcgcgaag caaaaattac ggctcctcgc tgcagacctg cgagcaggga    360
aacgctcccc tcacagacgc gttgaattgt ccccacgccg cgcccctgta gagaaatata    420
aaaggttagg atttgccact gaggttcttc tttcatatac ttcctttaa aatcttgcta    480 ggatacagtt ctcacatcac atccgaacat aaacaaccat gggtaccact cttgacgaca    540
cggcttaccg gtaccgcacc agtgtcccgg ggacgccga ggccatcgag cactggatg    600 ggtccttcac caccgacacc gtcttccgcg tcaccgccac cggggacggc ttcaccctgc    660
gggaggtgcc ggtggacccg ccctgacca aggtgttccc cgacgacgaa tcggacgacg    720
aatcggacga cggggaggac ggcgacccgg actcccggac gttcgtcgcg tacggggacg    780
acggcgacct ggcgggcttc gtggtcgtct cgtactccgg ctggaaccgc cggctgaccg    840
tcgaggacat cgaggtcgcc ccggagcacc ggggcacgg gtcgggcgc gcgttgatgg    900 ggctcgcgac ggagttcgcc cgcgagcggg cgccgggca cctctggctg gaggtcacca    960
acgtcaacgc accggcgatc cacgcgtacc ggcggatggg gttcacccctc tgcggcctgg   1020 acaccgccct gtacgacggc accgcctcgg acggcgagca ggcgctctac atgagcatgc   1080
```

```
cctgccccta atcagtactg acaataaaaa gattcttgtt ttcaagaact tgtcatttgt   1140 atagttttt  tatattgtag ttgttctatt ttaatcaaat gttagcgtga tttatatttt   1200
ttttcgcctc gacatcatct gcccagatgc gaagttaagt gcgcagaaag taatatcatg   1260
cgtcaatcgt atgtgaatgc tggtcgctat actgctgtcg attcgatact aacgccgcca   1320
tccagtgtcg aaaacgagct ctcgagaacc cttaatataa cttcgtataa tgtatgctat   1380
acgaagttat taggtgatat cagatccact agtggcctat gctagattaa cgttatattt   1440
tccttcaaaa atgatttttt tgtaaaa                                      1467

<210> SEQ ID NO 58
<211> LENGTH: 1467
<212> TYPE: DNA
<213> ORGANISM: Artificial Sequence
<220> FEATURE:
<223> OTHER INFORMATION: Gene deletion construct

<400> SEQUENCE: 58
aaaccacaaa tagtgtaaga tttaaacagt aagccaaaag agatgccagc tgaagcttcg     60
tacgctgcag gtcgacaacc cttaatataa cttcgtataa tgtatgctat acgaagttat    120
taggtctaga gatctgttta gcttgccttg tccccgccgg gtcacccggc cagcgacatg    180
gaggcccaga ataccctcct tgacagtctt gacgtgcgca gctcaggggc atgatgtgac    240
tgtcgcccgt acatttagcc catacatccc catgtataat catttgcatc catacatttt    300
gatggccgca cggcgcgaag caaaaattac ggctcctcgc tgcagacctg cgagcaggga    360
aacgctcccc tcacagacgc gttgaattgt ccccacgccg cgcccctgta gagaaatata    420
aaaggttagg atttgccact gaggttcttc tttcatatac ttccttttaa aatcttgcta    480
ggatacagtt ctcacatcac atccgaacat aaacaaccat gggtaccact cttgacgaca    540
cggcttaccg gtaccgcacc agtgtcccgg gggacgccga ggccatcgag cactggatg     600 ggtccttcac caccgacacc gtcttccgcg tcaccgccac cggggacggc ttcaccctgc    660
gggaggtgcc ggtggacccg cccctgacca aggtgttccc cgacgacgaa tcggacgacg    720
aatcggacga cggggaggac ggcgacccgg actcccggac gttcgtcgcg tacgggacg     780 acggcgacct ggcgggcttc gtggtcgtct cgtactccgg ctggaaccgc cggctgaccg    840
tcgaggacat cgaggtcgcc ccggagcacc ggggcacgg  ggtcgggcgc gcgttgatgg    900
ggctcgcgac ggagttcgcc cgcgagcggg gcgccgggca cctctggctg gaggtcacca    960
acgtcaacgc accggcgatc cacgcgtacc ggcggatggg gttcaccctc tgcggcctgg   1020
acaccgccct gtacgacggc accgcctcgg acggcgagca ggcgctctac atgagcatgc   1080
cctgccccta atcagtactg acaataaaaa gattcttgtt ttcaagaact tgtcatttgt   1140 atagttttt  tatattgtag ttgttctatt ttaatcaaat gttagcgtga tttatatttt   1200
ttttcgcctc gacatcatct gcccagatgc gaagttaagt gcgcagaaag taatatcatg   1260
cgtcaatcgt atgtgaatgc tggtcgctat actgctgtcg attcgatact aacgccgcca   1320
tccagtgtcg aaaacgagct ctcgagaacc cttaatataa cttcgtataa tgtatgctat   1380
acgaagttat taggtgatat cagatccact agtggcctat gctgacactt tacttaatct   1440
tttccttcgt actgaacaat taatcaa                                      1467

<210> SEQ ID NO 59
<211> LENGTH: 1467
<212> TYPE: DNA
<213> ORGANISM: Artificial Sequence
```

<220> FEATURE:
<223> OTHER INFORMATION: Gene deletion construct

<400> SEQUENCE: 59

| | | |
|---|---|---|
| aagactatac cattataaaa acgcataaga aacagtttca tcatgccagc tgaagcttcg | 60 |
| tacgctgcag gtcgacaacc cttaatataa cttcgtataa tgtatgctat acgaagttat | 120 |
| taggtctaga gatctgttta gcttgccttg tccccgccgg gtcacccggc cagcgacatg | 180 |
| gaggcccaga ataccctcct tgacagtctt gacgtgcgca gctcaggggc atgatgtgac | 240 |
| tgtcgcccgt acatttagcc catacatccc catgtataat catttgcatc catacatttt | 300 |
| gatgccgca cggcgcgaag caaaaattac ggctcctcgc tgcagacctg cgagcaggga | 360 |
| aacgctcccc tcacagacgc gttgaattgt ccccacgccg cgccctgta gagaaatata | 420 |
| aaaggttagg atttgccact gaggttcttc tttcatatac ttccttttaa aatcttgcta | 480 |
| ggatacagtt ctcacatcac atccgaacat aaacaaccat gggtaccact cttgacgaca | 540 |
| cggcttaccg gtaccgcacc agtgtccgg gggacgccga ggccatcgag cactggatg | 600 |
| ggtccttcac caccgacacc gtcttccgcg tcaccgccac cggggacggc ttcaccctgc | 660 |
| gggaggtgcc ggtggacccg cccctgacca aggtgttccc cgacgacgaa tcggacgacg | 720 |
| aatcggacga cggggaggac ggcgacccgg actcccggac gttcgtcgcg tacggggacg | 780 |
| acggcgacct ggcgggcttc gtggtcgtct cgtactccgg ctggaaccgc cggctgaccg | 840 |
| tcgaggacat cgaggtcgcc ccggagcacc gggggcacgg ggtcgggcgc gcgttgatgg | 900 |
| ggctcgcgac ggagttcgcc cgcgagcggg gcgccgggca cctctggctg gaggtcacca | 960 |
| acgtcaacgc accggcgatc cacgcgtacc ggcggatggg gttcaccctc tgcggcctgg | 1020 |
| acaccgccct gtacgacggc accgcctcgg acggcgagca ggcgctctac atgagcatgc | 1080 |
| cctgcccta atcagtactg acaataaaaa gattcttgtt ttcaagaact tgtcatttgt | 1140 |
| atagttttt tatattgtag ttgttctatt ttaatcaaat gttagcgtga tttatatttt | 1200 |
| ttttcgcctc gacatcatct gcccagatgc gaagttaagt gcgcagaaag taatatcatg | 1260 |
| cgtcaatcgt atgtgaatgc tggtcgctat actgctgtcg attcgatact aacgccgcca | 1320 |
| tccagtgtcg aaaacgagct ctcgagaacc cttaatataa cttcgtataa tgtatgctat | 1380 |
| acgaagttat taggtgatat cagatccact agtggcctat gctagttggc tctgcctata | 1440 |
| cgcatatatg tatatatata tatatat | 1467 |

<210> SEQ ID NO 60
<211> LENGTH: 1706
<212> TYPE: DNA
<213> ORGANISM: Artificial Sequence
<220> FEATURE:
<223> OTHER INFORMATION: Gene deletion construct

<400> SEQUENCE: 60

| | | |
|---|---|---|
| tggtggaaaa agaattgcct tgctaagagt attgttgtcc aattaccgca taggccacta | 60 |
| gtggatctga tatcacctaa taacttcgta tagcatacat tatacgaagt tatattaagg | 120 |
| gttctcgaga gctcgttttc gacactggat ggcggcgtta gtatcgaatc gacagcagta | 180 |
| tagcgaccag cattcacata cgattgacgc atgatattac tttctgcgca cttaacttcg | 240 |
| catctgggca gatgatgtcg aggcgaaaaa aaatataaat cacgctaaca tttgattaaa | 300 |
| atagaacaac tacaatataa aaaaactata caaatgacaa gttcttgaaa acaagaatct | 360 |
| ttttattgtc agtactgatt agaaaaactc atcgagcatc aaatgaaact gcaatttatt | 420 |

| | |
|---|---|
| catatcagga ttatcaatac catattttg aaaaagccgt ttctgtaatg aaggagaaaa | 480 |
| ctcaccgagg cagttccata ggatggcaag atcctggtat cggtctgcga ttccgactcg | 540 |
| tccaacatca atacaaccta ttaatttccc ctcgtcaaaa ataaggttat caagtgagaa | 600 |
| atcaccatga gtgacgactg aatccggtga gaatggcaaa agcttatgca tttctttcca | 660 |
| gacttgttca acaggccagc cattacgctc gtcatcaaaa tcactcgcat caaccaaacc | 720 |
| gttattcatt cgtgattgcg cctgagcgag acgaaatacg cgatcgctgt taaaaggaca | 780 |
| attacaaaca ggaatcgaat gcaaccggcg caggaacact gccagcgcat caacaatatt | 840 |
| ttcacctgaa tcaggatatt cttctaatac ctggaatgct gttttgccgg ggatcgcagt | 900 |
| ggtgagtaac catgcatcat caggagtacg gataaaatgc ttgatggtcg aagaggcat | 960 |
| aaattccgtc agccagttta gtctgaccat ctcatctgta acatcattgg caacgctacc | 1020 |
| tttgccatgt ttcagaaaca actctggcgc atcgggcttc ccatacaatc gatagattgt | 1080 |
| cgcacctgat tgcccgacat tatcgcgagc ccatttatac ccatataaat cagcatccat | 1140 |
| gttggaattt aatcgcggcc tcgaaacgtg agtctttttcc ttacccatgg ttgtttatgt | 1200 |
| tcggatgtga tgtgagaact gtatcctagc aagattttaa aaggaagtat atgaaagaag | 1260 |
| aacctcagtg gcaaatccta acctttata tttctctaca ggggcgcggc gtggggacaa | 1320 |
| ttcaacgcgt ctgtgagggg agcgtttccc tgctcgcagg tctgcagcga ggagccgtaa | 1380 |
| tttttgcttc gcgccgtgcg gccatcaaaa tgtatggatg caaatgatta tacatgggga | 1440 |
| tgtatgggct aaatgtacgg gcgacagtca catcatgccc ctgagctgcg cacgtcaaga | 1500 |
| ctgtcaagga gggtattctg ggcctccatg tcgctggccg ggtgacccgg cggggacgag | 1560 |
| gcaagctaaa cagatctcta gacctaataa cttcgtatag catacattat acgaagttat | 1620 |
| attaagggtt gtcgacctgc agcgtacgaa gcttcagctg gcattctgtt tcttctattc | 1680 |
| ttttaggttt attgttcctt ctattt | 1706 |

<210> SEQ ID NO 61
<211> LENGTH: 1467
<212> TYPE: DNA
<213> ORGANISM: Artificial Sequence
<220> FEATURE:
<223> OTHER INFORMATION: Gene deletion construct

<400> SEQUENCE: 61

| | |
|---|---|
| ttattcggct tttttccgtt tgtttacgaa acataaacag tcatgccagc tgaagcttcg | 60 |
| tacgctgcag gtcgacaacc cttaatataa cttcgtataa tgtatgctat acgaagttat | 120 |
| taggtctaga gatctgttta gcttgccttg tccccgccgg gtcacccggc cagcgacatg | 180 |
| gaggcccaga taccctcct tgacagtctt gacgtgcgca gctcagggc atgatgtgac | 240 |
| tgtcgcccgt acatttagcc catacatccc catgtataat catttgcatc catacatttt | 300 |
| gatggccgca cggcgcgaag caaaaattac ggctcctcgc tgcagacctg cgagcaggga | 360 |
| aacgctcccc tcacagacgc gttgaattgt ccccacgccg cgcccctgta gagaaatata | 420 |
| aaaggttagg atttgccact gaggttcttc tttcatatac ttccttttaa aatcttgcta | 480 |
| ggatacagtt ctcacatcac atccgaacat aaacaaccat gggtaccact cttgacgaca | 540 |
| cggcttaccg gtaccgcacc agtgtcccgg ggacgccga ggccatcgag gcactggatg | 600 |
| ggtccttcac caccgacacc gtcttccgcg tcaccgccac cggggacggc ttcaccctgc | 660 |
| gggaggtgcc ggtggacccg cccctgacca aggtgttccc cgacgacgaa tcggacgacg | 720 |
| aatcggacga cggggaggac ggcgacccgg actcccggac gttcgtcgcg tacggggacg | 780 |

```
acggcgacct ggcgggcttc gtggtcgtct cgtactccgg ctggaaccgc cggctgaccg      840
tcgaggacat cgaggtcgcc ccggagcacc gggggcacgg ggtcgggcgc gcgttgatgg      900
ggctcgcgac ggagttcgcc cgcgagcggg gcgccgggca cctctggctg gaggtcacca      960
acgtcaacgc accggcgatc cacgcgtacc ggcggatggg gttcaccctc tgcggcctgg     1020
acaccgccct gtacgacggc accgcctcgg acggcgagca ggcgctctac atgagcatgc     1080
cctgccccta atcagtactg acaataaaaa gattcttgtt ttcaagaact tgtcatttgt     1140 atagttttt tatattgtag ttgttctatt ttaatcaaat gttagcgtga tttatatttt      1200
ttttcgcctc gacatcatct gcccagatgc gaagttaagt gcgcagaaag taatatcatg     1260
cgtcaatcgt atgtgaatgc tggtcgctat actgctgtcg attcgatact aacgccgcca     1320
tccagtgtcg aaaacgagct ctcgagaacc cttaatataa cttcgtataa tgtatgctat     1380
acgaagttat taggtgatat cagatccact agtggcctat gctaaatagg aagcgagaat     1440
ttttgacagc gaatgaaaaa gaaaaaa                                         1467
```

<210> SEQ ID NO 62
<211> LENGTH: 4602
<212> TYPE: DNA
<213> ORGANISM: Artificial Sequence
<220> FEATURE:
<223> OTHER INFORMATION: Gene deletion construct

<400> SEQUENCE: 62

```
cggtgcgggc ctcttcgcta ttacgccagc tggcgaaagg gggatgtgct gcaaggcgat       60
taagttgggt aacgccaggg ttttcccagt cacgacgttg taaaacgacg gccagtgaat      120
tgtaatacga ctcactatag ggcgaccctt aggatctaag cattggcgcg ccgcgcacct      180
gcgttgttac cacaactctt atgaggcccg cggacagcat caaactgtaa gattccgcca      240
cattttatac actctggtcc tttaactggc aaaccttcgg gcgtaatgcc caattttttcg     300 cctttgtctt ttgccttttt cacttcacgt gcttctggta catacttgca atttatacag      360
tgatgaccgc tgaatttgta tcttccatag catctagcac atactcgatt tttaccactc      420
caatctttat aaaaatactt gattcccttt ctgggacaag caacacagtg ttttagattc      480 ttttttttgtg atatttttaag ctgttctccc acacagcagc ctcgacatga tttcacttct     540
attttgttgc caagcaagaa attttatgg ccgcggccgc gaaatattct cctttagagc       600
gctccatttc ttctatgaag cgttttgcgg caaactcacc ttcaactgtc attgggaatg      660
tcttatgatg gtttttttgga attattatta tcctaccatc aagcgtctga cattgctgca    720
gatttctcca tctcacttta tatttggtgg catttctacc actttttttcc aacagtggtt    780 tggtagggac cctgactgac aatttatgac ctgcagtaca ttgtaatgca agacgctgat      840
aaactgttct acgcctggga tctaacctac caggttcacc ttcaaaagct ctgtgtttgg      900 tttttttgctg tatattatag attttctgat agccctgtgt gacatttatg acgcgggcag     960
cggagccatc tgcgcacata acgtaagagt tagccgtgac gtttgcgatg tctttaatttt     1020 caccgttagc catcagaata gtcgtgtttt cagaaagcgg cgcgcctaag acttagatct     1080
taaggggata tcttaatggg gagcgctgat tctcttttgg tacgcttccc atccagcatt     1140
tctgtatctt tcaccttcaa ccttaggatc tctaccctttg gcgaaaagtc ctctgccaac    1200
aatgatgata tctgatccac cacttacaac ttcgtcgacg gttctgtact gctgacccaa     1260
tgcatcgcct ttgtcgtcta aacctacacc tggggtcatg attagccaat caaacccttc     1320
```

```
ttctcttcct cccatatcgt tctgagcaat gaacccaata acgaaatctt tatcactctt   1380
tgcaatatca acggtaccct tagtatattc accgtgtgct agagaaccct tggaagacaa   1440
ttcagcaagc atcaataatc cccttggttc tttggtgacc tcttgcgcac cttgtttcaa   1500
gccagcaaca ataccagcac cagtaacccc gtgggcgttg gtgatatcag accattctgc   1560
gatacggtaa acgcccgatg tatattgtaa tttgactgtg ttaccgatat cggcgaattt   1620
tctgtcctca aatatcaaga acttgtattt ctctgccaat gctttcaatg gaacgacagt   1680
accctcataa ctgaaatcat ccaagatatc aacgtgtgtt ttcaaaaggc aaatgtatgg   1740
acccaacgtt tcaacaagtt tcaatagctc atcagtcgaa cgaacgtcaa gagaagcaca   1800
caaattggtc ttcttttcat ccattaaacg taaaagtttc gatgcaaccg gacttgcatg   1860
agtctcagct ctactggtat atgattttgt ggacatgata tcctcgaggt tccctttagt   1920
gagggttaat tgcgagcttg gcgtaatcat ggtcatagct gtttcctgtg tgaaattgtt   1980
atccgctcac aattccacac aacatacgag ccggaagcat aaagtgtaaa gcctggggtg   2040
cctaatgagt gagctaactc acattaattg cgttgcgctc actgcccgct ttccagtcgg   2100
gaaacctgtc gtgccagctg cattaatgaa tcggccaacg cgcggggaga ggcggtttgc   2160
gtattgggcg ctcttccgct tcctcgctca ctgactcgct gcgctcggtc gttcggctgc   2220
ggcgagcggt atcagctcac tcaaaggcgg taatacggtt atccacagaa tcaggggata   2280
acgcaggaaa gaacatgtga gcaaaaggcc agcaaaaggc caggaaccgt aaaaaggccg   2340
cgttgctggc gtttttccat aggctccgcc cccctgacga gcatcacaaa aatcgacgct   2400
caagtcagag gtggcgaaac ccgacaggac tataaagata ccaggcgttt ccccctggaa   2460
gctccctcgt gcgctctcct gttccgaccc tgccgcttac cggatacctg tccgcctttc   2520
tcccttcggg aagcgtggcg ctttctcata gctcacgctg taggtatctc agttcggtgt   2580
aggtcgttcg ctccaagctg ggctgtgtgc acgaaccccc cgttcagccc gaccgctgcg   2640
ccttatccgg taactatcgt cttgagtcca acccggtaag acacgactta tcgccactgg   2700
cagcagccac tggtaacagg attagcagag cgaggtatgt aggcggtgct acagagttct   2760
tgaagtggtg gcctaactac ggctacacta agaacagtat tttggtatc tgcgctctgc   2820
tgaagccagt taccttcgga aaaagagttg gtagctcttg atccggcaaa caaaccaccg   2880
ctggtagcgg tggttttttt gtttgcaagc agcagattac gcgcagaaaa aaggatctc   2940
aagaagatcc tttgatcttt tctacggggt ctgacgctca gtggaacgaa aactcacgtt   3000
aagggatttt ggtcatgaga ttatcaaaaa ggatcttcac ctagatcctt ttaaattaaa   3060
aatgaagttt taaatcaatc taaagtatat atgagtaaac ttggtctgac agttaccaat   3120
gcttaatcag tgaggcacct atctcagcga tctgtctatt tcgttcatcc atagttgcct   3180
gactccccgt cgtgtagata actacgatac gggagggctt accatctggc cccagtgctg   3240
caatgatacc gcgagaccca cgctcaccgg ctccagattt atcagcaata aaccagccag   3300
ccggaagggc cgagcgcaga agtggtcctg caactttatc cgcctccatc cagtctatta   3360
attgttgccg ggaagctaga gtaagtagtt cgccagttaa tagtttgcgc aacgttgttg   3420
ccattgctac aggcatcgtg gtgtcacgct cgtcgtttgg tatggcttca ttcagctccg   3480
gttcccaacg atcaaggcga gttacatgat cccccatgtt gtgcaaaaaa gcggttagct   3540
ccttcggtcc tccgatcgtt gtcagaagta agttggccgc agtgttatca ctcatggtta   3600
tggcagcact gcataattct cttactgtca tgccatccgt aagatgcttt tctgtgactg   3660
gtgagtactc aaccaagtca ttctgagaat agtgtatgcg gcgaccgagt tgctcttgcc   3720
```

```
cggcgtcaat acgggataat accgcgccac atagcagaac tttaaaagtg ctcatcattg    3780
gaaaacgttc ttcggggcga aaactctcaa ggatcttacc gctgttgaga tccagttcga    3840
tgtaacccac tcgtgcaccc aactgatctt cagcatcttt tactttcacc agcgtttctg    3900
ggtgagcaaa acaggaagg caaaatgccg caaaaaggg aataagggcg acacggaaat      3960
gttgaatact catactcttc cttttcaat attattgaag catttatcag ggttattgtc     4020
tcatgagcgg atacatattt gaatgtattt agaaaaataa acaaataggg gttccgcgca    4080
catttccccg aaaagtgcca cctgacgcgc cctgtagcgg cgcattaagc gcggcgggtg    4140
tggtggttac gcgcagcgtg accgctacac ttgccagcgc cctagcgccc gctccttcg     4200 cttctcttccc ttcctttctc gccacgttcg ccggctttcc ccgtcaagct ctaaatcggg   4260
ggctcccttt agggttccga tttagtgctt tacggcacct cgaccccaaa aaacttgatt    4320
agggtgatgg ttcacgtagt gggccatcgc cctgatagac ggtttttcgc cctttgacgt    4380
tggagtccac gttctttaat agtggactct tgttccaaac tggaacaaca ctcaaccctta   4440 tctcggtcta ttcttttgat ttataaggga ttttgccgat ttcggcctat tggttaaaaa    4500
atgagctgat ttaacaaaaa tttaacgcga attttaacaa atattaacg cttacaattt     4560 gccattcgcc attcaggctg cgcaactgtt gggaagggcg at                       4602

<210> SEQ ID NO 63
<211> LENGTH: 4583
<212> TYPE: DNA
<213> ORGANISM: Artificial Sequence
<220> FEATURE:
<223> OTHER INFORMATION: Gene deletion construct

<400> SEQUENCE: 63
cggtgcgggc tcttcgcta ttacgccagc tggcgaaagg gggatgtgct gcaaggcgat        60
taagttgggt aacgccaggg ttttcccagt cacgacgttg taaaacgacg gccagtgaat      120
tgtaatacga ctcactatag gcgacccctt aggatctaag cattggcgcg ccccacgacg      180
ctttgtcttc attcaacgtt tcccattgtt tttttctact attgctttgc tgtgggaaaa      240
acttatcgaa agatgacgac ttttttcttaa ttctcgtttt aagagcttgg tgagcgctag     300
gagtcactgc caggtatcgt ttgaacacgg cattagtcag ggaagtcata acacagtcct      360
ttcccgcaat tttctttttc tattactctt ggcctcctct agtacactct atattttttt      420
atgcctcggt aatgattttc atttttttt tccacctagc ggatgactct ttttttttct       480
tagcgattgg cattatcaca taatgaatta tacattatat aaagtaatgt gatttcttcg      540
aagaatatac taaaaaatga gcaggcaaga taaacgaagg caaagatggc ggccgctagt      600
gacaccgatt atttaaagct gcagcatacg atatatatac atgtgtatat atgtataccct    660 atgaatgtca gtaagtatgt atacgaacag tatgatactg aagatgacaa ggtaatgcat      720
cattctatac gtgtcattct gaacgaggcg cgctttcctt tttcttttt gcttttcctt       780 ttttttctc ttgaactcga gaaaaaaat ataaagaga tggaggaacg ggaaaaagtt          840
agttgtggtg ataggtggca agtggtattc cgtaagaaca acaagaaaag catttcatat       900
tatggctgaa ctgagcgaac aagtgcaaaa tttaagcatc aacgcaaca acgagaatgg       960 ttatgttcct cctcacttaa gaggaaaacc aagaagtgcc agaaataaca gtagcaacta     1020
caataacaac aacggcggcg cgcgcgccta agacttagatc ttaaggggat atcttaatgg    1080
ggagcgctga ttctcttttg gtacgcttcc catccagcat ttctgtatct ttcaccttca     1140
```

```
accttaggat ctctacccctt ggcgaaaagt cctctgccaa caatgatgat atctgatcca      1200
ccacttacaa cttcgtcgac ggttctgtac tgctgaccca atgcatcgcc tttgtcgtct      1260
aaacctacac ctggggtcat gattagccaa tcaaacccctt cttctcttcc tcccatatcg     1320
ttctgagcaa tgaacccaat aacgaaatct ttatcactct ttgcaatatc aacggtaccc      1380
ttagtatatt caccgtgtgc tagagaaccc ttggaagaca attcagcaag catcaataat      1440 cccccttggtt ctttggtgac ctcttgcgca ccttgtttca agccagcaac aataccagca     1500
ccagtaaccc cgtgggcgtt ggtgatatca gaccattctg cgatacggta aacgcccgat      1560
gtatattgta atttgactgt gttaccgata tcggcgaatt ttctgtcctc aaatatcaag      1620
aacttgtatt tctctgccaa tgctttcaat ggaacgacag taccctcata actgaaatca      1680
tccaagatat caacgtgtgt tttcaaaagg caaatgtatg gacccaacgt ttcaacaagt      1740
ttcaatagct catcagtcga acgaacgtca agagaagcac acaaattggt cttcttttca      1800
tccattaaac gtaaaagttt cgatgcaacc ggacttgcat gagtctcagc tctactggta      1860
tatgattttg tggacatgat atcctcgagg ttcccttttag tgagggttaa ttgcgagctt     1920
ggcgtaatca tggtcatagc tgtttcctgt gtgaaattgt tatccgctca caattccaca      1980
caacatacga gccggaagca taaagtgtaa agcctgggt gcctaatgag tgagctaact       2040
cacattaatt gcgttgcgct cactgcccgc tttccagtcg ggaaacctgt cgtgccagct      2100
gcattaatga atcggccaac gcgcggggag aggcggtttg cgtattgggc gctcttccgc      2160
ttcctcgctc actgactcgc tgcgctcggt cgttcggctg cggcgagcgg tatcagctca      2220
ctcaaaggcg gtaatacggt tatccacaga atcaggggga aacgcaggaa agaacatgtg      2280
agcaaaaggc cagcaaaagg ccaggaaccg taaaaaggcc gcgttgctgg cgttttttcca     2340 taggctccgc ccccctgacg agcatcacaa aaatcgacgc tcaagtcaga ggtggcgaaa      2400
cccgacagga ctataaagat accaggcgtt tcccccctgga agctccctcg tgcgctctcc     2460
tgttccgacc ctgccgctta ccggatacct gtccgccttt ctcccttcgg gaagcgtggc      2520
gctttctcat agctcacgct gtaggtatct cagttcggtg taggtcgttc gctccaagct      2580
gggctgtgtg cacgaacccc ccgttcagcc cgaccgctgc gccttatccg gtaactatcg      2640
tcttgagtcc aacccggtaa gacacgactt atcgccactg gcagcagcca ctggtaacag      2700
gattagcaga gcgaggtatg taggcggtgc tacagagttc ttgaagtggt ggcctaacta      2760
cggctacact agaagaacag tatttggtat ctgcgctctg ctgaagccag ttaccttcgg      2820
aaaaagagtt ggtagctctt gatccggcaa acaaaccacc gctggtagcg gtggtttttt      2880
tgtttgcaag cagcagatta cgcgcagaaa aaaaggatct caagaagatc ctttgatctt      2940
ttctacgggg tctgacgctc agtggaacga aaactcacgt taagggattt tggtcatgag      3000
attatcaaaa aggatcttca cctagatcct tttaaattaa aaatgaagtt ttaaatcaat      3060
ctaaagtata tatgagtaaa cttggtctga cagttaccaa tgcttaatca gtgaggcacc      3120
tatctcagcg atctgtctat ttcgttcatc catagttgcc tgactccccg tcgtgtagat      3180
aactacgata cgggagggct taccatctgg ccccagtgct gcaatgatac cgcgagaccc      3240
acgctcaccg gctccagatt tatcagcaat aaaccagcca gccggaaggg ccgagcgcag      3300
aagtggtcct gcaactttat ccgcctccat ccagtctatt aattgttgcc gggaagctag      3360
agtaagtagt tcgccagtta atagtttgcg caacgttgtt gccattgcta caggcatcgt      3420
ggtgtcacgc tcgtcgtttg gtatggcttc attcagctcc ggttcccaac gatcaaggcg      3480
agttacatga tcccccatgt tgtgcaaaaa agcggttagc tccttcggtc ctccgatcgt      3540
```

```
tgtcagaagt aagttggccg cagtgttatc actcatggtt atggcagcac tgcataattc    3600
tcttactgtc atgccatccg taagatgctt ttctgtgact ggtgagtact caaccaagtc    3660
attctgagaa tagtgtatgc ggcgaccgag ttgctcttgc ccggcgtcaa tacgggataa    3720
taccgcgcca catagcagaa ctttaaaagt gctcatcatt ggaaaacgtt cttcggggcg    3780
aaaactctca aggatcttac cgctgttgag atccagttcg atgtaaccca ctcgtgcacc    3840
caactgatct tcagcatctt ttactttcac cagcgtttct gggtgagcaa aacaggaag    3900 gcaaaatgcc gcaaaaagg gaataagggc gacacggaaa tgttgaatac tcatactctt    3960
cctttttcaa tattattgaa gcatttatca gggttattgt ctcatgagcg gatacatatt    4020
tgaatgtatt tagaaaaata acaaataggg gttccgcgc acatttcccc gaaaagtgcc    4080
acctgacgcg ccctgtagcg cgcattaag cgcggcgggt gtggtggtta cgcgcagcgt    4140
gaccgctaca cttgccagcg ccctagcgcc cgctcctttc gctttcttcc cttcctttct    4200
cgccacgttc gccggctttc cccgtcaagc tctaaatcgg gggctccctt tagggttccg    4260
atttagtgct ttacggcacc tcgaccccaa aaaacttgat tagggtgatg gttcacgtag    4320
tgggccatcg ccctgataga cggtttttcg ccctttgacg ttggagtcca cgttctttaa    4380
tagtggactc ttgttccaaa ctggaacaac actcaaccct atctcggtct attcttttga    4440
tttataaggg attttgccga tttcggccta ttggttaaaa aatgagctga tttaacaaaa    4500
atttaacgcg aattttaaca aaatattaac gcttacaatt tgccattcgc cattcaggct    4560
gcgcaactgt tgggaagggc gat    4583
```

<210> SEQ ID NO 64
<211> LENGTH: 4598
<212> TYPE: DNA
<213> ORGANISM: Artificial Sequence
<220> FEATURE:
<223> OTHER INFORMATION: Gene deletion construct

<400> SEQUENCE: 64

```
cggtgcgggc ctcttcgcta ttacgccagc tggcgaaagg gggatgtgct gcaaggcgat      60
taagttgggt aacgccaggg ttttcccagt cacgacgttg taaaacgacg gccagtgaat     120
tgtaatacga ctcactatag ggcgacccct aggatctaag cattggcgcg ccctcaggta     180
tcgtaagatg caagagttcg aatctcttag caaccattat ttttttcctc aacataacga     240
gaacacacag gggcgctatc gcacagaatc aaattcgatg actggaaatt ttttgttaat     300
ttcagaggtc gcctgacgca tataccttt tcaactgaaa aattgggaga aaaggaaag     360 gtgagagcgc cggaaccggc ttttcatata gaatagagaa gcgttcatga ctaaatgctt     420
gcatcacaat acttgaagtt gacaatatta tttaaggacc tattgttttt tccaataggt     480
ggttagcaat cgtcttactt tctaactttt cttaccttt acatttcagc aatatatata     540
tatatatttc aaggatatac cattctaatg gcggccgcta aaagattct ctttttttat     600 gatatttgta cataaacttt ataaatgaaa ttcataatag aaacgacacg aaattacaaa     660
atggaatatg ttcataggt agacgaaact atatacgcaa tctacataca tttatcaaga     720
aggagaaaaa ggaggatgta aaggaataca ggtaagcaaa ttgatactaa tggctcaacg     780
tgataaggaa aaagaattgc actttaacat taatattgac aaggaggagg gcaccacaca     840
aaaagttagg tgtaacagaa aatcatgaaa ctatgattcc taatttatat attggaggat     900
tttctctaaa aaaaaaaaa tacaacaaat aaaaaacact caatgacctg accatttgat     960
```

-continued

```
ggagtttaag tcaataccct cttgaaccat ttcccataat ggtgaaagtt ccctcaagaa    1020
ttttactctg tcagaaacgg ccttaacgac gtagggcgcg cctaagactt agatcttaag    1080
gggatatctt aatggggagc gctgattctc ttttggtacg cttcccatcc agcatttctg    1140
tatctttcac cttcaacctt aggatctcta cccttggcga aaagtcctct gccaacaatg    1200
atgatatctg atccaccact tacaacttcg tcgacggttc tgtactgctg acccaatgca    1260
tcgcctttgt cgtctaaacc tacacctggg gtcatgatta gccaatcaaa cccttcttct    1320
cttcctccca tatcgttctg agcaatgaac ccaataacga aatctttatc actctttgca    1380
atatcaacgg taccctagt atattcaccg tgtgctagag aacccttgga agacaattca    1440
gcaagcatca ataatcccct tggttctttg gtgacctctt gcgcaccttg tttcaagcca    1500
gcaacaatac cagcaccagt aaccccgtgg gcgttggtga tatcagacca ttctgcgata    1560
cggtaaacgc ccgatgtata ttgtaatttg actgtgttac cgatatcggc gaattttctg    1620
tcctcaaata tcaagaactt gtatttctct gccaatgctt tcaatggaac gacagtaccc    1680
tcataactga atcatccaa gatatcaacg tgtgttttca aaaggcaaat gtatggaccc    1740
aacgtttcaa caagtttcaa tagctcatca gtcgaacgaa cgtcaagaga agcacacaaa    1800
ttggtcttct tttcatccat taaacgtaaa agtttcgatg caaccggact tgcatgagtc    1860
tcagctctac tggtatatga ttttgtggac atgatatcct cgaggttccc tttagtgagg    1920
gttaattgcg agcttggcgt aatcatggtc atagctgttt cctgtgtgaa attgttatcc    1980
gctcacaatt ccacacaaca tacgagccgg aagcataaag tgtaaagcct ggggtgccta    2040
atgagtgagc taactcacat taattgcgtt gcgctcactg cccgctttcc agtcgggaaa    2100
cctgtcgtgc cagctgcatt aatgaatcgg ccaacgcgcg gggagaggcg gtttgcgtat    2160
tgggcgctct tccgcttcct cgctcactga ctcgctgcgc tcggtcgttc ggctgcggcg    2220
agcggtatca gctcactcaa aggcggtaat acggttatcc acagaatcag gggataacgc    2280
aggaaagaac atgtgagcaa aaggccagca aaaggccagg aaccgtaaaa aggccgcgtt    2340
gctggcgttt ttccataggc tccgcccccc tgacgagcat cacaaaaatc gacgctcaag    2400
tcagaggtgg cgaaacccga caggactata aagataccag gcgtttcccc ctggaagctc    2460
cctcgtgcgc tctcctgttc cgaccctgcc gcttaccgga tacctgtccg cctttctccc    2520
ttcgggaagc gtggcgcttt ctcatagctc acgctgtagg tatctcagtt cggtgtaggt    2580
cgttcgctcc aagctgggct gtgtgcacga accccccgtt cagcccgacc gctgcgcctt    2640
atccggtaac tatcgtcttg agtccaaccc ggtaagacac gacttatcgc cactggcagc    2700
agccactggt aacaggatta gcagagcgag gtatgtaggc ggtgctacag agttcttgaa    2760
gtggtggcct aactacggct acactagaag aacagtattt ggtatctgcg ctctgctgaa    2820
gccagttacc ttcggaaaaa gagttggtag ctcttgatcc ggcaaacaaa ccaccgctgg    2880
tagcggtggt ttttttgttt gcaagcagca gattacgcgc agaaaaaaag gatctcaaga    2940
agatcctttg atcttttcta cggggtctga cgctcagtgg aacgaaaact cacgttaagg    3000
gattttggtc atgagattat caaaaaggat cttcacctag atccttttaa attaaaaatg    3060
aagttttaaa tcaatctaaa gtatatatga gtaaacttgg tctgacagtt accaatgctt    3120
aatcagtgag gcacctatct cagcgatctg tctatttcgt tcatccatag ttgcctgact    3180
ccccgtcgtg tagataacta cgatacggga gggcttacca tctggcccca gtgctgcaat    3240
gataccgcga gacccacgct caccggctcc agatttatca gcaataaacc agccagccgg    3300
aagggccgag cgcagaagtg gtcctgcaac tttatccgcc tccatccagt ctattaattg    3360
```

-continued

```
ttgccgggaa gctagagtaa gtagttcgcc agttaatagt ttgcgcaacg ttgttgccat    3420
tgctacaggc atcgtggtgt cacgctcgtc gtttggtatg gcttcattca gctccggttc    3480
ccaacgatca aggcgagtta catgatcccc catgttgtgc aaaaaagcgg ttagctcctt    3540
cggtcctccg atcgttgtca gaagtaagtt ggccgcagtg ttatcactca tggttatggc    3600
agcactgcat aattctctta ctgtcatgcc atccgtaaga tgcttttctg tgactggtga    3660
gtactcaacc aagtcattct gagaatagtg tatgcggcga ccgagttgct cttgcccggc    3720
gtcaatacgg gataataccg cgccacatag cagaacttta aaagtgctca tcattggaaa    3780
acgttcttcg gggcgaaaac tctcaaggat cttaccgctg ttgagatcca gttcgatgta    3840
acccactcgt gcacccaact gatcttcagc atctttttact ttcaccagcg tttctgggtg    3900
agcaaaaaca ggaaggcaaa atgccgcaaa aaagggaata agggcgacac ggaaatgttg    3960
aatactcata ctcttccttt tcaatatta ttgaagcatt tatcagggtt attgtctcat    4020
gagcggatac atatttgaat gtatttagaa aaataaacaa ataggggttc cgcgcacatt    4080
tccccgaaaa gtgccacctg acgcgccctg tagcggcgca ttaagcgcgg cgggtgtggt    4140
ggttacgcgc agcgtgaccg ctacacttgc cagcgcccta gcgcccgctc ctttcgcttt    4200
cttcccttcc tttctcgcca cgttcgccgg ctttccccgt caagctctaa atcgggggct    4260
ccctttaggg ttccgattta gtgctttacg gcacctcgac cccaaaaaac ttgattaggg    4320
tgatggttca cgtagtgggc catcgccctg atagacggtt tttcgccctt tgacgttgga    4380
gtccacgttc tttaatagtg gactcttgtt ccaaactgga acaacactca accctatctc    4440
ggtctattct tttgatttat aagggatttt gccgatttcg gcctattggt taaaaaatga    4500
gctgatttaa caaaaattta acgcgaattt taacaaaata ttaacgctta caatttgcca    4560
ttcgccattc aggctgcgca actgttggga agggcgat                            4598
```

<210> SEQ ID NO 65
<211> LENGTH: 686
<212> TYPE: DNA
<213> ORGANISM: Saccharomyces cerevisiae

<400> SEQUENCE: 65

```
gatctcagtt cgagtttatc attatcaata ctgccatttc aaagaatacg taaataatta     60
atagtagtga ttttcctaac tttatttagt caaaaaatta gccttttaat tctgctgtaa    120
cccgtacatg cccaaaatag ggggcgggtt acacagaata tataacatcg taggtgtctg    180
ggtgaacagt ttattcctgg catccactaa atataatgga gcccgctttt taagctggca    240
tccagaaaaa aaaagaatcc cagcaccaaa atattgtttt cttcaccaac catcagttca    300
taggtccatt ctcttagcgc aactacagag aacaggggca caaacaggca aaaacggac     360 acaacctcaa tggagtgatg caacctgcct ggagtaaatg atgacacaag gcaattgacc    420
cacgcatgta tctatctcat tttcttacac cttctattac cttctgctct ctctgatttg    480
gaaaaagctg aaaaaaaagg ttgaaaccag ttccctgaaa ttattcccct acttgactaa    540
taagtatata aagacggtag gtattgattg taattctgta aatctatttc ttaaacttct    600
taaattctac ttttatagtt agtctttttt ttagttttaa aacaccaaga acttagtttc    660
gaataaacac acataaacaa acaaaa                                         686
```

<210> SEQ ID NO 66
<211> LENGTH: 559
<212> TYPE: DNA

<213> ORGANISM: Saccharomyces cerevisiae

<400> SEQUENCE: 66

| | |
|---|---:|
| gtttagttaa ttatagttcg ttgaccgtat attctaaaaa caagtactcc ttaaaaaaaa | 60 |
| accttgaagg gaataaacaa gtagaataga tagagagaaa aatagaaaat gcaagagaat | 120 |
| ttatatatta gaaagagaga aagaaaaatg gaaaaaaaa aataggaaaa gccagaaata | 180 |
| gcactagaag gagcgacacc agaaaagaag gtgatggaac caatttagct atatatagtt | 240 |
| aactaccggc tcgatcatct ctgcctccag catagtcgaa gaagaatttt ttttttcttg | 300 |
| aggcttctgt cagcaactcg tatttttttct ttcttttttg gtgagcctaa aaagttccca | 360 |
| cgttctcttg tacgacgccg tcacaaacaa ccttatgggt aatttgtcgc ggtctgggtg | 420 |
| tataaatgtg tgggtgcaac atgaatgtac ggaggtagtt tgctgattgg cggtctatag | 480 |
| ataccttggt tatggcgccc tcacagccgg caggggaagc gcctacgctt gacatctact | 540 |
| atatgtaagt atacggccc | 559 |

<210> SEQ ID NO 67
<211> LENGTH: 750
<212> TYPE: DNA
<213> ORGANISM: Saccharomyces cerevisiae

<400> SEQUENCE: 67

| | |
|---|---:|
| acgcacagat attataacat ctgcataata ggcatttgca agaattactc gtgagtaagg | 60 |
| aaagagtgag gaactatcgc atacctgcat ttaaagatgc cgatttgggc gcgaatcctt | 120 |
| tattttggct tcaccctcat actattatca gggccagaaa aaggaagtgt ttccctcctt | 180 |
| cttgaattga tgttacccctc ataaagcacg tggcctctta tcgagaaaga aattaccgtc | 240 |
| gctcgtgatt tgtttgcaaa aagaacaaaa ctgaaaaaac ccagacacgc tcgacttcct | 300 |
| gtcttcctat tgattgcagc ttccaatttc gtcacacaac aaggtcctag cgacggctca | 360 |
| caggttttgt aacaagcaat cgaaggttct ggaatggcgg gaaagggttt agtaccacat | 420 |
| gctatgatgc ccactgtgat ctccagagca aagttcgttc gatcgtactg ttactctctc | 480 |
| tctttcaaac agaattgtcc gaatcgtgtg acaacaacag cctgttctca cacactcttt | 540 |
| tcttctaacc aagggggtgg tttagtttag tagaacctcg tgaaacttac atttacatat | 600 |
| atataaactt gcataaattg gtcaatgcaa gaaatacata tttggtcttt tctaattcgt | 660 |
| agttttcaa gttcttagat gctttctttt tctcttttt acagatcatc aaggaagtaa | 720 |
| ttatctactt tttacaacaa atataaaaca | 750 |

<210> SEQ ID NO 68
<211> LENGTH: 532
<212> TYPE: DNA
<213> ORGANISM: Saccharomyces cerevisiae

<400> SEQUENCE: 68

| | |
|---|---:|
| agttataata atcctacgtt agtgtgagcg ggatttaaac tgtgaggacc ttaatacatt | 60 |
| cagacacttc tgcggtatca ccctacttat tcccttcgag attatatcta ggaacccatc | 120 |
| aggttggtgg aagattaccc gttctaagac ttttcagctt cctctattga tgttacacct | 180 |
| ggacacccct tttctggcat ccagttttta atcttcagtg catgtgaga ttctccgaaa | 240 |
| ttaattaaag caatcacaca attctctcgg ataccacctc ggttgaaact gacaggtggt | 300 |
| ttgttacaca tgctaatgca aaggagccta tatacctttg gctcggctgc tgtaacaggg | 360 |
| aatataaagg gcagcataat ttaggagttt agtgaacttg caacatttac tattttccct | 420 |

```
tcttacgtaa atattttct tttaattct aaatcaatct ttttcaattt tttgtttgta      480
ttcttttctt gcttaaatct ataactacaa aaaacacata cataaactaa aa            532

<210> SEQ ID NO 69
<211> LENGTH: 413
<212> TYPE: DNA
<213> ORGANISM: Saccharomyces cerevisiae

<400> SEQUENCE: 69
ttagcttcaa aatgtttcta ctccttttt actcttccag attttctcgg actccgcgca     60
tcgccgtacc acttcaaaac acccaagcac agcatactaa atttccctc tttcttcctc   120 tagggtgtcg ttaattaccc gtactaaagg tttggaaaag aaaaaagaga ccgcctcgtt   180 tcttttctt cgtcgaaaaa ggcaataaaa atttttatca cgtttcttt tcttgaaaat    240 tttttttttt gattttttc tctttcgatg acctcccatt gatatttaag ttaataaacg   300
gtcttcaatt tctcaagttt cagtttcatt tttcttgttc tattacaact ttttttactt   360
cttgctcatt agaaagaaag catagcaatc taatctaagt tttaattaca aaa           413

<210> SEQ ID NO 70
<211> LENGTH: 326
<212> TYPE: DNA
<213> ORGANISM: Saccharomyces cerevisiae

<400> SEQUENCE: 70
ggcacgtccg acggcggccc gacgggtccg aggcctcgga gatccgtccc ccttttcctt    60
tgtcgatatc atgtaattag ttatgtcacg cttacattca cgccctcccc ccacatccgc   120
tctaaccgaa aaggaaggag ttagacaacc tgaagtctag gtccctattt atttttttat   180
agttatgtta gtattaagaa cgttatttat atttcaaatt ttttcttttt ttctgtacag   240
acgcgtgtac gcatgtaaca ttatactgaa aaccttgctt gagaaggttt tgggacgctc   300
gaaggcttta atttgcaagc tgcatg                                         326

<210> SEQ ID NO 71
<211> LENGTH: 352
<212> TYPE: DNA
<213> ORGANISM: Saccharomyces cerevisiae

<400> SEQUENCE: 71
acaaatcgct cttaaatata tacctaaaga acattaaagc tatattataa gcaaagatac    60
gtaaattttg cttatattat tatacacata tcatatttct atattttaa gatttggtta    120 tataatgtac gtaatgcaaa ggaaataaat tttatacatt attgaacagc gtccaagtaa   180
ctacattatg tgcactaata gtttagcgtc gtgaagactt tattgtgtcg cgaaaagtaa   240 aaatttaaa aattagagca ccttgaactt gcgaaaaagg ttctcatcaa ctgtttaaaa   300
ggaggatatc aggtcctatt tctgacaaac aatatacaaa tttagtttca aa            352

<210> SEQ ID NO 72
<211> LENGTH: 311
<212> TYPE: DNA
<213> ORGANISM: Saccharomyces cerevisiae

<400> SEQUENCE: 72
ggatctctta tgtctttacg atttatagtt ttcattatca agtatgccta tattagtata    60
tagcatcttt agatgacagt gttcgaagtt tcacgaataa aagataatat tctactttt   120
```

```
gctcccaccg cgtttgctag cacgagtgaa caccatccct cgcctgtgag ttgtacccat      180
tcctctaaac tgtagacatg gtagcttcag cagtgttcgt tatgtacggc atcctccaac      240
aaacagtcgg ttatagtttg tcctgctcct ctgaatcgtc tccctcgata tttctcattt      300
tccttcgcat g                                                           311

<210> SEQ ID NO 73
<211> LENGTH: 352
<212> TYPE: DNA
<213> ORGANISM: Saccharomyces cerevisiae

<400> SEQUENCE: 73
ataaagcact cttgatgagg ataatgattt tttttgaat atacataaat actaccgttt        60
ttctgctaga ttttgtgaag acgtaaataa gtacatatta cttttaagc caagacaaga      120 ttaagcatta actttaccct tttctcttct aagtttcaat actagttatc actgtttaaa      180
agttatggcg agaacgtcgg cggttaaaat atattaccct gaacgtggtg aattgaagtt      240
ctaggatggt ttaaagattt ttccttttg ggaataagt aaacaatata ttgctgcctt       300
tgcaaaacgc acatacccac aatatgtgac tattggcaaa gaacgcaacg cg             352

<210> SEQ ID NO 74
<211> LENGTH: 292
<212> TYPE: DNA
<213> ORGANISM: Saccharomyces cerevisiae

<400> SEQUENCE: 74
ttcttcgcca gaggtttggt caagtctcca atcaaggttg tcggcttgtc taccttgcca       60
gaaatttacg aaaagatgga aaagggtcaa atcgttggta gatacgttgt tgacacttct      120
aaataagcga atttcttatg atttatgatt tttattatta aataagttat aaaaaaaata      180
agtgtataca aattttaaag tgactcttag gttttaaaac gaaaattctt attcttgagt      240
aactctttcc tgtaggtcag gttgctttct caggtatagc atgaggtcgc tc              292
```